US012697431B2

(12) United States Patent
Focht et al.

(10) Patent No.: US 12,697,431 B2
(45) Date of Patent: *Aug. 4, 2026

(54) SPLIT PISTON METERING PUMP

(71) Applicant: Becton, Dickinson and Company, Franklin Lakes, NJ (US)

(72) Inventors: Kenneth Focht, Needham, MA (US); Joseph Gordon, Mansfield, MA (US); Matthew J. Perry, East Greenwich, RI (US); Justin Fisk, Franklin, MA (US)

(73) Assignee: BECTON DICKINSON AND COMPANY, Franklin Lakes, NJ (US)

( * ) Notice: Subject to any disclaimer, the term of this patent is extended or adjusted under 35 U.S.C. 154(b) by 508 days.

This patent is subject to a terminal disclaimer.

(21) Appl. No.: 18/479,386

(22) Filed: Oct. 2, 2023

(65) Prior Publication Data

US 2024/0024568 A1     Jan. 25, 2024

Related U.S. Application Data

(62) Division of application No. 16/685,847, filed on Nov. 15, 2019, now Pat. No. 11,793,929, which is a division of application No. 15/989,848, filed on May 25, 2018, now Pat. No. 10,512,719, which is a (Continued)

(51) Int. Cl.
| | |
|---|---|
| *A61M 5/142* | (2006.01) |
| *A61M 5/145* | (2006.01) |
| *A61M 5/168* | (2006.01) |
| *F15B 15/14* | (2006.01) |
| *F16J 1/00* | (2006.01) |

(52) U.S. Cl.
CPC ........ *A61M 5/1422* (2013.01); *A61M 5/1452* (2013.01); *A61M 5/16809* (2013.01); *F15B 15/1447* (2013.01); *F16J 1/005* (2013.01)

(58) Field of Classification Search
CPC ............. A61M 5/142; A61M 5/14216; A61M 5/1422; A61M 5/1452; A61M 5/16809; F04B 7/045; F04B 9/02; F04B 9/04; F15B 15/1447; F16J 1/005
See application file for complete search history.

(56) References Cited

U.S. PATENT DOCUMENTS

| | | | | |
|---|---|---|---|---|
| 1,516,032 A | * | 11/1924 | White | ....................... F04B 3/00 417/498 |
| 3,464,359 A | * | 9/1969 | Johnson | ................ A61M 5/142 604/152 |
| 3,857,382 A | | 12/1974 | Williams, Jr. et al. | |

(Continued)

FOREIGN PATENT DOCUMENTS

| | | |
|---|---|---|
| EP | 0980687 A2 | 2/2000 |
| EP | 1044374 B1 | 10/2008 |

(Continued)

*Primary Examiner* — Kyle Robert Thomas
(74) *Attorney, Agent, or Firm* — Dickinson Wright, PLLC

(57) ABSTRACT

A micropump according to the invention uses axially oriented pistons to define a pump volume. Translating the pistons axially with respect to each other within a pump housing draws a metered amount of fluid into the pump volume from a reservoir port for delivery to a cannula port when the space is collapsed. Radially situated seals on the pistons cooperate with the axial movement to close off and open the cannula port and the reservoir port respectively at different positions of the piston stroke.

13 Claims, 45 Drawing Sheets

Related U.S. Application Data division of application No. 14/256,365, filed on Apr. 18, 2014, now Pat. No. 10,004,845.

(56) References Cited

U.S. PATENT DOCUMENTS

| | | | |
|---|---|---|---|
| 3,963,380 A | 6/1976 | Thomas, Jr. et al. |
| 4,204,538 A | 5/1980 | Cannon |
| 4,465,478 A | 8/1984 | Sabelman |
| 4,685,902 A | 8/1987 | Edwards et al. |
| 4,723,947 A | 2/1988 | Konopka |
| 4,734,092 A | 3/1988 | Millerd |
| 4,755,173 A | 7/1988 | Konopka et al. |
| 5,002,528 A | 3/1991 | Palestrant |
| 5,176,662 A | 1/1993 | Bartholomew et al. |
| 5,207,666 A | 5/1993 | Idriss et al. |
| 5,226,899 A | 7/1993 | Lee et al. |
| 5,257,980 A | 11/1993 | Van Antwerp et al. |
| 5,279,585 A | 1/1994 | Balkwill |
| 5,279,586 A | 1/1994 | Balkwill |
| 5,453,099 A | 9/1995 | Lee et al. |
| 5,522,803 A | 6/1996 | Teissen-Simony |
| 5,536,249 A | 7/1996 | Castellano et al. |
| 5,545,143 A | 8/1996 | Fischell |
| 5,545,152 A | 8/1996 | Funderburk et al. |
| 5,549,575 A | 8/1996 | Giambattista |
| 5,569,214 A | 10/1996 | Chanoch |
| 5,582,598 A | 12/1996 | Chanoch |
| 5,593,390 A | 1/1997 | Castellano et al. |
| 5,674,204 A | 10/1997 | Chanoch |
| 5,728,074 A | 3/1998 | Castellano et al. |
| 5,807,075 A | 9/1998 | Jacobsen et al. |
| 5,820,602 A | 10/1998 | Kovelman et al. |
| 5,851,197 A | 12/1998 | Marano et al. |
| 5,858,001 A | 1/1999 | Tsals et al. |
| 5,858,005 A | 1/1999 | Kriesel |
| 5,921,966 A | 7/1999 | Bendek |
| 5,925,021 A | 7/1999 | Castellano et al. |
| 5,944,700 A | 8/1999 | Nguyen |
| 5,957,895 A | 9/1999 | Sage et al. |
| 5,957,896 A | 9/1999 | Bendek |
| 5,968,011 A | 10/1999 | Larsen et al. |
| 5,980,506 A | 11/1999 | Mathiasen |
| 6,017,328 A | 1/2000 | Fischell et al. |
| 6,056,718 A | 5/2000 | Funderburk et al. |
| 6,068,615 A | 5/2000 | Brown et al. |
| 6,074,369 A | 6/2000 | Sage et al. |
| 6,086,575 A | 7/2000 | Mejslov |
| 6,093,172 A | 7/2000 | Funderburk et al. |
| 6,096,010 A | 8/2000 | Walters |
| 6,110,148 A | 8/2000 | Brown et al. |
| 6,110,149 A | 8/2000 | Klitgaard |
| 6,123,690 A | 9/2000 | Mejslov |
| 6,132,400 A | 10/2000 | Waldenburg |
| 6,175,752 B1 | 1/2001 | Say et al. |
| 6,221,053 B1 | 4/2001 | Walters |
| 6,248,095 B1 | 6/2001 | Giambattista et al. |
| 6,254,586 B1 | 7/2001 | Mann et al. |
| 6,272,364 B1 | 8/2001 | Kurnik |
| 6,275,717 B1 | 8/2001 | Gross et al. |
| 6,277,099 B1 | 8/2001 | Strowe |
| 6,277,627 B1 | 8/2001 | Hellinga |
| 6,293,925 B1 | 9/2001 | Safabash et al. |
| 6,302,866 B1 | 10/2001 | Marggi |
| 6,352,523 B1 | 3/2002 | Brown et al. |
| 6,355,021 B1 | 3/2002 | Nielsen et al. |
| 6,391,005 B1 | 5/2002 | Lum et al. |
| 6,485,461 B1 | 11/2002 | Mason et al. |
| 6,520,938 B1 | 2/2003 | Funderburk et al. |
| 6,521,446 B2 | 2/2003 | Hellinga |
| 6,537,242 B1 | 3/2003 | Palmer |
| 6,544,212 B2 | 4/2003 | Galley et al. |
| 6,546,269 B1 | 4/2003 | Kurnik |
| 6,551,276 B1 | 4/2003 | Mann et al. |
| 6,558,351 B1 | 5/2003 | Steil et al. |
| 6,565,509 B1 | 5/2003 | Say et al. |
| 6,576,430 B1 | 6/2003 | Hsieh et al. |
| 6,579,267 B2 | 6/2003 | Lynch et al. |
| 6,582,404 B1 | 6/2003 | Klitgaard et al. |
| 6,589,229 B1 | 7/2003 | Connelly et al. |
| 6,607,509 B2 | 8/2003 | Bobroff et al. |
| 6,656,158 B2 | 12/2003 | Mahoney et al. |
| 6,656,159 B2 | 12/2003 | Flaherty |
| 6,669,669 B2 | 12/2003 | Flaherty et al. |
| 6,692,457 B2 | 2/2004 | Flaherty |
| 6,692,472 B2 | 2/2004 | Hansen |
| 6,699,218 B2 | 3/2004 | Flaherty et al. |
| 6,706,159 B2 | 3/2004 | Moerman et al. |
| 6,723,072 B2 | 4/2004 | Flaherty et al. |
| 6,740,059 B2 | 5/2004 | Flaherty |
| 6,749,560 B1 | 6/2004 | Konstrorum et al. |
| 6,749,587 B2 | 6/2004 | Flaherty |
| 6,768,425 B2 | 7/2004 | Flaherty et al. |
| 6,830,558 B2 | 12/2004 | Flaherty et al. |
| 6,830,562 B2 | 12/2004 | Mogensen et al. |
| 6,840,922 B2 | 1/2005 | Nielsen et al. |
| 6,852,104 B2 | 2/2005 | Blomquist |
| 6,932,794 B2 | 8/2005 | Giambattista |
| 6,936,032 B1 | 8/2005 | Bush, Jr. |
| 6,945,961 B2 | 9/2005 | Miller |
| 6,949,084 B2 | 9/2005 | Marggi et al. |
| 6,960,162 B2 | 11/2005 | Saadat et al. |
| 6,960,192 B1 | 11/2005 | Flaherty et al. |
| 6,977,180 B2 | 12/2005 | Hellinga et al. |
| 6,997,907 B2 | 2/2006 | Safabash et al. |
| 7,004,928 B2 | 2/2006 | Aceti et al. |
| 7,018,360 B2 | 3/2006 | Flaherty et al. |
| 7,018,364 B2 | 3/2006 | Giambattista |
| 7,029,455 B2 | 4/2006 | Flaherty |
| 7,052,251 B2 | 5/2006 | Nason et al. |
| 7,064,103 B2 | 6/2006 | Pitner et al. |
| 7,070,580 B2 | 7/2006 | Nielsen |
| 7,083,597 B2 | 8/2006 | Lynch et al. |
| 7,104,972 B2 | 9/2006 | Moller |
| 7,109,878 B2 | 9/2006 | Mann et al. |
| 7,128,727 B2 | 10/2006 | Flaherty et al. |
| 7,137,964 B2 | 11/2006 | Flaherty |
| 7,144,384 B2 | 12/2006 | Gorman et al. |
| 7,169,132 B2 | 1/2007 | Bendek |
| 7,207,974 B2 | 4/2007 | Safabash et al. |
| 7,214,207 B2 | 5/2007 | Lynch et al. |
| 7,220,248 B2 | 5/2007 | Mernoe |
| 7,226,278 B2 | 6/2007 | Nason et al. |
| 7,250,037 B2 | 7/2007 | Shermer et al. |
| 7,303,543 B1 | 12/2007 | Maule et al. |
| 7,303,549 B2 | 12/2007 | Flaherty et al. |
| 7,310,544 B2 | 12/2007 | Brister et al. |
| 7,318,816 B2 | 1/2008 | Bobroff et al. |
| 7,329,239 B2 | 2/2008 | Safabash et al. |
| 7,354,420 B2 | 4/2008 | Steil et al. |
| 7,496,392 B2 | 2/2009 | Alarcon et al. |
| 7,678,079 B2 | 3/2010 | Shermer et al. |
| 7,722,595 B2 | 5/2010 | Pettis et al. |
| 7,726,955 B2 | 6/2010 | Ryser et al. |
| 7,857,131 B2 | 12/2010 | Vedrine |
| 8,021,334 B2 | 9/2011 | Shekalim |
| 8,282,366 B2 | 10/2012 | Hilber et al. |
| 2002/0040208 A1 | 4/2002 | Flaherty et al. |
| 2003/0055380 A1 | 3/2003 | Flaherty |
| 2003/0109829 A1 | 6/2003 | Mogensen et al. |
| 2003/0176852 A1 | 9/2003 | Lynch et al. |
| 2003/0199823 A1 | 10/2003 | Bobroff et al. |
| 2004/0002682 A1 | 1/2004 | Kovelman et al. |
| 2004/0010207 A1 | 1/2004 | Flaherty et al. |
| 2004/0059316 A1 | 3/2004 | Smedegaard |
| 2004/0078028 A1 | 4/2004 | Flaherty et al. |
| 2004/0092865 A1 | 5/2004 | Flaherty et al. |
| 2004/0092878 A1 | 5/2004 | Flaherty |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0162521 A1 | 8/2004 | Bengtsson |
| 2004/0204673 A1 | 10/2004 | Flaherty |
| 2004/0204687 A1 | 10/2004 | Mogensen et al. |
| 2004/0220551 A1 | 11/2004 | Flaherty et al. |

(56)  References Cited

U.S. PATENT DOCUMENTS

| | | |
|---|---|---|
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0043687 A1 | 2/2005 | Mogensen et al. |
| 2005/0065760 A1 | 3/2005 | Murtfeldt et al. |
| 2005/0090784 A1 | 4/2005 | Nielsen et al. |
| 2005/0101932 A1 | 5/2005 | Cote et al. |
| 2005/0101933 A1 | 5/2005 | Marrs et al. |
| 2005/0113761 A1 | 5/2005 | Faust et al. |
| 2005/0124936 A1 | 6/2005 | Mogensen et al. |
| 2005/0171512 A1 | 8/2005 | Flaherty |
| 2005/0182366 A1 | 8/2005 | Vogt et al. |
| 2005/0197625 A1 | 9/2005 | Haueter |
| 2005/0215982 A1 | 9/2005 | Malave et al. |
| 2005/0222645 A1 | 10/2005 | Malave et al. |
| 2005/0238507 A1 | 10/2005 | Dilanni et al. |
| 2005/0245799 A1 | 11/2005 | Brauker et al. |
| 2005/0273076 A1 | 12/2005 | Beasley et al. |
| 2005/0283144 A1 | 12/2005 | Shiono et al. |
| 2006/0041229 A1 | 2/2006 | Garibotto et al. |
| 2006/0074381 A1 | 4/2006 | Malave et al. |
| 2006/0122577 A1 | 6/2006 | Poulsen et al. |
| 2006/0129090 A1 | 6/2006 | Moberg et al. |
| 2006/0135913 A1 | 6/2006 | Ethelfeld |
| 2006/0142698 A1 | 6/2006 | Ethelfeld |
| 2006/0178633 A1 | 8/2006 | Garibotto et al. |
| 2006/0200073 A1 | 9/2006 | Radmer et al. |
| 2006/0253086 A1 | 11/2006 | Moberg et al. |
| 2006/0263839 A1 | 11/2006 | Ward et al. |
| 2006/0264835 A1 | 11/2006 | Nielsen et al. |
| 2006/0282290 A1 | 12/2006 | Flaherty et al. |
| 2007/0016149 A1 | 1/2007 | Hunn et al. |
| 2007/0021733 A1 | 1/2007 | Hansen et al. |
| 2007/0049865 A1 | 3/2007 | Radmer et al. |
| 2007/0060894 A1 | 3/2007 | Dai |
| 2007/0073229 A1 | 3/2007 | Gorman et al. |
| 2007/0073559 A1 | 3/2007 | Stangel |
| 2007/0088244 A1 | 4/2007 | Miller et al. |
| 2007/0088271 A1 | 4/2007 | Richards |
| 2007/0118405 A1 | 5/2007 | Campbell et al. |
| 2007/0191702 A1 | 8/2007 | Yodfat et al. |
| 2007/0261677 A1 | 11/2007 | Bennion |
| 2008/0004515 A1 | 1/2008 | Jennewine |
| 2008/0051697 A1 | 2/2008 | Mounce et al. |
| 2008/0051698 A1 | 2/2008 | Mounce et al. |
| 2008/0051709 A1 | 2/2008 | Mounce et al. |
| 2008/0051710 A1 | 2/2008 | Moberg et al. |
| 2008/0051711 A1 | 2/2008 | Mounce et al. |
| 2008/0051714 A1 | 2/2008 | Moberg et al. |
| 2008/0051716 A1 | 2/2008 | Stutz |
| 2008/0051718 A1 | 2/2008 | Kavazov et al. |
| 2008/0051727 A1 | 2/2008 | Moberg et al. |
| 2008/0051730 A1 | 2/2008 | Bikovsky |
| 2008/0051738 A1 | 2/2008 | Griffin |
| 2008/0051765 A1 | 2/2008 | Mounce |
| 2008/0086111 A1 | 4/2008 | Cowan |
| 2008/0097321 A1 | 4/2008 | Mounce et al. |
| 2008/0097326 A1 | 4/2008 | Moberg et al. |
| 2008/0097327 A1 | 4/2008 | Bente et al. |
| 2008/0097328 A1 | 4/2008 | Moberg et al. |
| 2008/0097375 A1 | 4/2008 | Bikovsky |
| 2008/0097381 A1 | 4/2008 | Moberg et al. |
| 2008/0114305 A1 | 5/2008 | Gerondale |
| 2008/0116647 A1 | 5/2008 | Anderson et al. |
| 2008/0119707 A1 | 5/2008 | Stafford |
| 2008/0132842 A1 | 6/2008 | Flaherty |
| 2008/0147041 A1 | 6/2008 | Kristensen |
| 2008/0160492 A1 | 7/2008 | Campbell et al. |
| 2008/0194924 A1 | 8/2008 | Valk et al. |
| 2008/0215006 A1 | 9/2008 | Thorkild |
| 2008/0261255 A1 | 10/2008 | Tolosa et al. |
| 2008/0264261 A1 | 10/2008 | Kavazov et al. |
| 2008/0269680 A1 | 10/2008 | Ibranyan et al. |
| 2008/0269713 A1 | 10/2008 | Kavazov |
| 2008/0294028 A1 | 11/2008 | Brown |
| 2008/0306434 A1 | 12/2008 | Dobbles et al. |
| 2008/0312608 A1 | 12/2008 | Christoffersen et al. |
| 2009/0005724 A1 | 1/2009 | Regittnig et al. |
| 2009/0005728 A1 | 1/2009 | Weinert et al. |
| 2009/0012472 A1 | 1/2009 | Ahm et al. |
| 2009/0048563 A1 | 2/2009 | Ethelfeld et al. |
| 2009/0062767 A1 | 3/2009 | Van Antwerp et al. |
| 2009/0062778 A1 | 3/2009 | Bengtsson et al. |
| 2009/0076453 A1 | 3/2009 | Mejlhede et al. |
| 2009/0149743 A1 | 6/2009 | Barron |
| 2009/0204077 A1 | 8/2009 | Hasted et al. |
| 2009/0221971 A1 | 9/2009 | Mejlhede et al. |
| 2010/0218586 A1 | 9/2010 | Rosinko et al. |
| 2011/0021990 A1 | 1/2011 | Navarro et al. |
| 2011/0054400 A1 | 3/2011 | Chong et al. |
| 2011/0230838 A1 | 9/2011 | Adams |
| 2012/0118138 A1 | 5/2012 | Navarro et al. |
| 2015/0290389 A1* | 10/2015 | Nessel .................. F04B 3/00 604/152 |

FOREIGN PATENT DOCUMENTS

| | | |
|---|---|---|
| EP | 2019206 A1 | 1/2009 |
| EP | 2357454 A1 | 8/2011 |
| EP | 2 992 916 B1 | 11/2019 |
| GB | 1508665 | 4/1978 |
| JP | 08072266 A | 3/1996 |
| JP | 2003509133 | 3/2003 |
| JP | 2004503303 | 2/2004 |
| JP | 2004524869 | 8/2004 |
| JP | 2005520646 | 7/2005 |
| JP | 2006526467 | 11/2006 |
| JP | 2010527273 A | 8/2010 |
| JP | 2015536742 A | 12/2015 |
| WO | WO-1999034212 | 7/1999 |
| WO | WO-03074121 | 9/2003 |
| WO | WO-2004032994 | 4/2004 |
| WO | WO-2007051139 | 5/2007 |
| WO | WO-2007119149 A2 | 10/2007 |
| WO | WO-2008040812 | 4/2008 |
| WO | WO-2008086349 A1 | 7/2008 |
| WO | WO-2008141337 A1 | 11/2008 |
| WO | WO-2009004627 | 1/2009 |
| WO | WO-2009021039 | 2/2009 |
| WO | WO-2009021052 | 2/2009 |
| WO | WO-2012069308 | 5/2012 |
| WO | WO-2012084033 A1 | 6/2012 |
| WO | WO-2012126744 | 9/2012 |
| WO | WO-2013190428 A1 | 12/2013 |
| WO | WO-2014090745 A1 | 6/2014 |
| WO | WO-2014207532 A1 | 12/2014 |

* cited by examiner

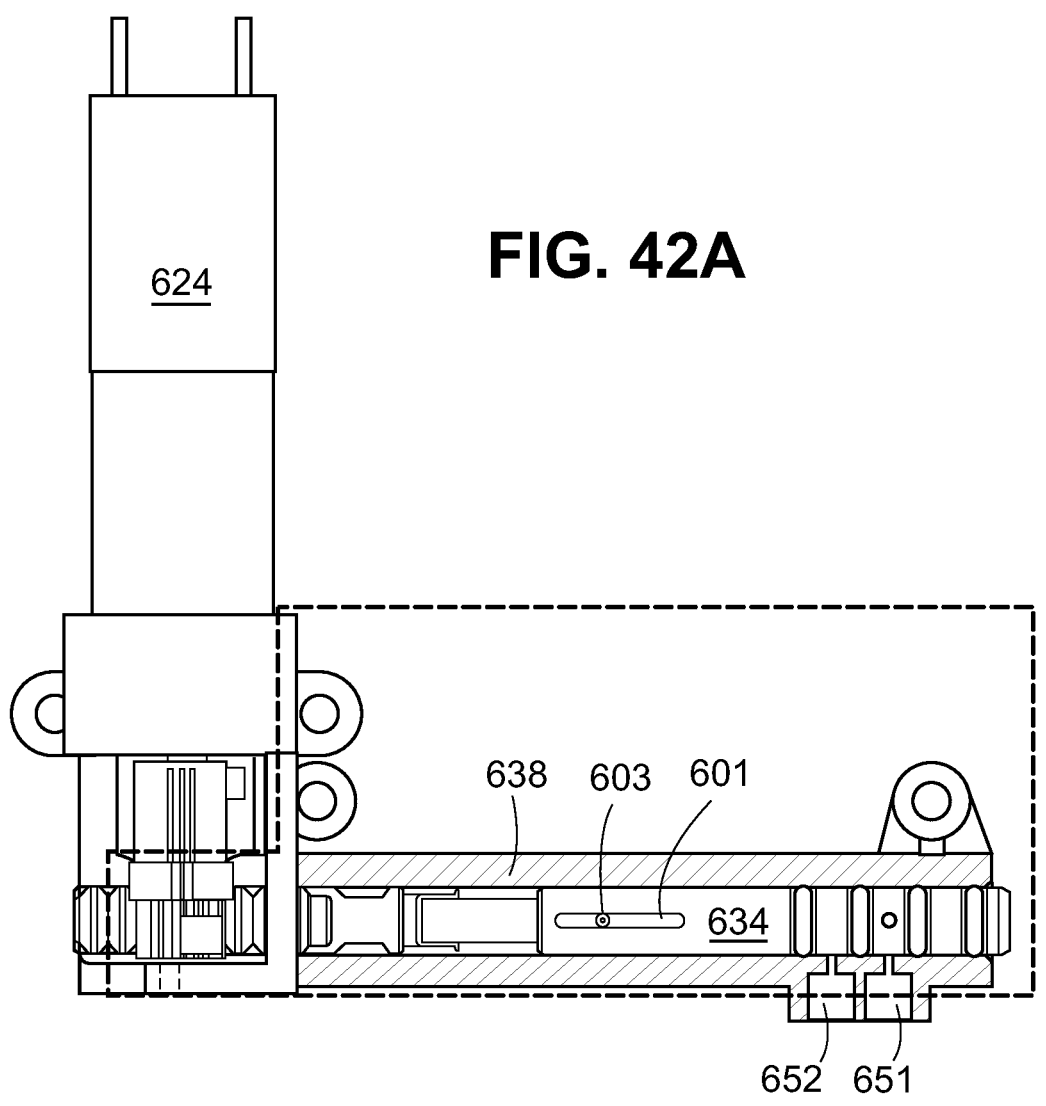
FIG. 42A
FIG. 42B
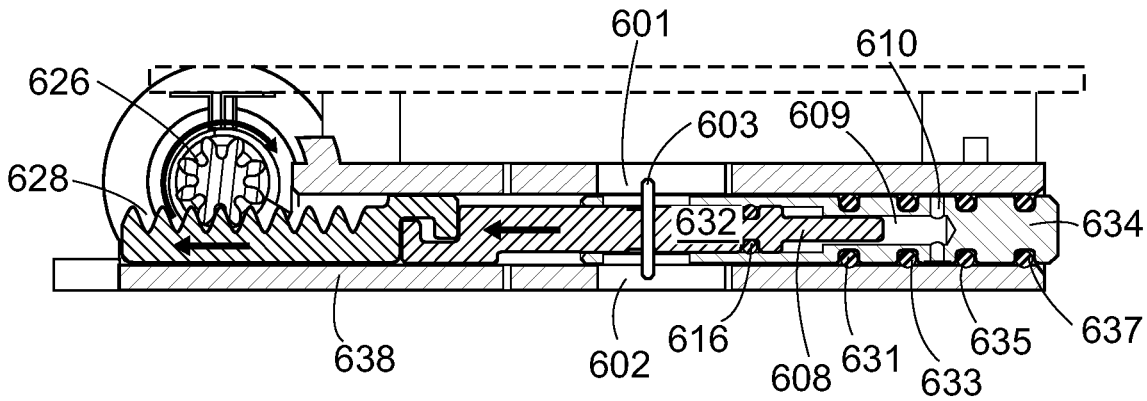

SPLIT PISTON METERING PUMP

RELATED APPLICATION

This application is a division of U.S. patent application Ser. No. 16/685,847, filed Nov. 15, 2019, which is a divisional of U.S. patent application Ser. No. 15/989,848, filed May 25, 2018, now U.S. Pat. No. 10,512,719, issued on Dec. 24, 2019, which is a divisional of U.S. patent application Ser. No. 14/256,365, filed on Apr. 18, 2014, now U.S. Pat. No. 10,004,845, issued on Jun. 26, 2018, including the specification, drawings and abstract, the entire disclosure of which is incorporated herein by reference.

BACKGROUND OF THE INVENTION

Field of the Invention

The present invention is directed to a micropump adapted for the continuous delivery of a liquid medication by infusion such as may be used in the delivery of insulin for the treatment of diabetes.

Description of the Related Art

Micropumps for subcutaneous delivery of drugs are known, for example, from U.S. Pat. Nos. 7,726,955 and 8,282,366. This prior art describes, in various embodiments, a pump having a rotor mounted in a stator, or housing. Sealing rings situated at an angle on axial extensions on the rotor cooperate with channels formed between the rotor and the stator to move liquid in precise amounts through a rotor housing. However, these embodiments are relatively complex and not cost effective. The user keeps the pump when the infusion patch is changed for several weeks. As the art continues to evolve toward fully disposable pumps, the need for compact and economical micropump designs remains acute.

Another infusion pump known in the prior art comprises a rigid reservoir with a lead screw engaged in the reservoir to dispense medication through a cannula as the lead screw advances. In this arrangement, the actuator for delivery of the medication is directly connected to the lead screw and dosing precision depends on variables that are difficult to control, such as the precision of the motor. Moreover, the device requires the rigid reservoir to provide calibrated dosages. Thus, it is impossible to use a flexible reservoir and the number of possible layouts for the pump is consequently limited.

SUMMARY OF THE INVENTION

A micropump according to the invention is provided for the delivery of medication by infusion. Although described in connection with delivery of insulin, the micropump may be used for infusion of other medications. The micropump comprises: a reservoir; a cannula; a motor; a gear; a drive rack and a tubular pump housing having a first aperture in fluid communication with the reservoir and a second aperture in fluid communication with the cannula. A drive piston and a floating piston are axially oriented within the pump housing and positioned to close the first and second aperture at first and second axial positions within the pump housing. The motor is engaged to the gear and the gear is engaged to the drive rack to translate the drive piston axially with respect to the floating piston, so that translating the drive piston with respect to the floating piston defines a pump volume space within the pump housing.

In a first embodiment, the drive piston is coupled to the floating piston, and the drive rack is axially oriented with respect to the pump housing and coupled to the drive piston to translate the drive piston in the pump housing.

In a second embodiment, the drive piston is in a fixed position, the floating piston is not coupled to the drive piston, the drive rack is on the pump housing, and the pump housing is translated by the motor and gear to obtain said first and second axial positions of the drive piston and the floating piston.

In a third embodiment, the floating piston (which is also called a "spool" in this embodiment) is provided with an axial bore receiving a portion of the drive piston to define a pump volume space in the bore. A through-hole provided on the floating piston opens to the bore and to an outer surface of the floating piston, and is positioned to provide access to the reservoir via the first aperture in the first position and access to the cannula via the second aperture in the second position.

In a fourth embodiment, which is a variation of the third embodiment, the gear engages the drive rack through an opening in the pump housing, which permits a shorter axial length of the piston arrangement and a smaller footprint overall.

In a fifth embodiment, which is another variation of the third embodiment, the drive piston is provided with an axial extension narrower than a main body portion of the drive piston which is received in a recess at one end of the bore in the floating piston. The pump volume space is defined between the axial extension on the drive piston and the end of the recess in the floating piston bore.

Further variations are described in the detailed description which follows. In each of these embodiments and variations, the pump volume space is defined by the relative position of pistons axially arranged in a tubular pump housing. In each of the embodiments and variations, the frictional engagement of radial seals on the drive piston and/or the floating piston with the interior surface of the tubular pump housing determines the opening and closing of the apertures in the pump housing to provide access to the reservoir and cannula at different times during the pump cycle.

BRIEF DESCRIPTION OF THE DRAWINGS

FIG. 2 is an exploded view of the fluid metering subsystem.

FIG. 14 is a side cross sectional view of the fluid metering system of FIG. 13 prior to the initiation of the pump cycle.

FIG. 15, FIG. 16, FIG. 17, FIG. 18, FIG. 19, and FIG. 20 depict stages of the pump cycle of the fluid metering system according to the embodiment of FIG. 13.

FIG. 21 is an exploded view of a fluid metering subsystem according to a third exemplary embodiment of the invention.

FIG. 42A, FIG. 42B, FIG. 43A, FIG. 43B, FIG. 44A, FIG. 44B, FIG. 45A, FIG. 45B, FIG. 46A, FIG. 46B, FIG. 47A and FIG. 47B depict stages of the pump cycle of the fluid metering system according to the embodiment of FIG. 40.

The drawings are not to scale and some features are omitted in the different views for clarity.

DETAILED DESCRIPTION OF THE INVENTION

In each of the embodiments of the invention described below, a drive piston and a floating piston are oriented axially in a pump housing and the relative position of the pistons defines a pump volume V. The "axial direction" means along the longitudinal axis of the pump housing and/or one of the pistons. The pump volume is alternately expanded, which creates negative pressure to draw fluid from a reservoir through a first aperture into the pump volume, and compressed, to deliver the fluid through a second aperture to a cannula line. The pump volume may be sized according to the dosage to be delivered by the pump, in a range of 0.1 µl to 50 µl, for example. In the exemplary embodiments the pump volume is about 5.0 µl, designed so that two complete pump cycles delivers a unit of insulin at the customary U.S. concentration. In many embodiments, the discharge stroke empties the entire pump volume contents. It is also possible to increment the discharge stroke to provide for smaller dosage increments.

Figure 1:
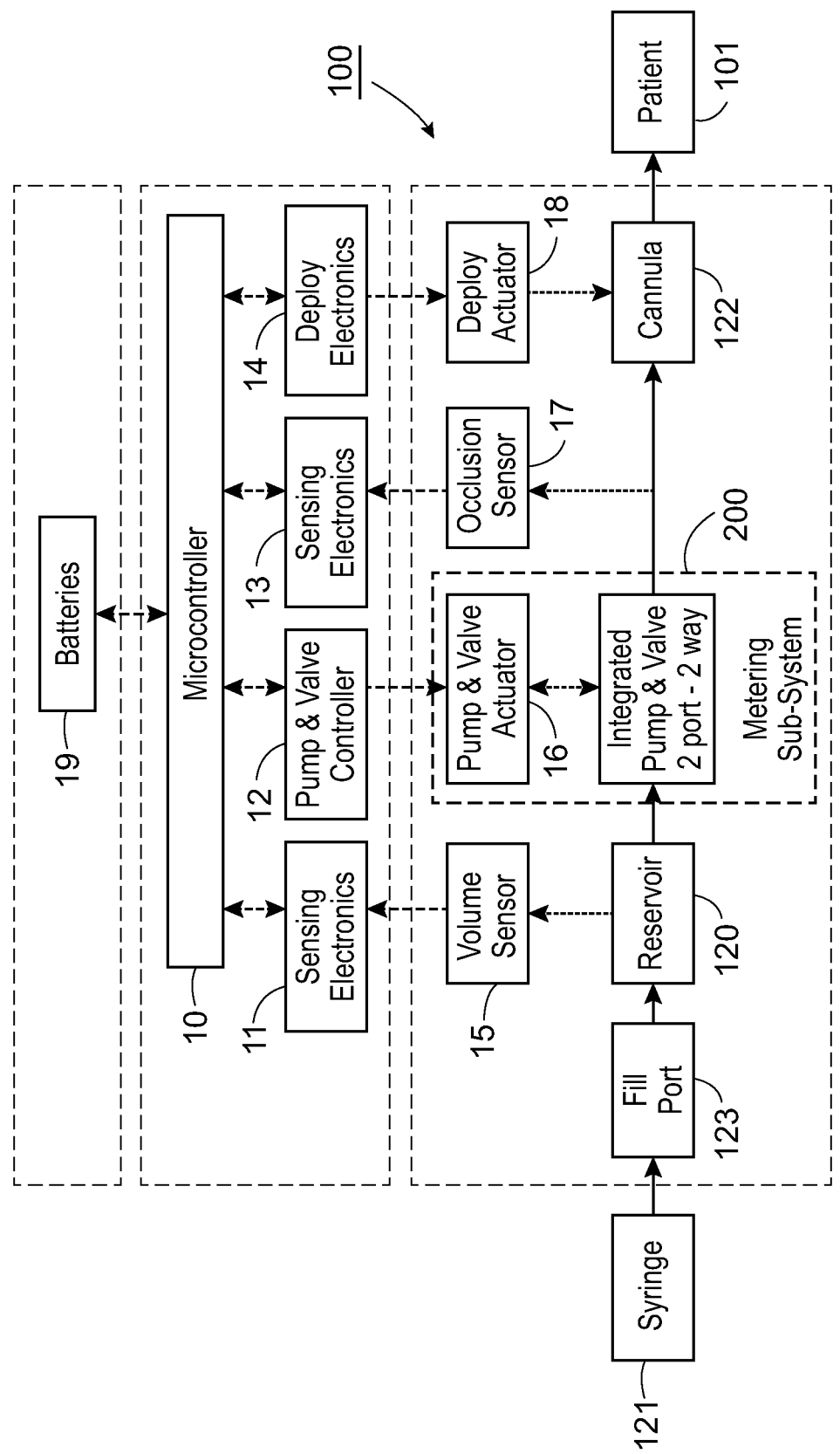
FIG. 1 is a schematic overview of the infusion pump according to the invention, including the fluidics and fluid metering subsystems.

FIG. 1 provides a schematic overview of a fluid delivery system 100, comprising a reservoir 120 in fluid communication with metering subsystem 200 for drawing a precise amount of fluid from the reservoir, and a cannula mechanism 122 for delivering medication to the user 101. The metering subsystem (the pump) is preferably lightweight and wearable. The cannula mechanism 122 may be connected to the infusion site by an infusion set comprising tubing and a patch, or alternatively a cannula insertion mechanism maybe incorporated into a housing within the metering subsystem 200. Although the invention is not limited to any specific reservoir embodiment, the reservoir 120 is preferably flexible and is not engaged with a plunger and lead screw, as is the case with many prior art insulin pumps. The flexible reservoir does not have an internal actuator mechanism for delivering fluid, which permits the overall pump to have a smaller footprint and more compact design. The reservoir may be filled via a fill port 123 by syringe 121, for example, or a prefilled reservoir or cartridge may be used.

Microcontroller 10 is provided in the form of a printed circuit board (PCB) which interfaces with sensors and circuitry 11, 12, 13, 14, 15, 17 and with actuators 16 and 18, to control the pump and cannula. Power is provided by one or more batteries 19 in the housing. Audible feedback and visual display and user operable controls (not shown) may be provided on the unit, operatively connected to the PCB, or on a remote programming unit, to set dosage, deploy the cannula, initiate infusion and deliver bolus dosages, as is known in the prior art.

Figure 2:
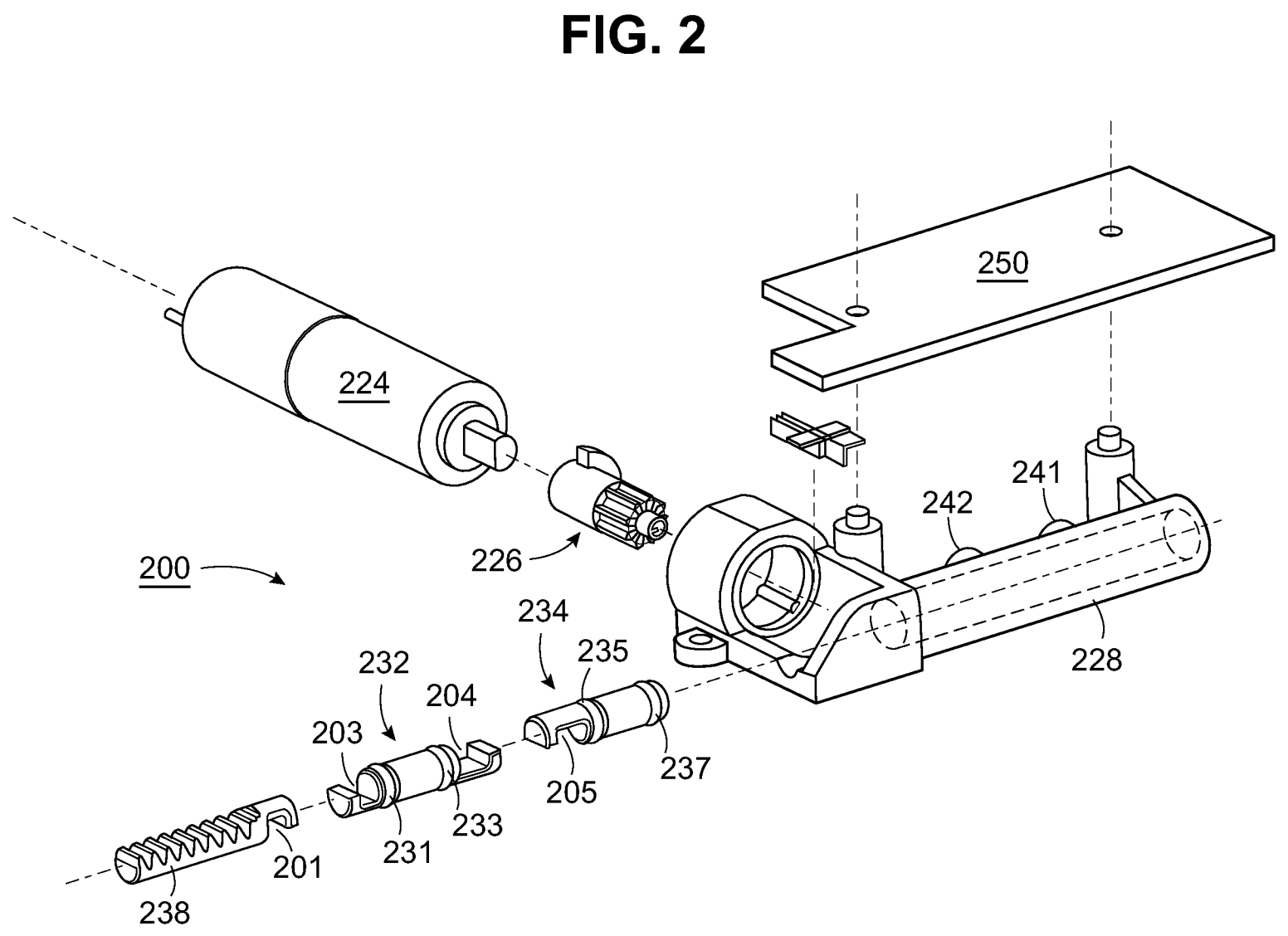
Figure 3:
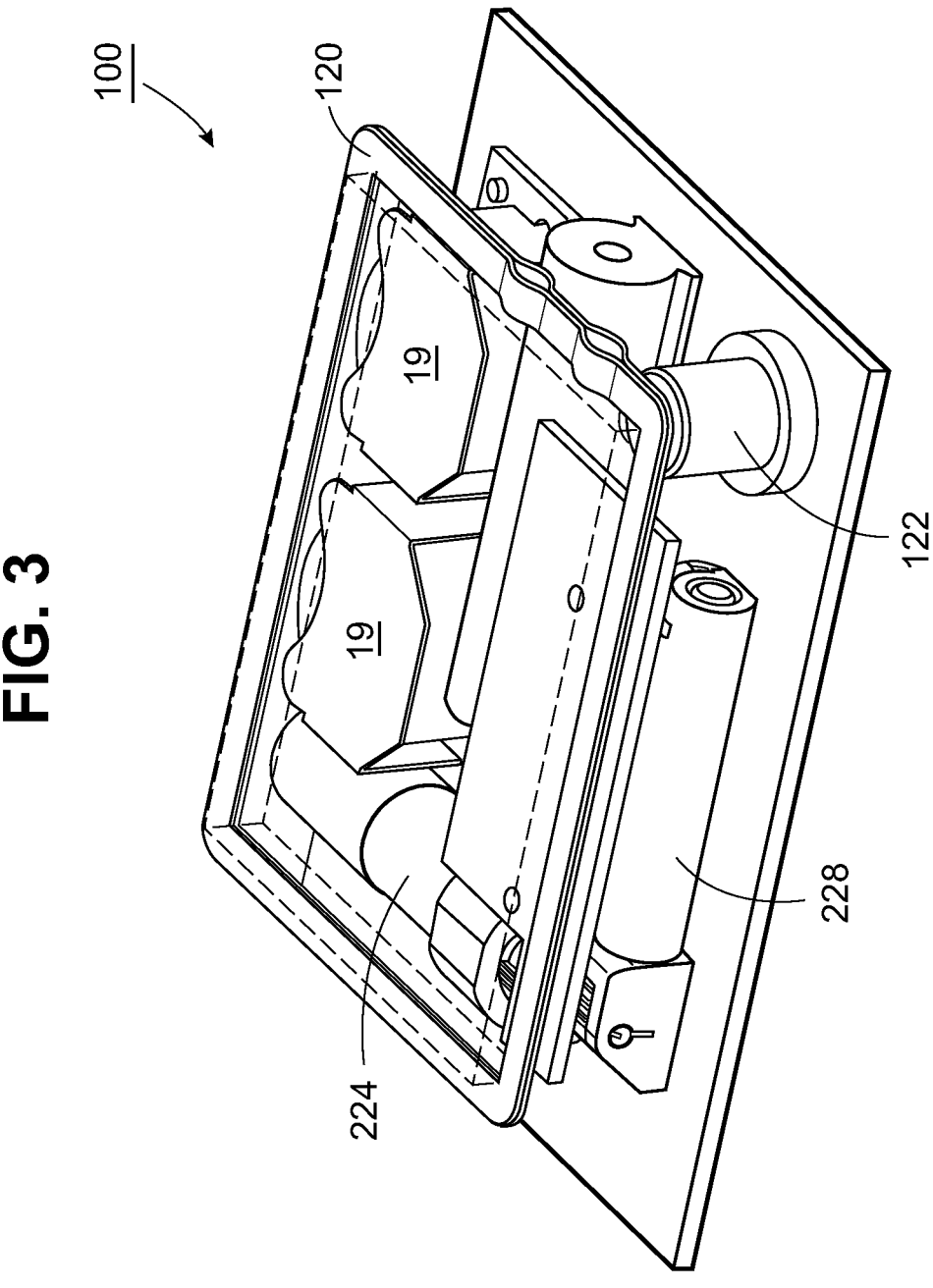
FIG. 3 is a view of an assembled infusion pump according to a first exemplary embodiment of the invention.

The components of the metering subsystem 200 according to one embodiment of the invention are depicted in an exploded view in FIG. 2 and assembled in FIG. 3. The metering subsystem 200 includes motor 224 and gear 226 for driving a positive displacement pump. The pump includes a tubular pump housing 228, and a multi-segment piston aligned axially within the pump housing. In the embodiment of FIG. 2 and FIG. 3, a drive piston 232 and a floating piston 234 are axially oriented within the pump housing and coupled to each other. The drive piston 232 and the floating piston 234 each have a pair of radially disposed seals 231, 233 and 235, 237 frictionally engaged with an internal surface of the tubular pump housing 228.

The pump stroke creates positive and negative pressure gradients within the fluid path to induce flow. Therefore, the seals must be frictionally engaged with the internal surface of the tubular pump housing 228 and sized to maintain positive and negative pressure in the pump volume and also to ensure that positive and negative pressure does not move the pistons until they are engaged in the pump stroke. In the embodiment shown, seals 231, 233, 235 and 237 are radially positioned elastomeric O-rings. However, seals could be molded directly onto the pistons or alternative seal systems may be adapted to perform the same function, such as quad rings, or polytretrafluoroethylene (TEFLON®) or polyethylene lip seals. In general, the components of the metering subsystem are made of a rigid medical grade plastic, such as acrylonitrile butadiene styrene (ABS), while liquid silicone rubber (LSR) with shore A hardness between 20 and 50 is used for the seals. If desired, the LSR seals may be molded directly onto the hard plastic substrates, in which case the substrate parts should be made of a plastic material with a higher softening temperature such as polyetherimide (PEI) or polysulfone (PS).

The disclosure refers to a "floating piston" in the various embodiments. This term is used for convenience only. "Floating" in this context simply means that the element is not directly coupled to the motor, but rather has some independent movement as a result of the frictional engagement of the radial seals with the internal surface of the tubular pump housing. The term "piston" simply refers to the piston-like arrangement in the tubular pump housing, and is not meant to convey how liquid is compressed in the pump volume space. Likewise, a piston need not be moved to be translated with respect to another piston or element.

In the embodiment shown, pairs of seals 231, 233 and 235, 237 create fluid control valves actively shuttled between the reservoir port 241 and cannula port 242 at each end of the pump stroke to alternately block and open the ports to ensure that fluid flow is unidirectional (from the reservoir 120 to the patient 101) and that there is no possibility of flow from the patient to the reservoir.

Figures 4, 5:
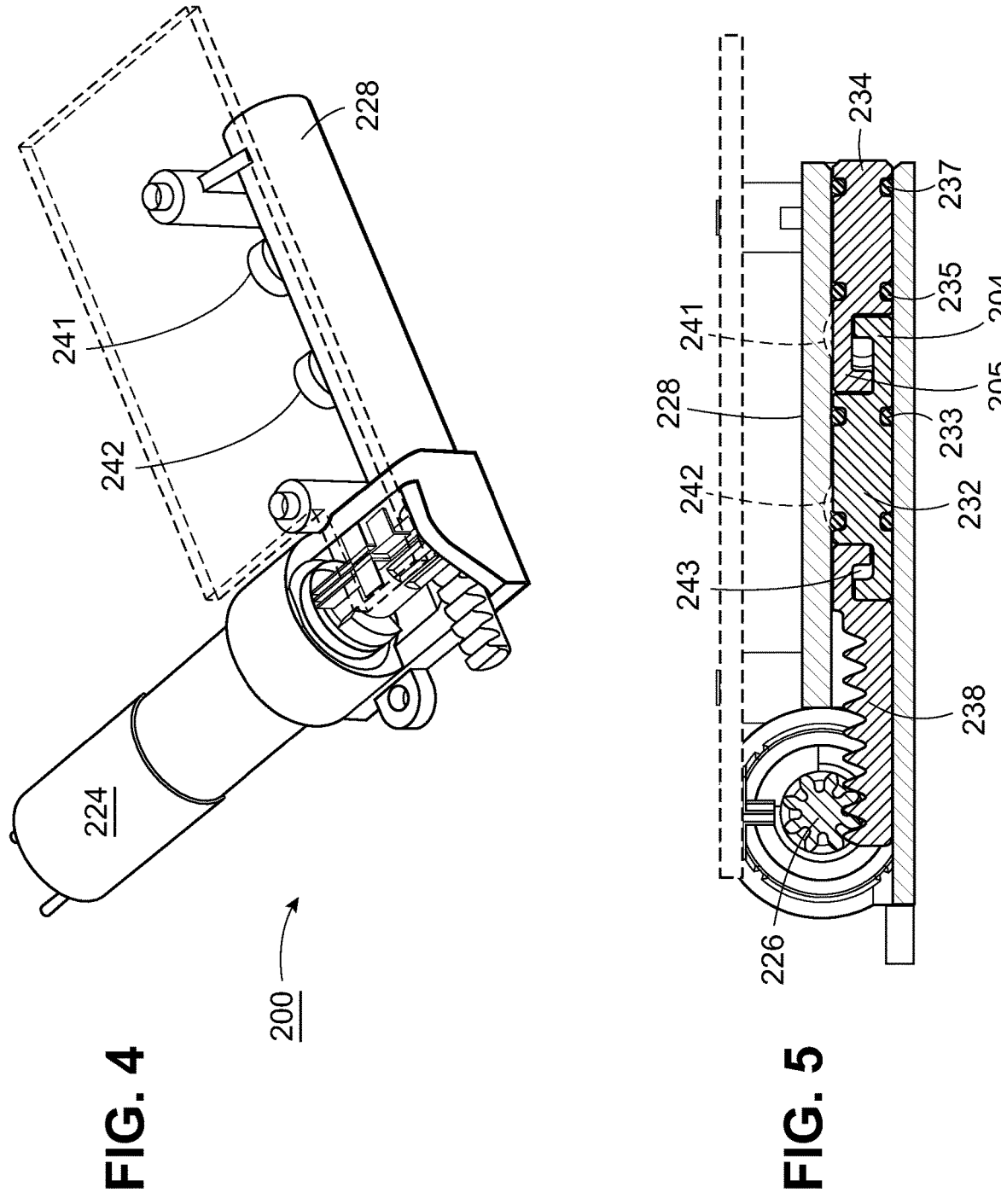
FIG. 4 is a perspective view of the assembled fluid metering system.
FIG. 5 is a side cross sectional view of the assembled fluid metering system of FIG. 4.

As seen in the cross-sectional view of FIG. 5, the piston assembly comprises drive rack 238, a drive piston, 232 and a floating piston 234 which are coupled to each other. Although variations may be practiced to couple the piston segments, in the embodiment shown, the piston segments are attached with a series of hooks, including a first hook 205 on a first end of the floating piston coupled to a second hook 204 on the end of the drive piston axially opposite the first end of the floating piston 234. A gap between the first hook 205 and the second hook 204 permits defined axial movement of the floating piston 234 with respect to the drive piston 232. A third hook 203 on the opposite end of the drive piston 232 is coupled to a fourth hook 201 on the drive rack. A gap between the third hook 203 and the fourth hook 201 permits defined axial movement between the drive rack 228 and the drive piston 232 which may be used to provide a stepwise increase in the load on the motor during the pump cycle, as described below.

In the embodiment shown, the pumping volume is located in the interface between drive piston 232 and floating piston 234 between seals 233 and 235, and the pump volume space is defined by the relative positions of drive piston 232 and floating piston 234. Prior to initiation of the intake stroke, reservoir port 241 is positioned between radial seals 233 and 235 on the respective coupled ends of the drive piston and floating piston, and the gap area between hooks 205 and 204 is open to reservoir port 241. The cannula port 242 on the other hand is closed by drive piston 232 in the initial state.

Figures 6A, 6B:
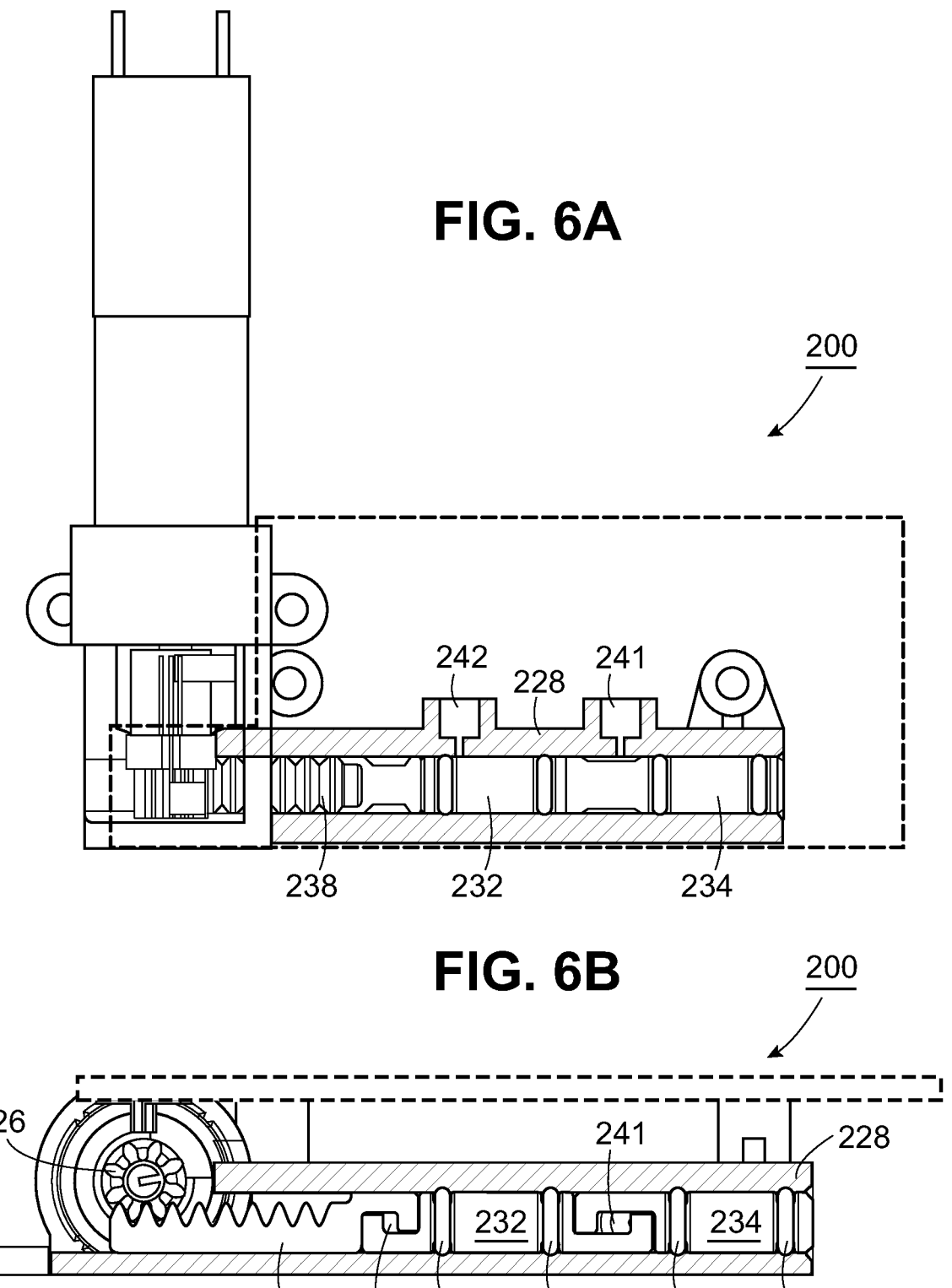
FIG. 6A is a top view of the assembled fluid metering system of FIG. 4 in an initial state prior to the start of the pump cycle.
FIG. 6B is a side cross sectional view of the assembled fluid metering system in the initial state of FIG. 6A.

The initial state of the pump prior to initiation of the pump cycle is depicted in FIG. 6A. The motor 224 is engaged to the gear 226 and the gear is engaged to a drive rack 238 to translate the floating piston 234 axially with respect to drive piston 232. The engagement of L-shaped hook 201 on drive rack 238 with the L-shaped hook 203 on drive piston leaves a coupling gap 243 which allows the motor to start with a light load, closing the gap before engaging the drive piston 232. The gap between hooks 204 and 205 on drive piston 232 and floating piston 234 allows the pump volume to expand and allows the cannula port 242 and reservoir port 241 to access the pump volume at different stages of the pump cycle.

The tubular positive displacement pump according to the invention provides a short tolerance loop for dose accuracy, dependent on the readily measurable dimensions of the tubular pump housing 228 inside diameter and the hook features of pistons 232 and 234. The dosage is not directly calibrated to the turning of motor 224, so that the pistons may over-travel within the pump housing without affecting dose accuracy. Although a DC gear motor 224 powered by a battery 19 is depicted in FIG. 3, other motor systems may be adapted for use with the invention, such as a solenoid, nitinol (nickel-titanium alloy) wire motor, voice coil actuator motor, piezoelectric motor, and wax motor.

In the initial state depicted in FIGS. 6A and 6B, the drive rack 238 is fully extended into the pump housing 228 so that driven piston 232 blocks the cannula port 242. As seen in the cross sectional view of FIG. 6B, the pump volume space between seal 233 of driven piston 232 and seal 235 of the floating piston is fully collapsed and open to the reservoir port 241.

Figures 7A, 7B:
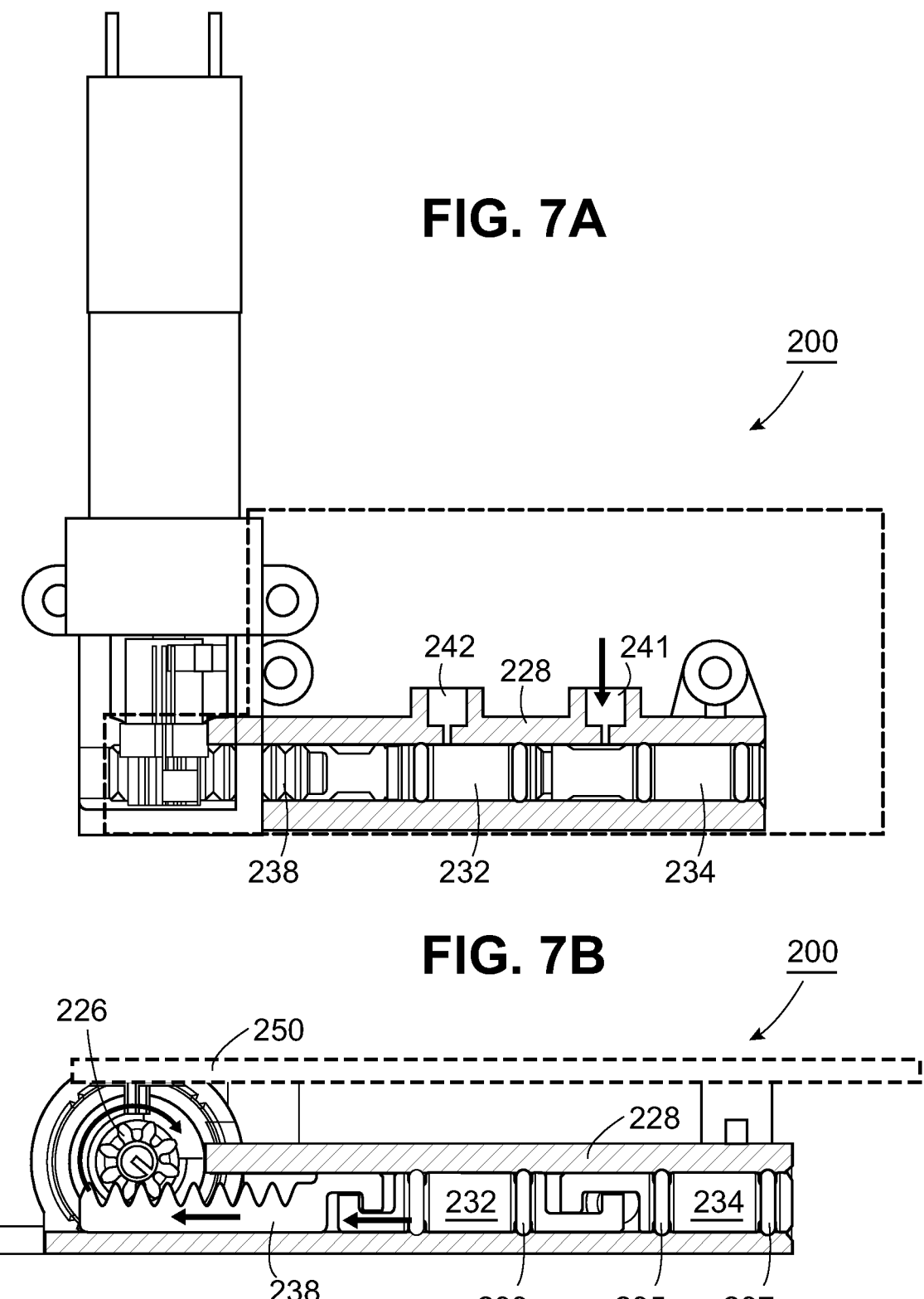
FIG. 7A is a top view of the assembled fluid metering system of FIG. 4 during the intake stroke of the pump cycle.
FIG. 7B is a side cross sectional view of the assembled fluid metering system in the state of FIG. 7A.

FIG. 7A and the corresponding cross sectional view of FIG. 7B show metering system 200 during an intake stroke. The intake stroke is designed so that a stepwise increasing load is applied to the motor, which is advantageous to motor efficiency and battery life. The coupling gap 243 (shown in FIG. 6B) allows the motor to start under light load, minimizing start up currents which adversely affect battery life. In the initial stage of the intake stroke, drive rack 238 is translated axially to close the gap between drive rack 238 and drive piston 232 as a result of clockwise turning of gear 226. When the gap between the drive rack and the piston is closed, drive rack 238 directly engages drive piston 232. In this stage of the intake stroke, floating piston 234 is stationary while the pump volume expands, drawing fluid through reservoir port 241 into the pump volume. During the intake stroke, friction between seals 235, 237 on floating piston 234 and the internal diameter of pump housing 228 must be high enough to ensure that negative intake pressure acting on the face of floating piston 234 does not move this piston before the intake stroke is complete.

Figures 8A, 8B:
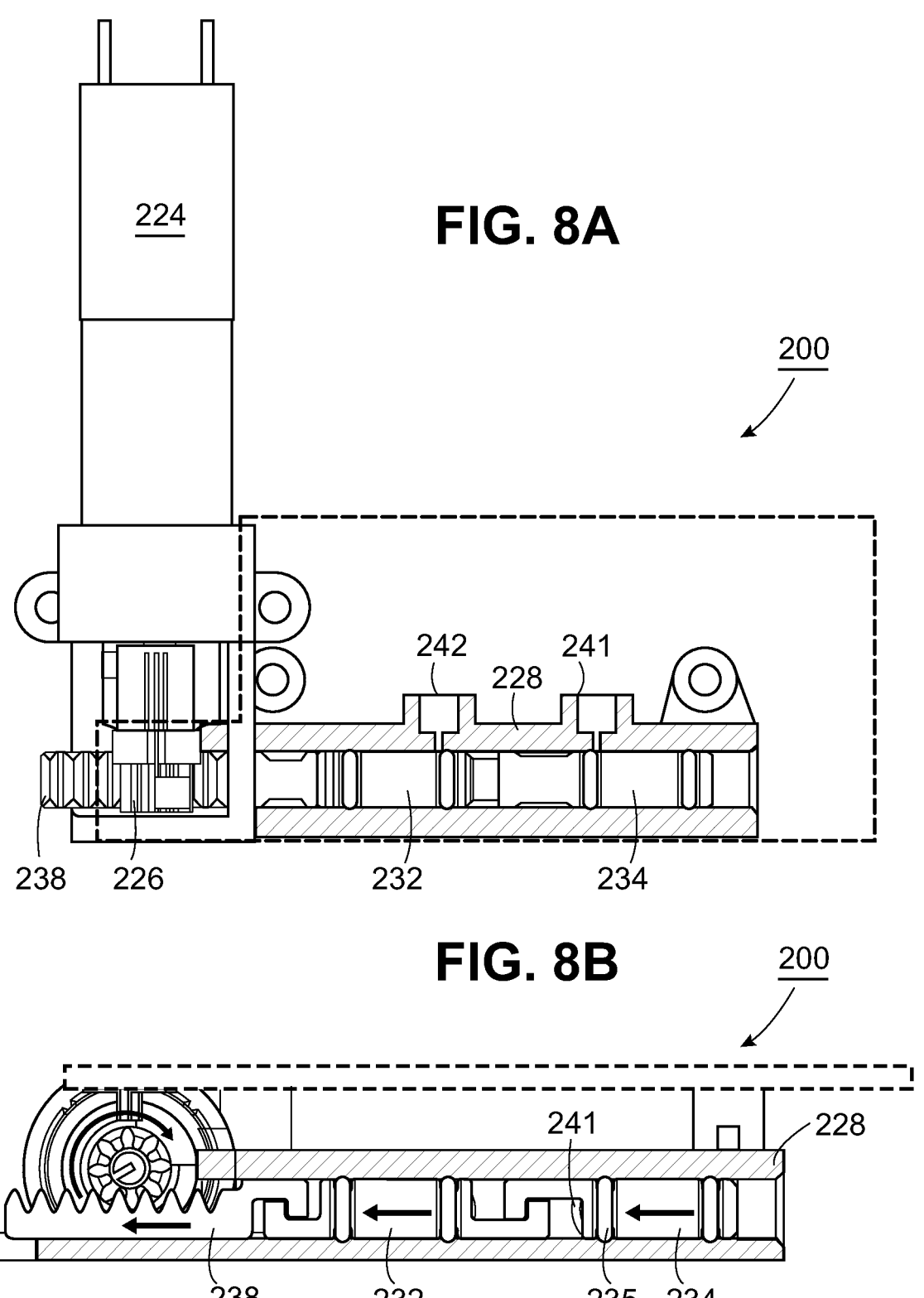
FIG. 8A is a top view of the assembled fluid metering system of FIG. 4 during a valve state change of the pump cycle.
FIG. 8B is a side cross sectional view of the assembled fluid metering system in the state of FIG. 8A.

FIG. 8A and FIG. 8B depict metering system 200 after the intake stroke, when the pump volume is fully expanded. The movement of drive rack 238, drive piston 232 and floating piston 234 is depicted with arrows. During this stage of the pump cycle, the floating piston 234 begins to move under the urging of motor 224 and the continued clockwise rotation of gear 226. Reservoir inlet 241 is blocked as seal 235 on floating piston 234 passes over the inlet orifice for reservoir port to change the valve state. The blocking and opening of the reservoir port and cannula port follows a specific sequence. During the valve change state after the intake stroke, the reservoir port is blocked first. This is followed by an intermediate state in which both ports are blocked. Further axial movement of the two pistons then opens the cannula port. The system is designed to have an intermediate state to ensure that the two seals do not pass over the side holes at the same time. The sequenced valve transition minimizes the likelihood of backflow as the seal moves over the port when infusing at high back pressure.

Figures 9A, 9B:
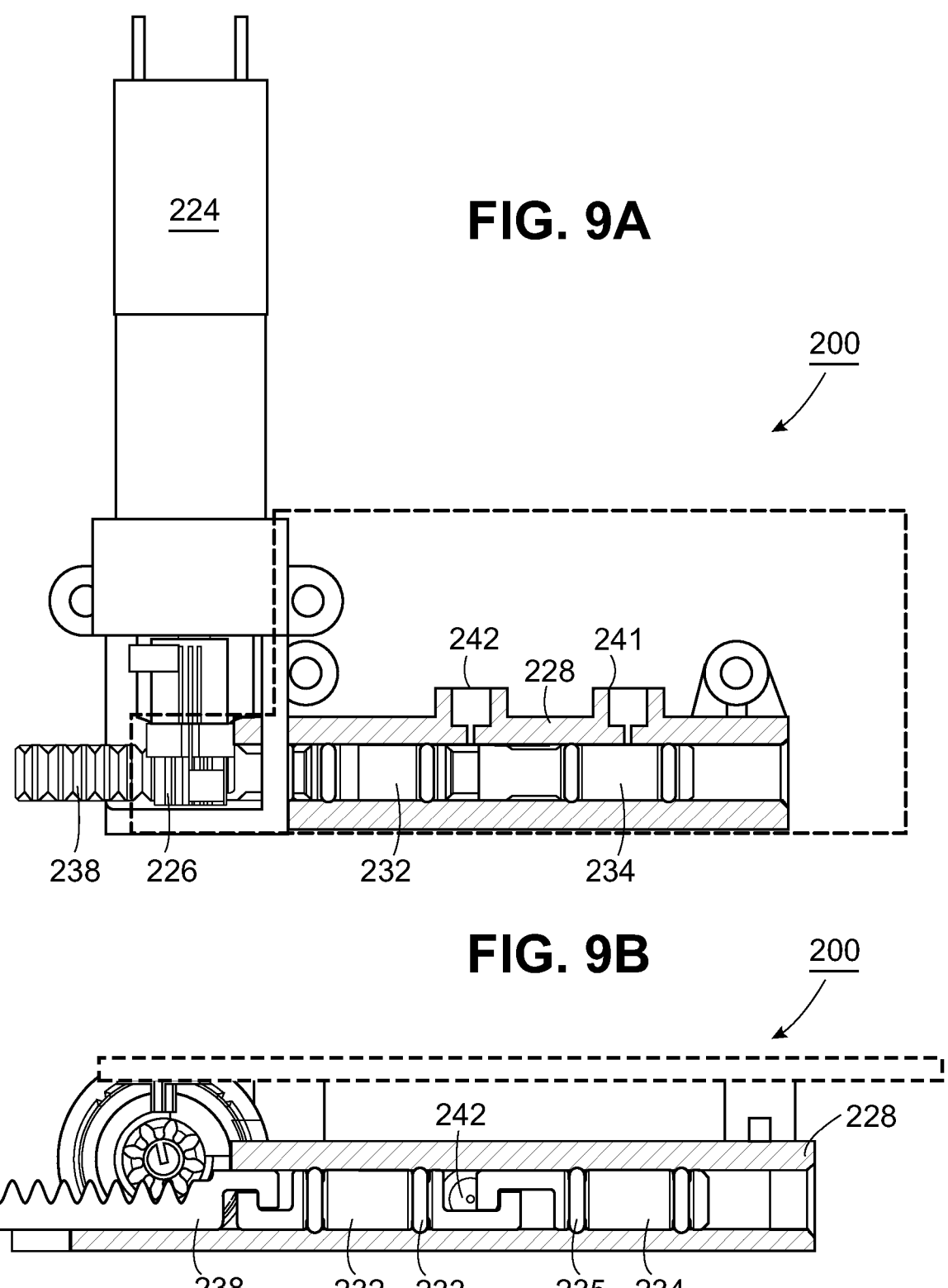
FIG. 9A is a top view of the assembled fluid metering system of FIG. 4 with the pump volume in a fully expanded state.
FIG. 9B is a side cross sectional view of the assembled fluid metering system in the state of FIG. 9A.

FIG. 9A and FIG. 9B show metering system 200 in its fully retracted state, with drive rack 238 fully retracted from tubular pump housing 228 and cannula port 242 opened to the expanded pump volume between seals 233 and 235. In this position, reservoir port 241 is blocked by floating piston 234.

Figures 10A, 10B:
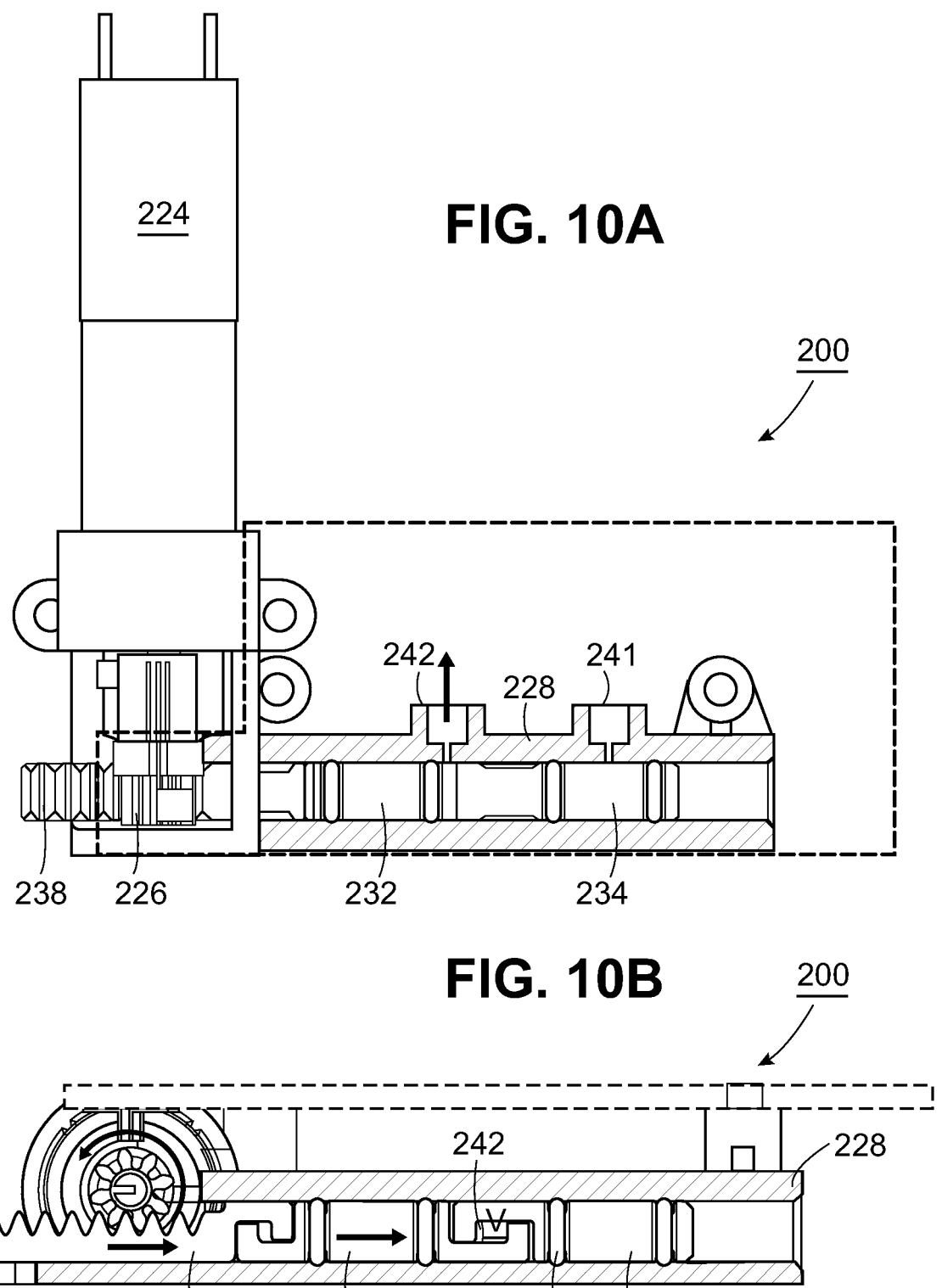
FIG. 10A is a top view of the assembled fluid metering system of FIG. 4 during the discharge stroke of the pump cycle.
FIG. 10B is a side cross sectional view of the assembled fluid metering system in the state of FIG. 10A.

During the initial phase of the discharge stroke, depicted in FIG. 10A and FIG. 10B, motor 224 and gear 226 rotate in the opposite direction (counterclockwise), noted by arrows, so that drive rack 238 pushes drive piston 232 toward the floating piston 234, which initially remains stationary while pump volume V collapses and pushes fluid from the pump volume through cannula port 242. During the discharge stroke, friction between the seals on floating piston 234 and the internal surface of pump housing 228 must be high enough to ensure that positive pressure acting on the face of floating piston 234 does not move this piston before the discharge stroke is complete. As with the intake stroke, the discharge stroke is designed so that a stepwise increasing load is applied to the motor.

Figures 11A, 11B:
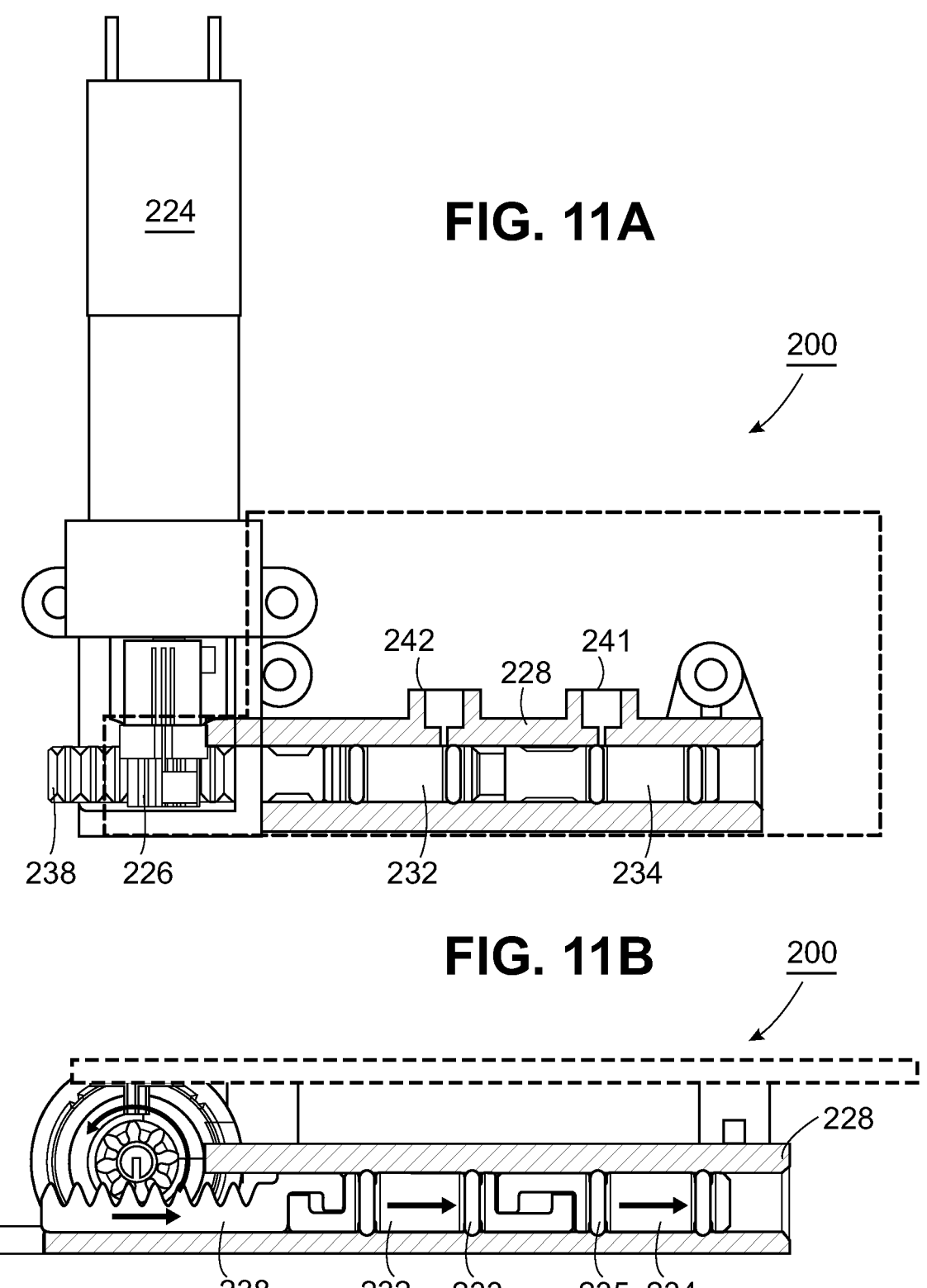
FIG. 11A is a top view of the assembled fluid metering system of FIG. 4 after the discharge stroke of the pump cycle with the pump volume fully collapsed and the valve changing state.
FIG. 11B is a side cross sectional view of the assembled fluid metering system in the state of FIG. 11A.
Figures 12A, 12B:
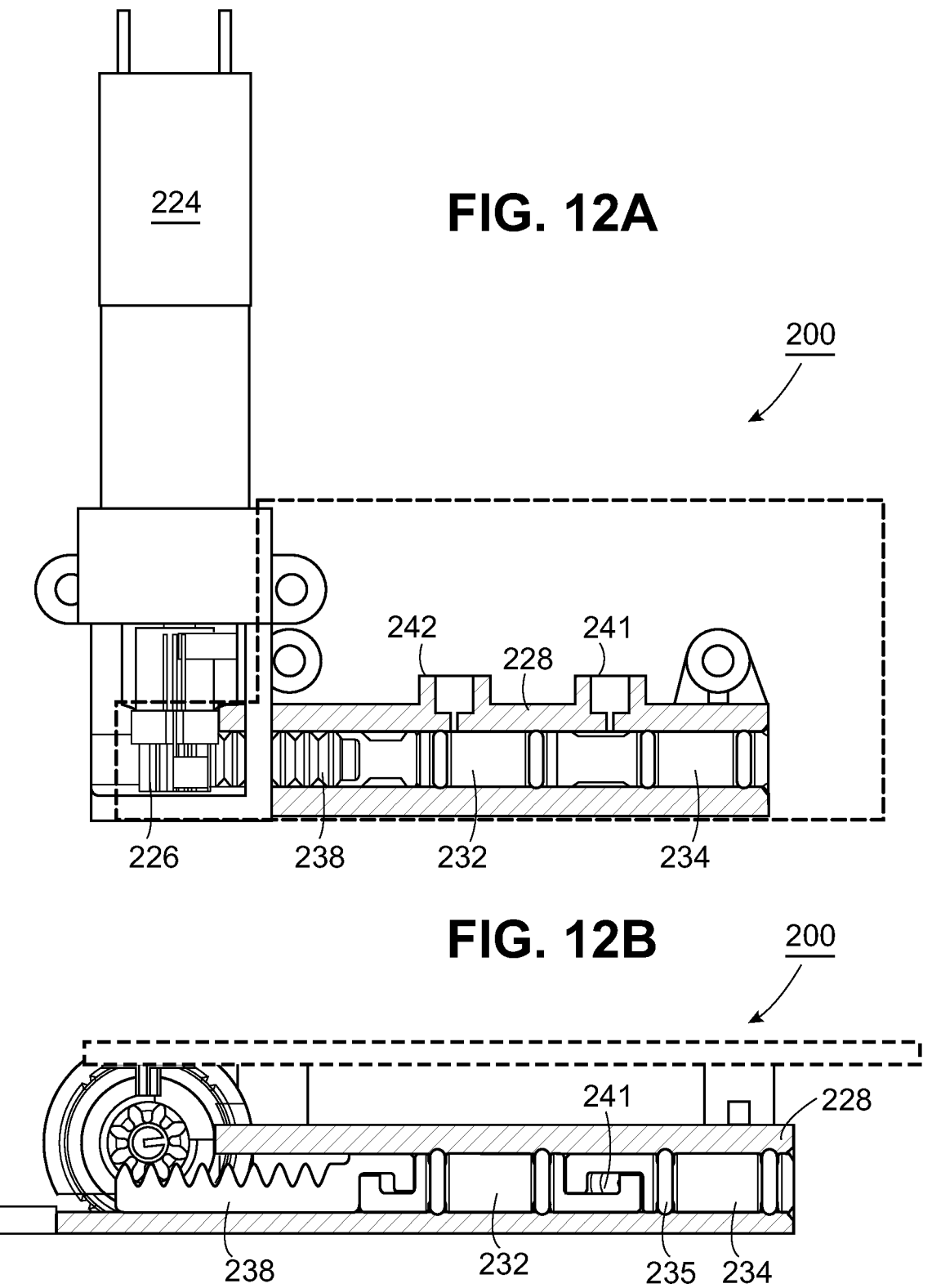
FIG. 12A and the corresponding cross section of FIG. 12B show the mechanism returned to the cycle start point.

FIG. 11A and FIG. 11B depict metering system 200 after the discharge stroke and during the valve state change. The pump volume is fully collapsed, and the force of motor 224 acts to move floating piston 234 in the direction indicated by the arrows in FIG. 11B. Cannula port 242 is first blocked, as the seal on drive piston 233 passes over the inlet aperture of cannula port 242. Reservoir port 241 is aligned with the collapsed pump volume, returning the piston segments to the starting position as shown in FIG. 12A and FIG. 12B.

Figure 13:
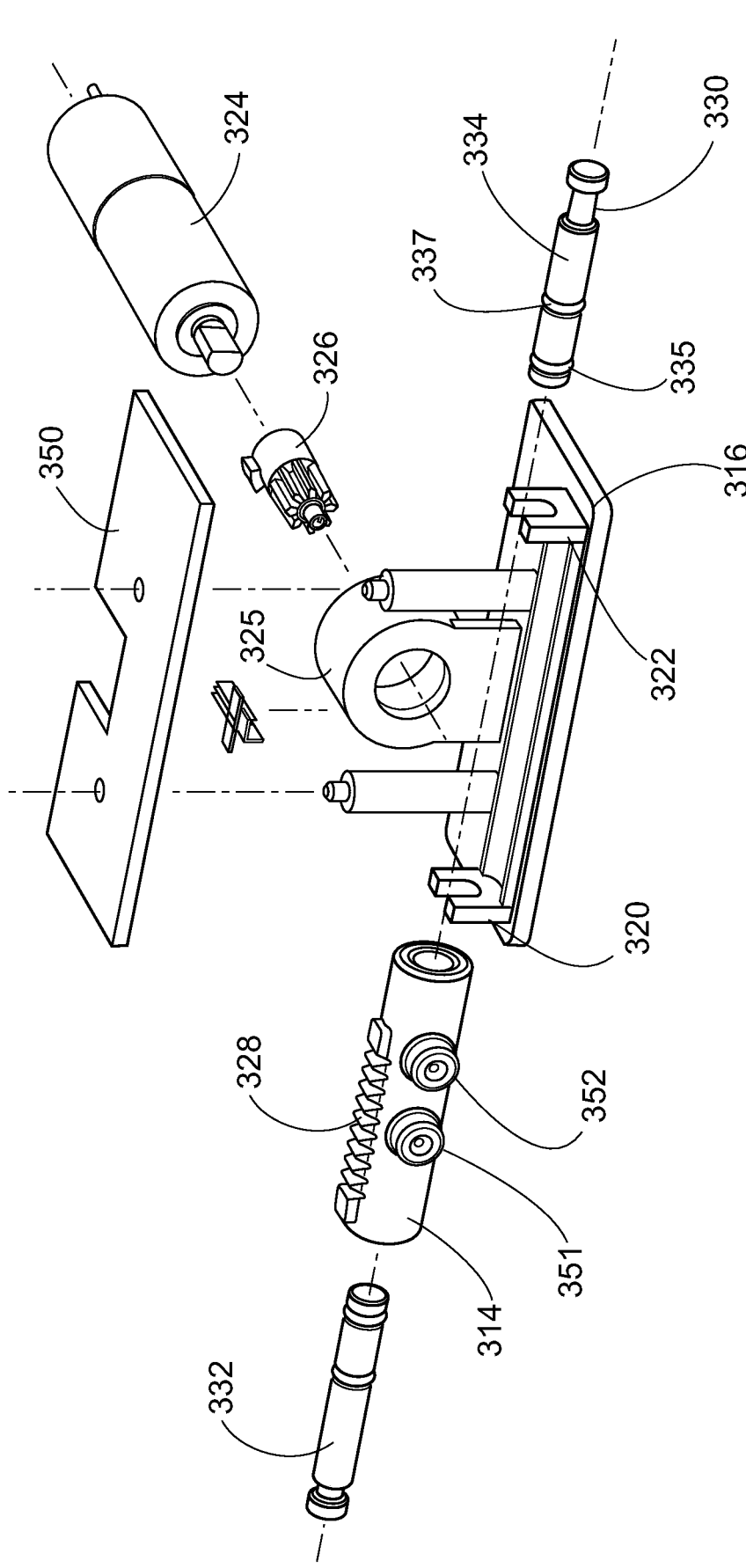
FIG. 13 is an exploded view of a fluid metering subsystem according to a second exemplary embodiment of the invention.

In a second alternative embodiment of the invention, the piston segments are independent, and are not coupled to each other. The position of the drive piston is fixed (referred to as the "fixed piston" in this embodiment), and the relative axial position of the piston segments is achieved by translating the pump housing. In this embodiment, shown in an exploded view in FIG. 13, and assembled in FIG. 13A, DC motor 324 and pinion gear 326 drive a pump housing 314 back and forth in a cradle 316. For this purpose, the drive rack 328 is incorporated on the top of pump housing 314. Fixed piston 332 is rigidly secured to the cradle 316 via a first keying rib 320 and does not move during the pumping cycle. Floating piston 334 translates back and forth relative to the fixed piston due to axial clearance between groove 330 on the floating piston and a second keying rib 322 on cradle 316. The pump volume is formed between facing surfaces of fixed piston 332 and floating piston 334.

Figure 13A:
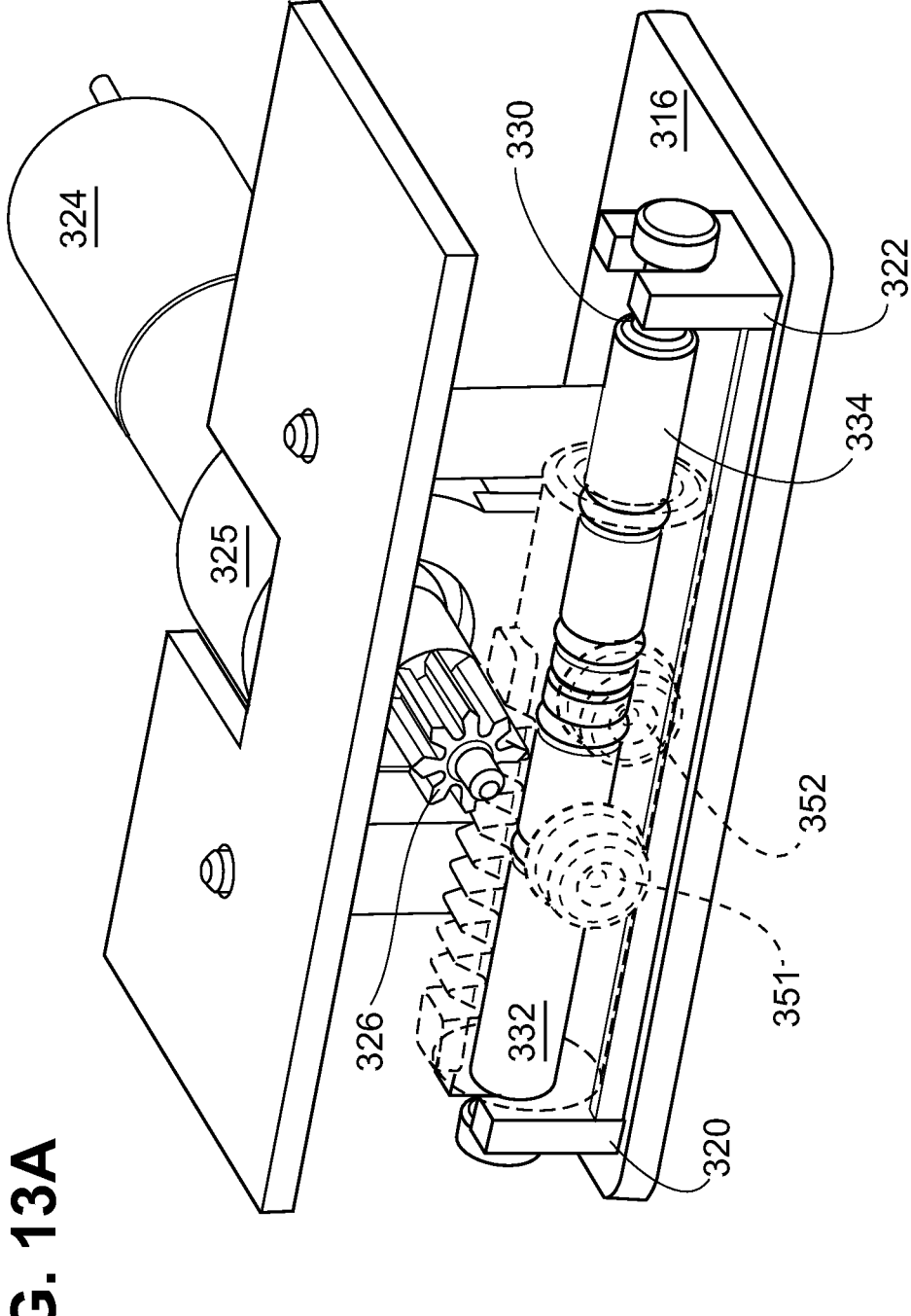
FIG. 13A is an assembled view of the fluid metering subsystem according to the embodiment of FIG. 13.

In the position shown in FIG. 13A, first axial end of the floating piston 334 approaches the end face of fixed piston 332. On the end of the floating piston opposite the first axial end, groove 330 in floating piston 334 is received in second keying rib 322 of cradle 316, such that the end of the groove 330 abuts the outside face of keying rib 322. FIG. 13A shows the assembly with motor 324 received in a housing 325 which, in the embodiment shown, is integral with the cradle 316 and located so that gear 326 is located about centrally to the housing. The relative displacement of the floating and fixed pistons 332, 334 determines the pump stroke. Friction between the internal surface of pump housing 314 and seals 335, 337 on floating piston 334 causes the floating piston to travel with pump housing 314 during the initial stage of the pump cycle when motor 324 drives pump housing 314 via gear 326 and drive rack 328. In the position shown in FIG. 13, the aperture of reservoir port 352 is aligned between floating piston 334 and the stationary drive piston 332.

Figure 14:
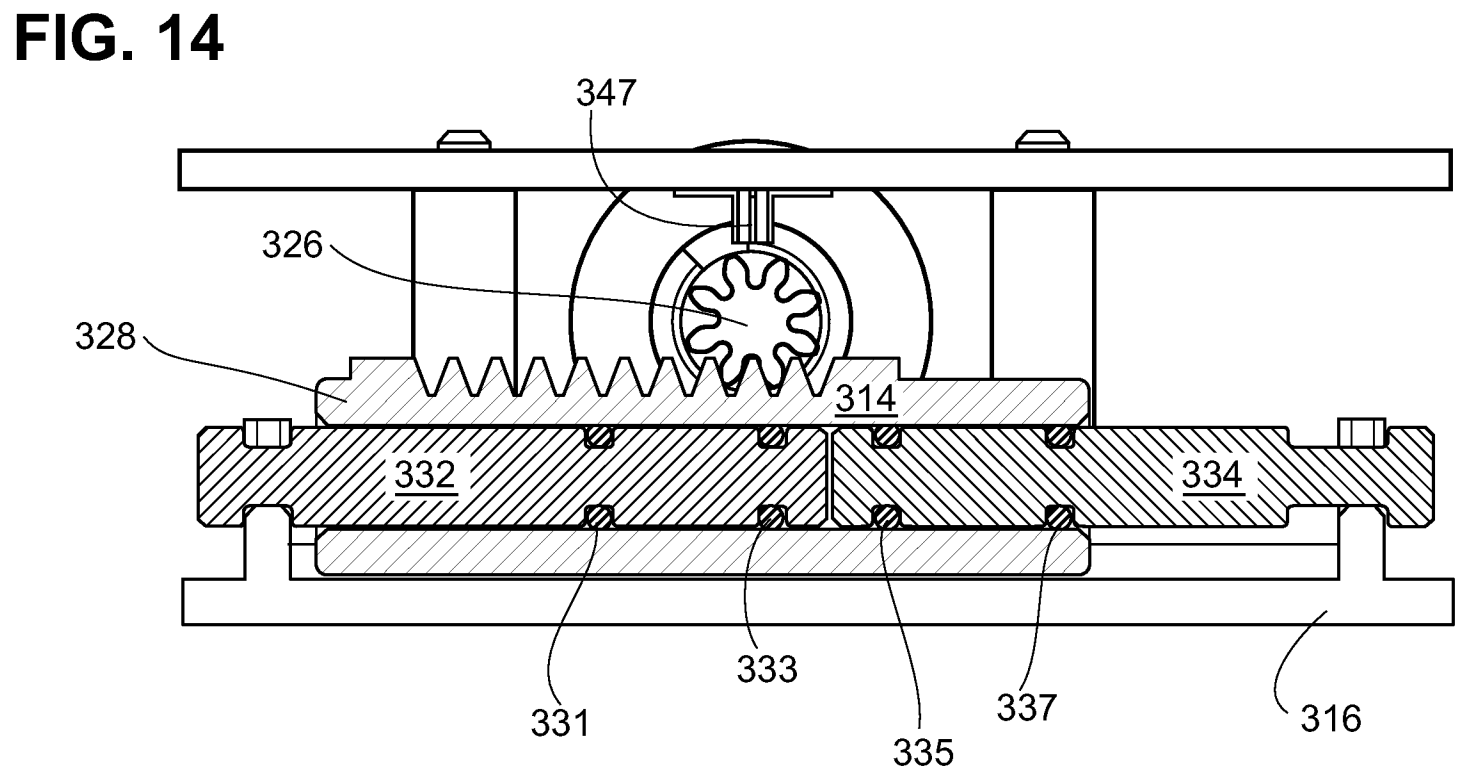
Figure 15:
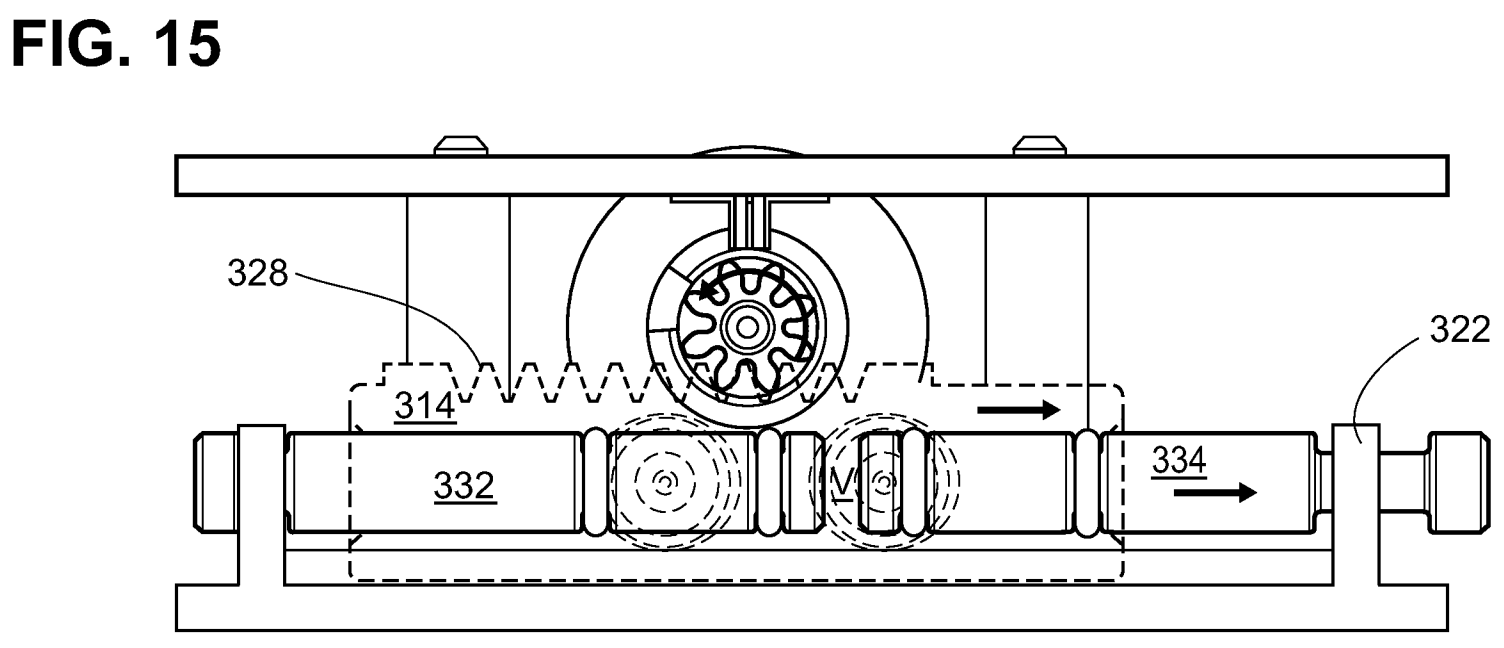

FIG. 14 shows the starting position for the pump cycle according to the second alternative embodiment in cross section. The travel limit sensor 347 is engaged and the pistons approach each other. As indicated by the arrows in FIG. 15, counterclockwise rotation of gear 326 (viewed down the shaft toward the motor) engages drive rack 328 and translates pump housing 314 in the direction of floating piston 334. In the initial stage of the intake stroke, floating piston 334 moves with the pump housing 314 due to friction between the seals and the interior surface of the pump housing and a pump volume V forms between the facing ends of the floating piston and fixed piston 332, 334. Fluid is drawn from the reservoir through reservoir port 352 due to negative pressure created in the pump volume V.

Figure 16:
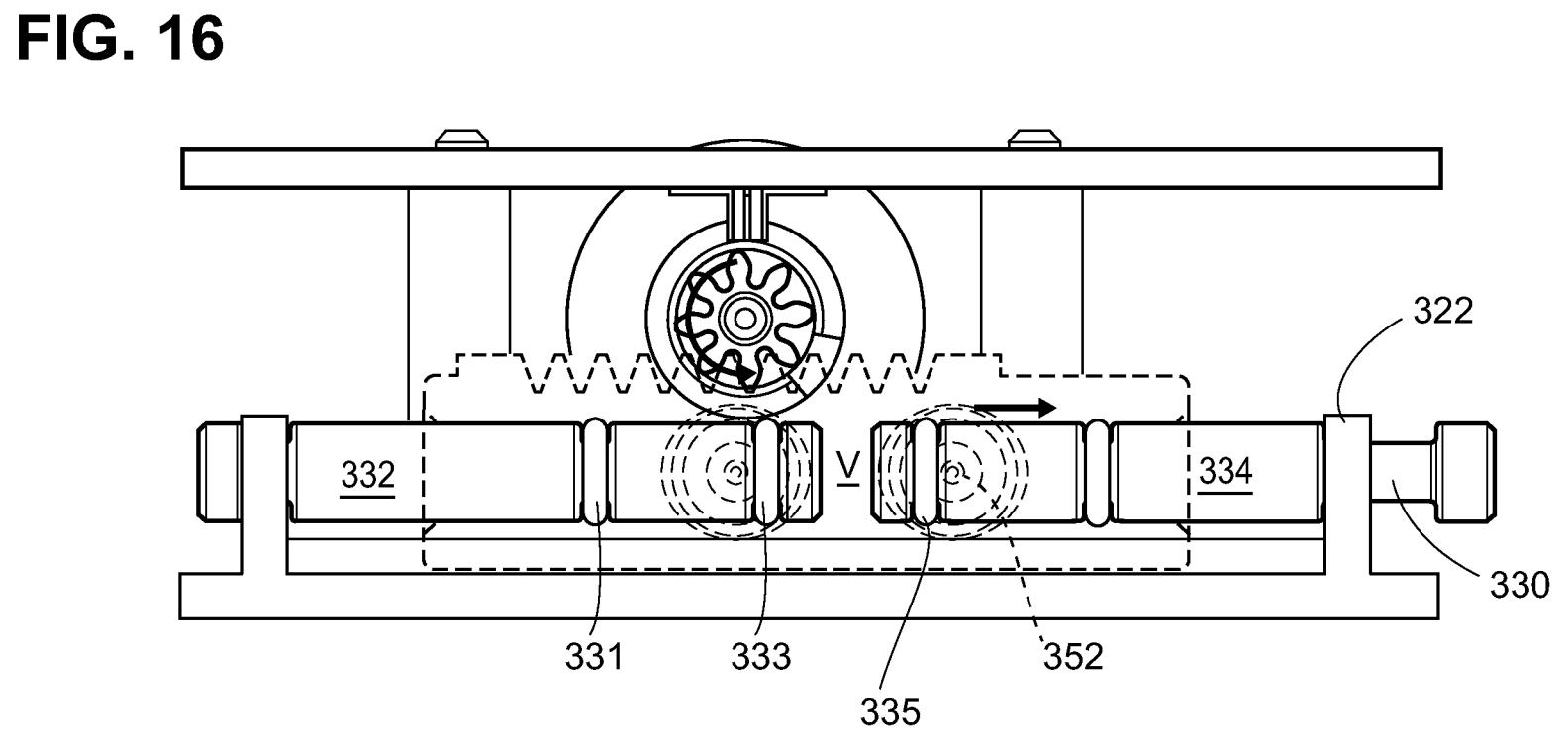
Figure 17:
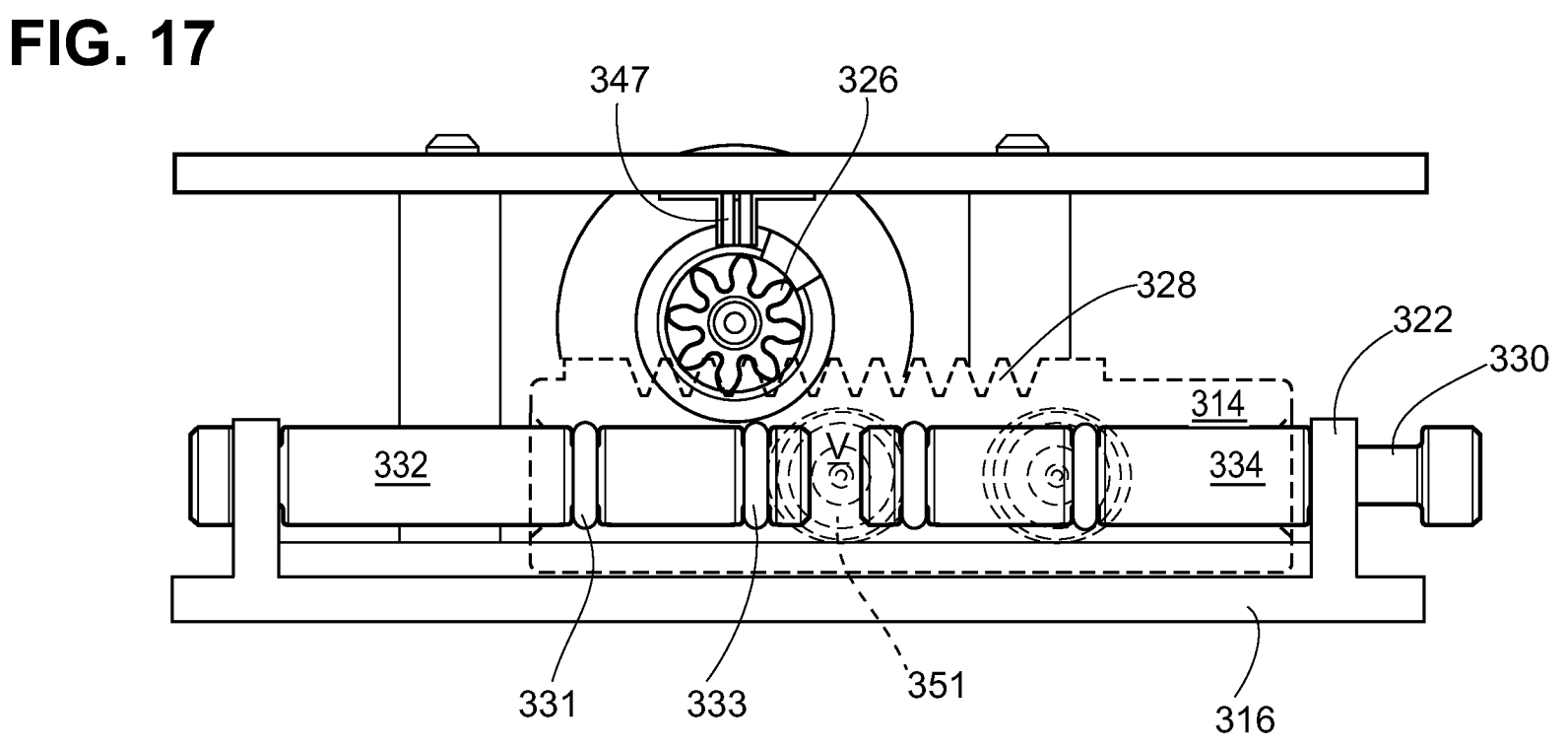

In the position shown in FIG. 16, after the intake stroke, the opposite side of groove 330 on floating piston 334 is stopped against keying rib 322 of cradle 316. In this state, the pump volume V is fully expanded, and pump housing 314 continues to move so that seal 335 on floating piston 334 passes over reservoir port 352. As shown in FIG. 17, cannula port 351 then passes over seal 333 of fixed piston 332, affording access by cannula port 351 to the expanded pump volume V between the two pistons 332, 334. Travel limit sensor 347 is triggered to reverse the direction of the motor for the discharge stroke.

Figure 18:
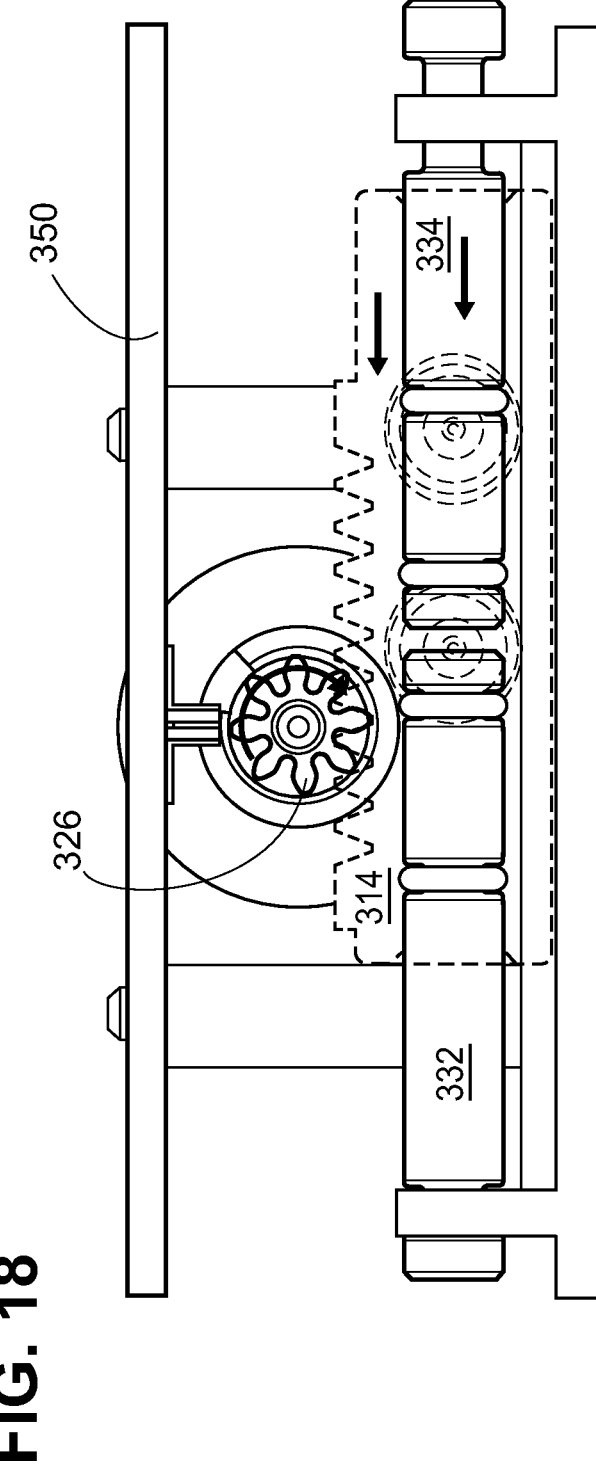
Figure 19:
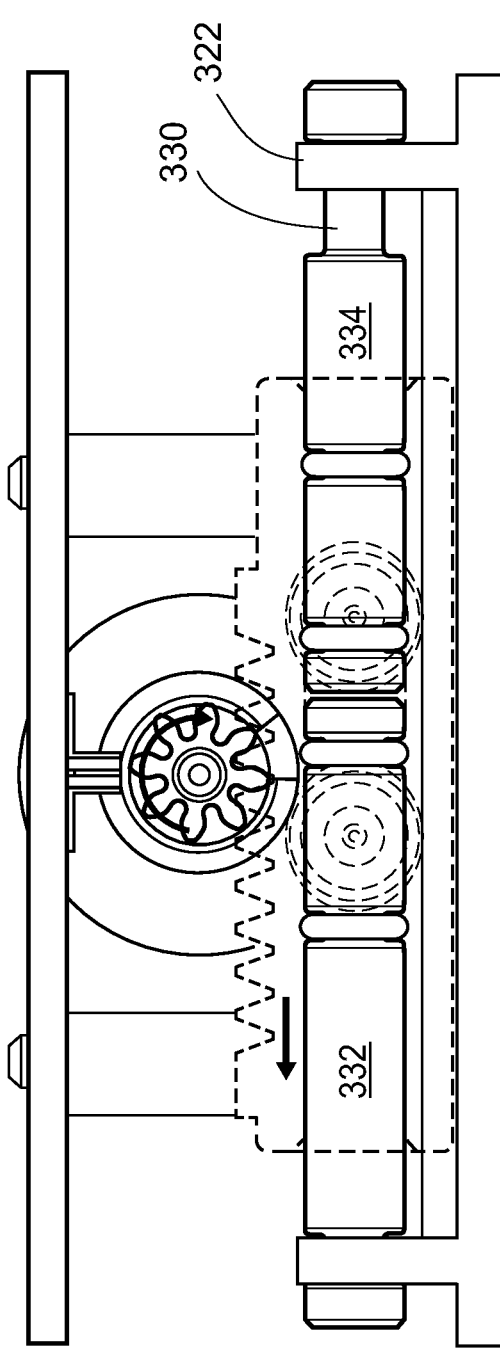
Figure 20:
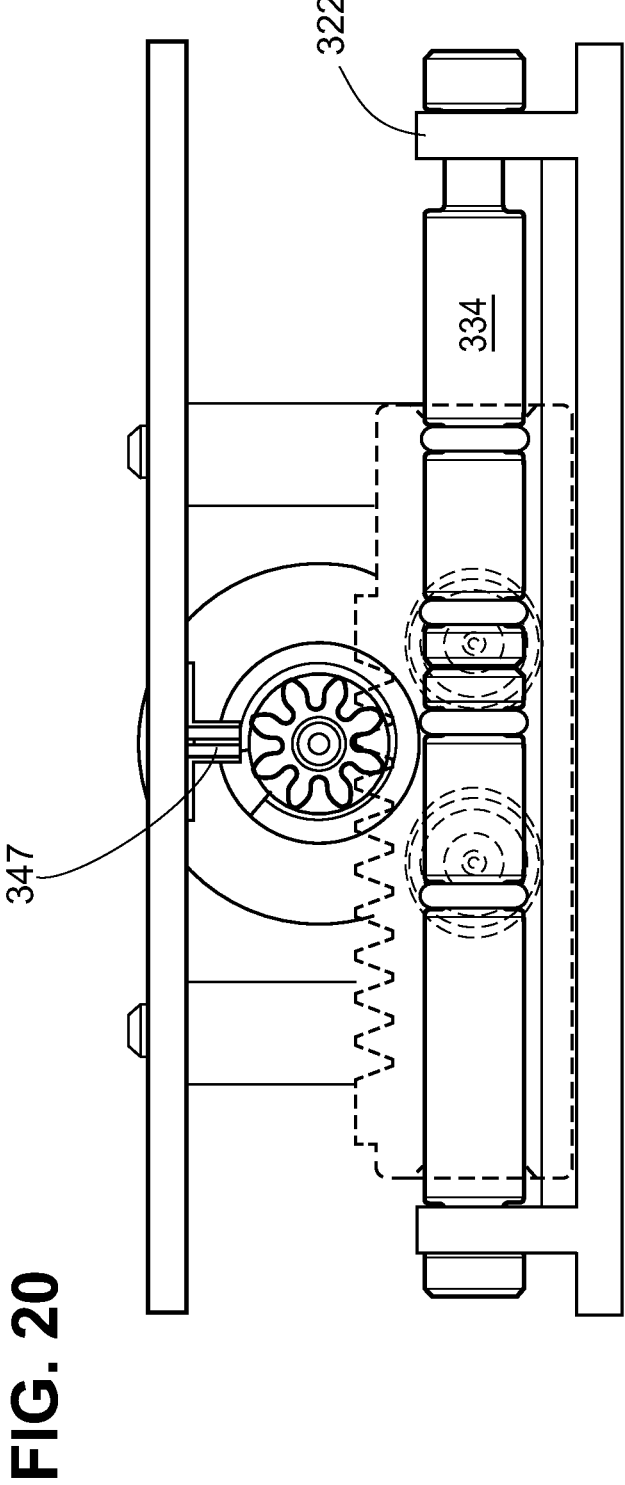
Figures 22, 23:
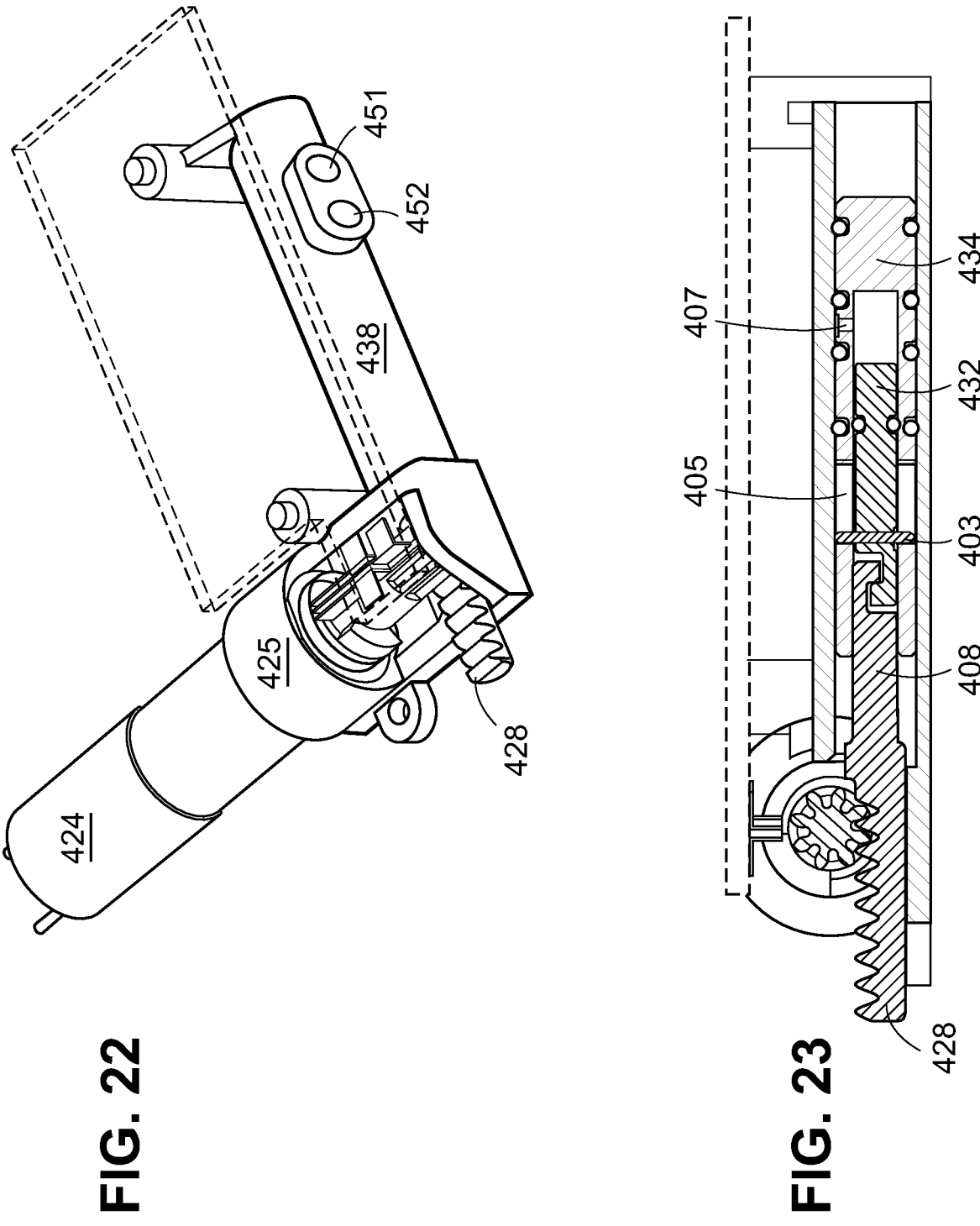
FIG. 22 is an assembled view of the embodiment of FIG. 21.
FIG. 23 is a side cross-sectional view of the embodiment of FIG. 21.

FIG. 18 shows the pump during the discharge stroke according to this embodiment of the invention. The motor shaft rotates in the opposite (clockwise) direction in the embodiment shown translating pump housing 314 and floating piston 334 in the direction of fixed piston 332, as shown by the arrows in FIG. 18. Pump volume V collapses, driving fluid down the cannula line through cannula port 351. During the discharge stroke, friction between seals on floating piston 334 and the internal diameter of pump housing 314 must be high enough to ensure that there is no relative motion between the floating piston 334 and the pump housing during this portion of the pump cycle. In FIG. 19 the pump cycle is completed, the end of groove 330 on floating piston reaches the key stop 322 to prevent further movement. In the position of FIG. 20, the travel sensor 347 is activated, and the device is at the starting position ready for another pump cycle.

In third and fourth embodiments of the invention, depicted in FIG. 21 through FIG. 39B, the pump volume is formed between a drive piston received within the bore of the floating piston (the floating piston in these embodiments is also referred to as a "spool.") As in the previous embodiments, the drive piston is driven by a motor, via gear and a drive rack to expand and compress a pump volume, which in this case is formed within the bore of the spool. Unlike the previous embodiments, only the seals on the spool are frictionally engaged with the interior of the pump housing. Positive and negative pressures in the pump volume space are maintained by a seal on the drive piston frictionally engaged with an internal surface of the bore.

Figure 21:
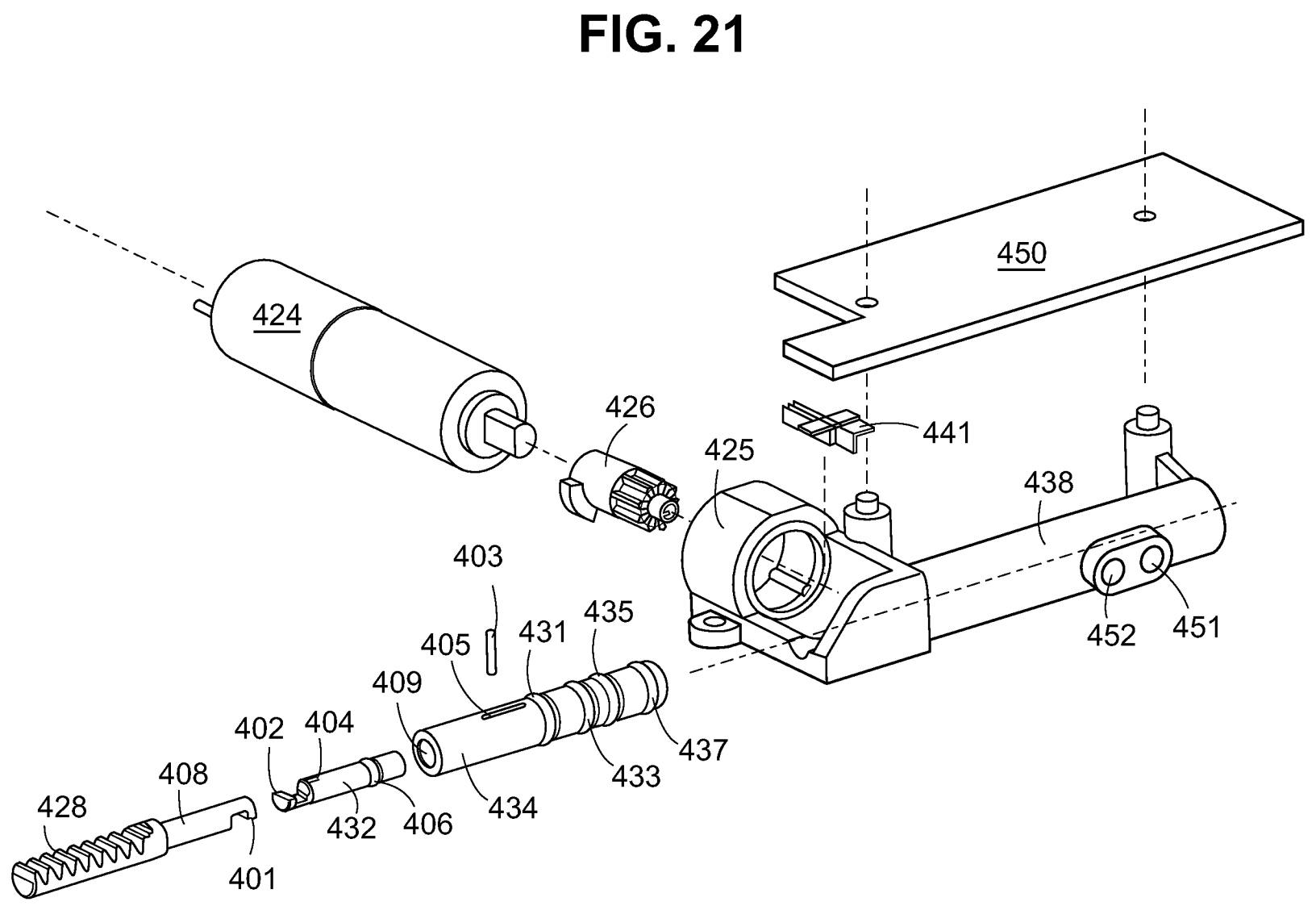

According to the third embodiment, as seen in the exploded view of FIG. 21, motor 424 is received in a housing 425, which may be integral with a tubular pump housing 438. As in the preceding embodiments, pinion gear 426 engages a drive rack 428 which is coupled to a drive piston 432. The coupling of drive rack 428 to drive piston 432, as well as the engagement of drive piston 432 in spool 434 may take various forms. In the specific embodiment of FIG. 21, drive piston 432 remains inside the bore of spool 434 during the pump cycle, and drive rack 428 includes an axial extension 408 which couples to drive piston 432 using cooperating hooks 401, 402, which are also received in pump housing 438. Drive piston 432 is coupled to spool 434 using a coupling pin 403 received in slot 405 in spool 434 and through a hole 404 in the drive piston. The axial length of slot 405 and the diameter of coupling pin 403 determine the freedom of movement of drive piston 432 inside the bore of spool 434 during the pump cycle.

Figures 24A, 24B:
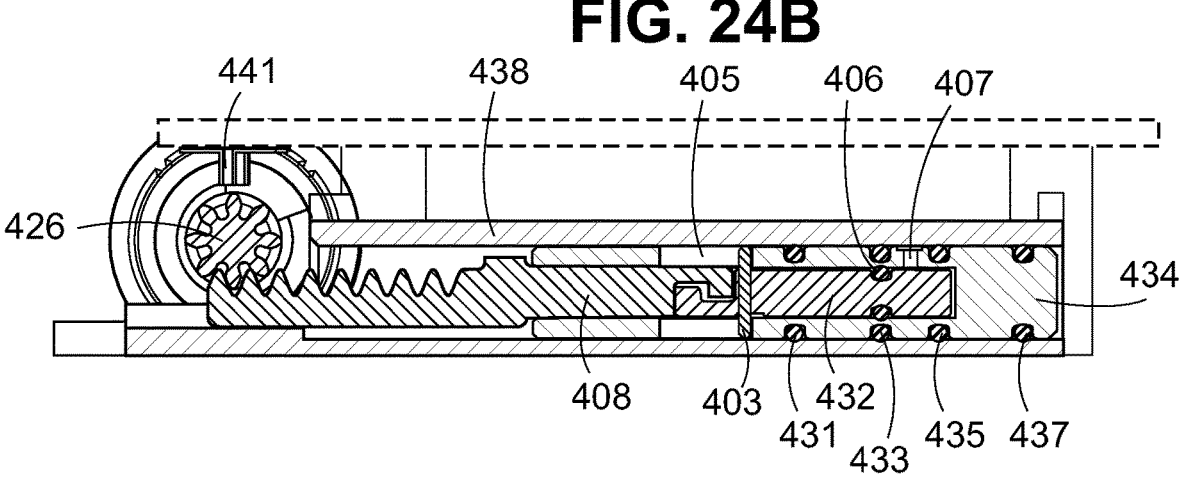
FIG. 24A and the corresponding cross section of FIG. 24B depict the starting position of the pump cycle according to an embodiment of the invention.

FIG. 24A and the corresponding cross section of FIG. 24B depict the starting position of the pump cycle. The axial extension 408 of drive rack 428 is fully extended into spool 434 and coupling pin 403 abuts the axial end of elongated slot 405, defining the furthest extension of drive piston 432 into spool 434. Seals 433 and 431 on the spool block cannula port 452, leaving reservoir port 451 open to the middle segment of the spool.

Figures 25A, 25B:
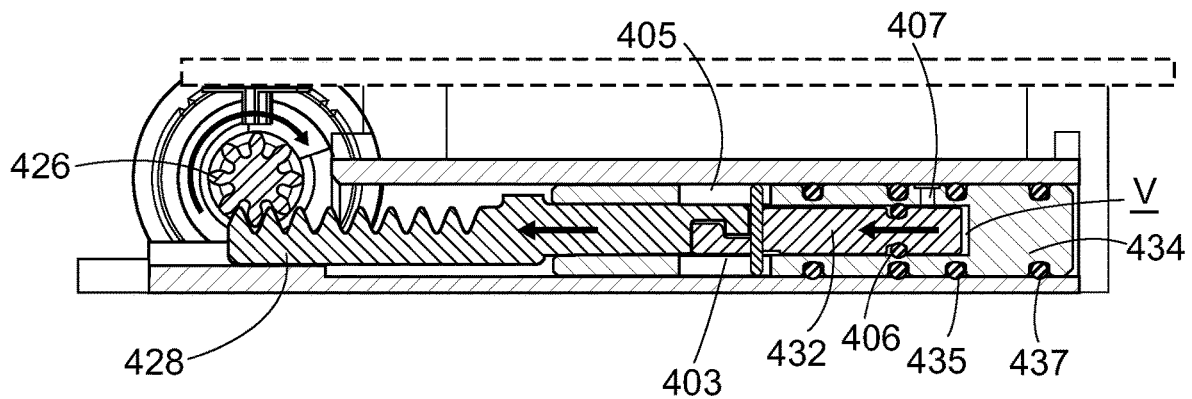
FIG. 25A, FIG. 25B, FIG. 26A, FIG. 26B, FIG. 27A, FIG. 27B, FIG. 28A, FIG. 28B, FIG. 29A, and FIG. 29B depict stages of the pump cycle of the fluid metering system according to the embodiment of FIG. 21.

FIG. 25A and the corresponding cross section of FIG. 25B depict the intake stroke according to this embodiment of the invention. During the intake stroke, drive piston 432 is axially displaced within the floating piston bore 409 in the direction indicated by the arrow remaining entirely within bore 409 throughout the pump cycle, while floating piston 434 initially remains stationary due to frictional engagement of seals 431, 433, 435, and 437 on floating piston 434 with the internal surface of the pump housing 438. Fluid is drawn into the pump volume space V in bore 409 from the reservoir through reservoir port 451 and opening 407 in floating piston 434. During the intake stroke, friction between the seals on the spool and the internal diameter of the pump housing must be high enough to ensure that negative intake pressure acting on the face of the floating piston does not move the spool before the intake stroke is complete. The intake stroke is designed so that a stepwise increasing load is applied to the motor, which is advantageous to motor efficiency and battery life. The coupling between hooks 401 and 402 on the drive rack and drive piston, respectively, allows the motor to start under light load, minimizing start up currents which adversely affect battery life. Drive rack 428 does not engage and begin to move drive piston 432 until the gap closes. Drive piston 432 has one sliding seal 406 in frictional engagement with the internal surface of bore 409 of floating piston 434. Initially, as the pump volume V begins to expand, an additional pressure load is placed on the end of the drive piston as a result of negative pressure in the bore, further increasing the load on the motor.

Figures 26A, 26B:
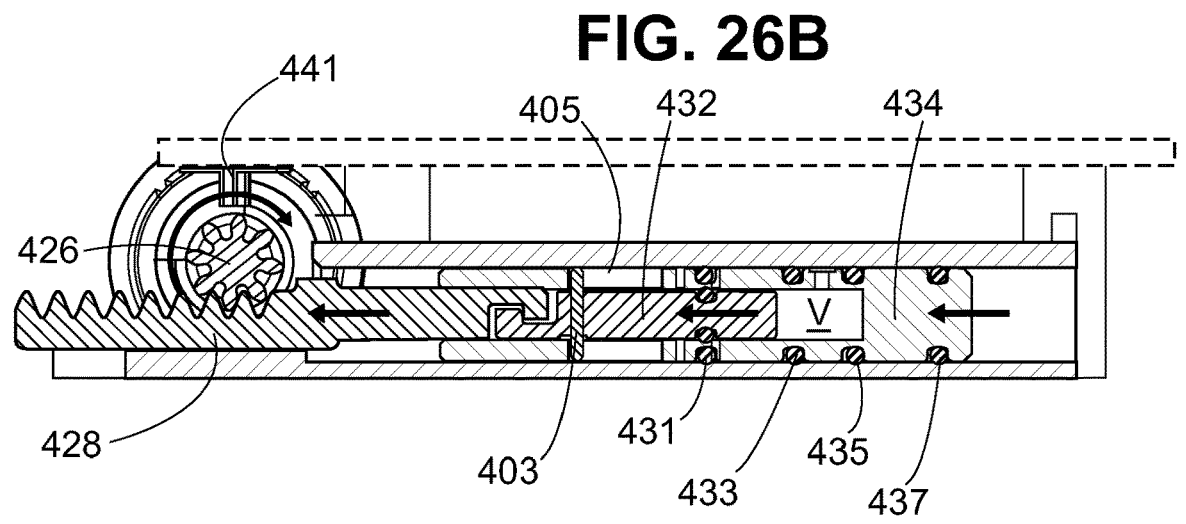

As shown in FIG. 26A and the corresponding cross section of FIG. 26B, once the pump volume V fully expands and fills with fluid, the pressure and piston friction loads decrease and drive piston 432 begins to pull floating piston 434 via coupling pin 403, as shown by the arrows, further increasing the load on the motor due to the frictional engagement of the four sliding seals 431, 433, 435 and 437 with the internal surface of pump housing 438.

During the valve state change, the reservoir inlet is first blocked as seal 435 on floating piston 434 passes over reservoir port 451. Cannula port 452 then opens to the expanded pump volume space V in bore 409 of floating piston 434. When the intake stroke is completed, a travel limit sensor 441 triggers the motor to change direction. As with any of the embodiments, travel limit sensor 441 may trigger when the limit of the drive rack travel is reached, or a more precise mechanism may be employed, such as an optical sensor and an encoder, which counts the teeth on gear 426 as the gear rotates.

Figures 27A, 27B:
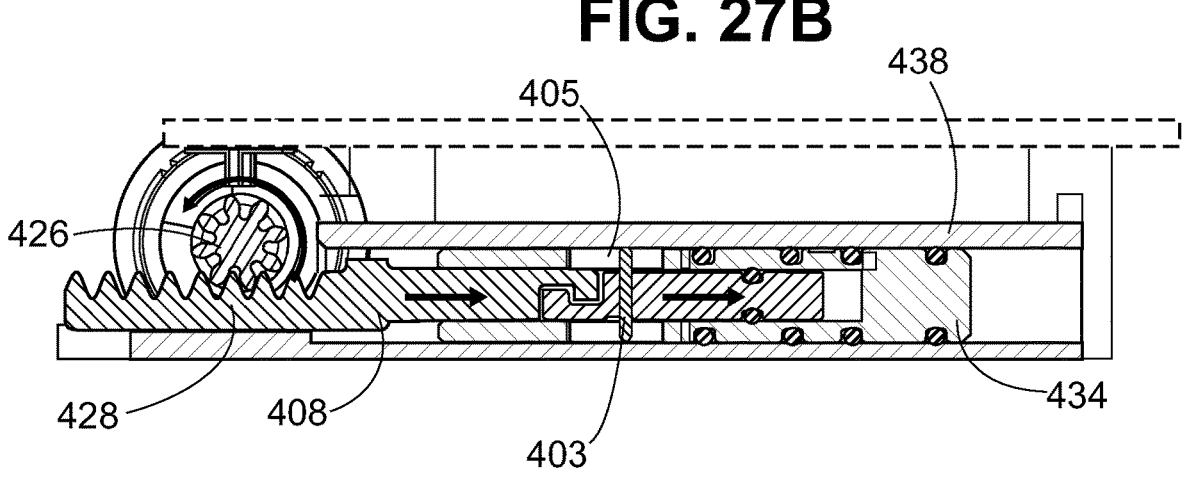
Figures 28A, 28B:
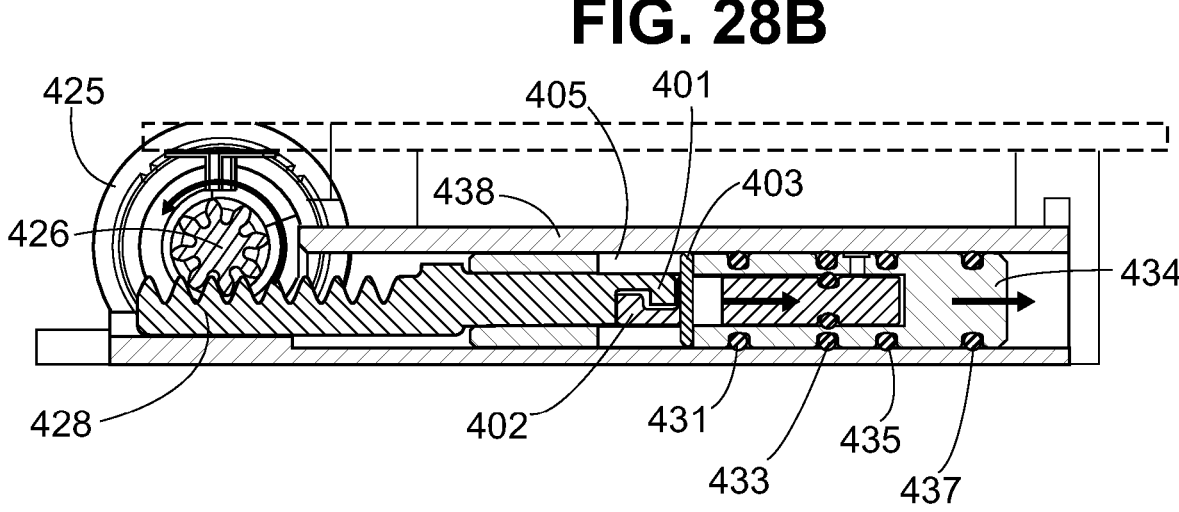
Figures 29A, 29B:
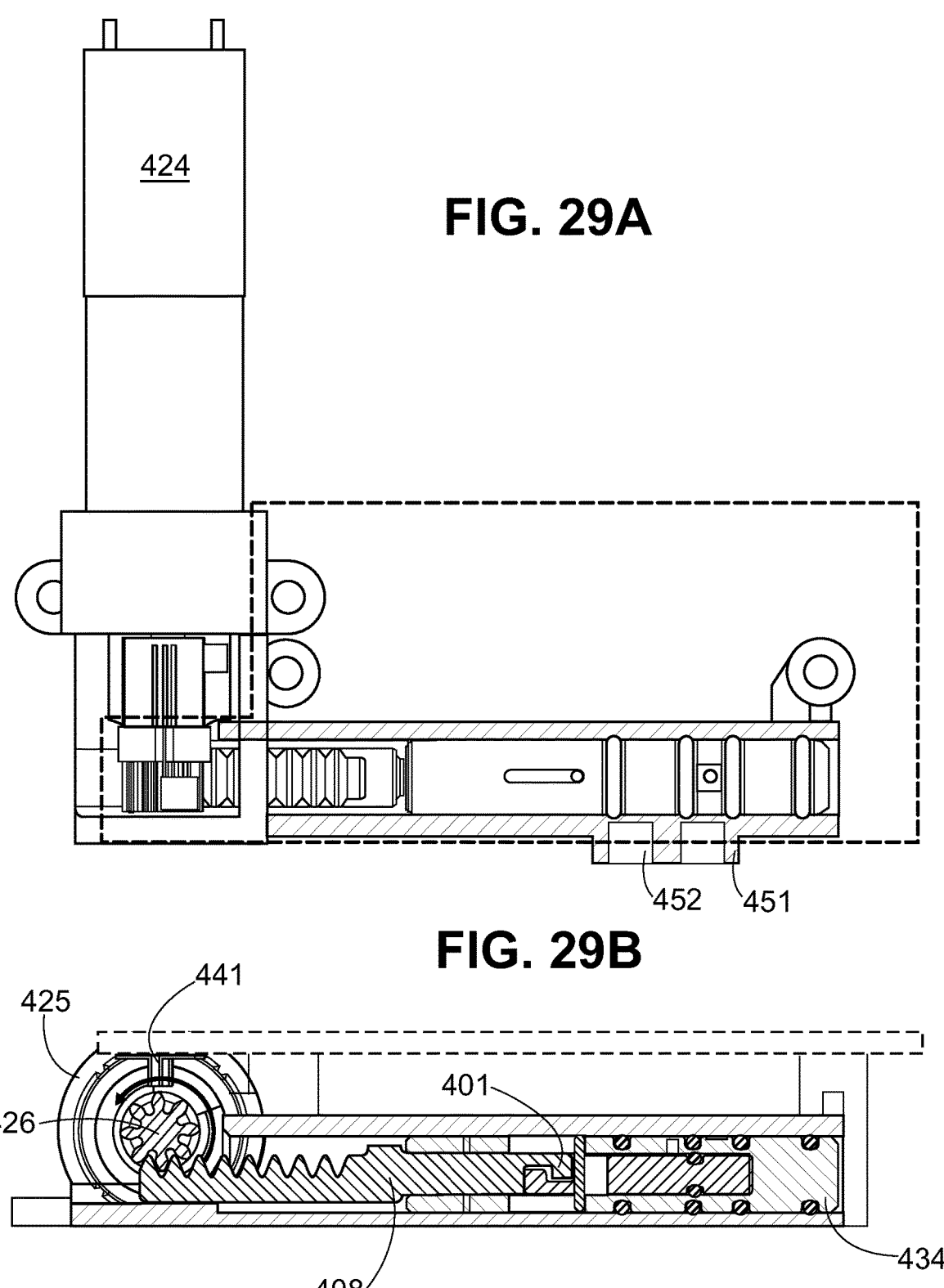
Figure 30:
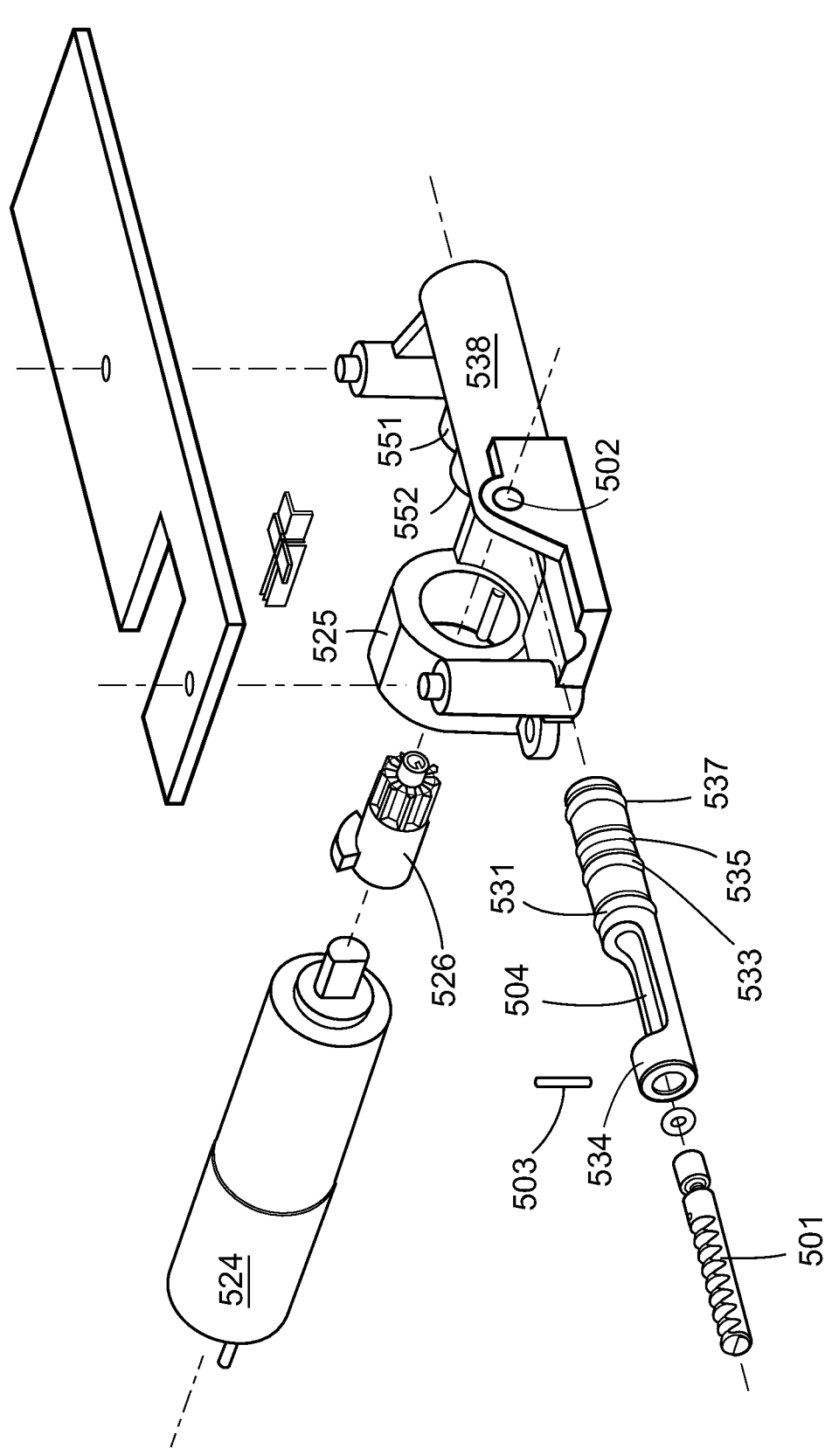
FIG. 30 is an exploded view of a fluid metering subsystem according to a fourth exemplary embodiment of the invention.

During the discharge stroke, depicted in FIG. 27A and FIG. 27B, motor 424 rotates counterclockwise (looking in a direction down the motor shaft toward the motor) and floating piston 434 is again initially stationary as a result of the frictional engagement of the seals. Drive piston 432 compresses pump volume space V to expel fluid through cannula port 452. After the discharge stroke, in the state depicted in FIGS. 28A and 28B, the pump volume V is fully collapsed and floating piston 434 begins to move in tubular pump housing 438. The valve changes state and cannula port 452 is blocked as seal 435 passes over the aperture, after which reservoir port 451 opens to aperture 407 in floating piston 434. FIG. 29A and FIG. 29B depict the final stages of the pump cycle, returning the piston assembly to the position in which the drive rack is fully extended at the completion of the pump cycle.

In a fourth embodiment of the invention, depicted in FIGS. 30 through 40B, the drive rack and piston are combined into one driven piston 501 which remains entirely within the floating piston bore throughout the pump cycle. A window 504 is cut into the side of the floating piston 534 to allow gear 526 to engage driven piston 501 received inside the pump housing and move it axially. This arrangement permits a shorter axial length for pump housing 538 and a smaller overall footprint.

Figures 31, 32:
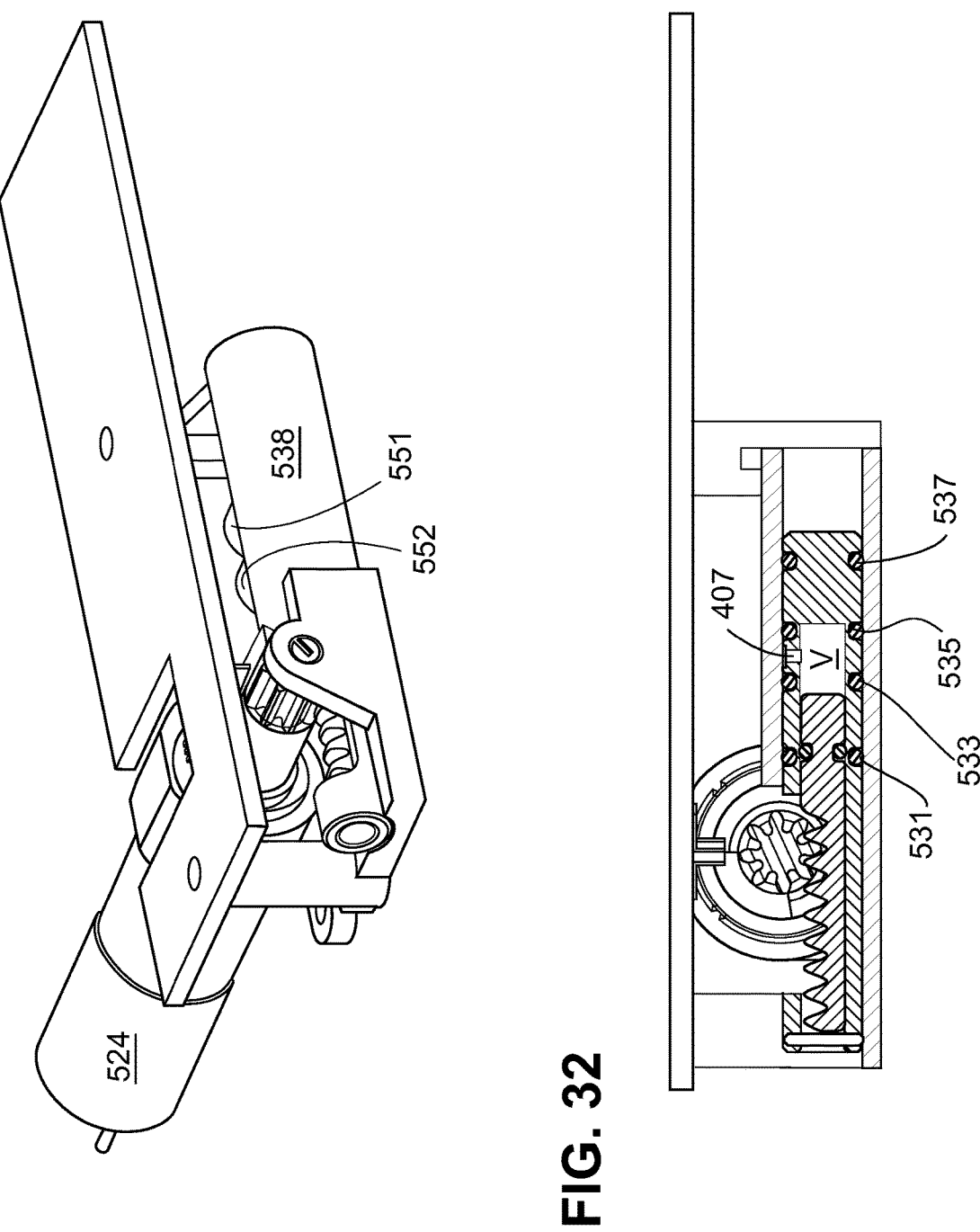
FIG. 31 depicts the assembled embodiment of FIG. 30.
FIG. 32 is a side cross-sectional view of the embodiment of FIG. 30.
Figure 33A:
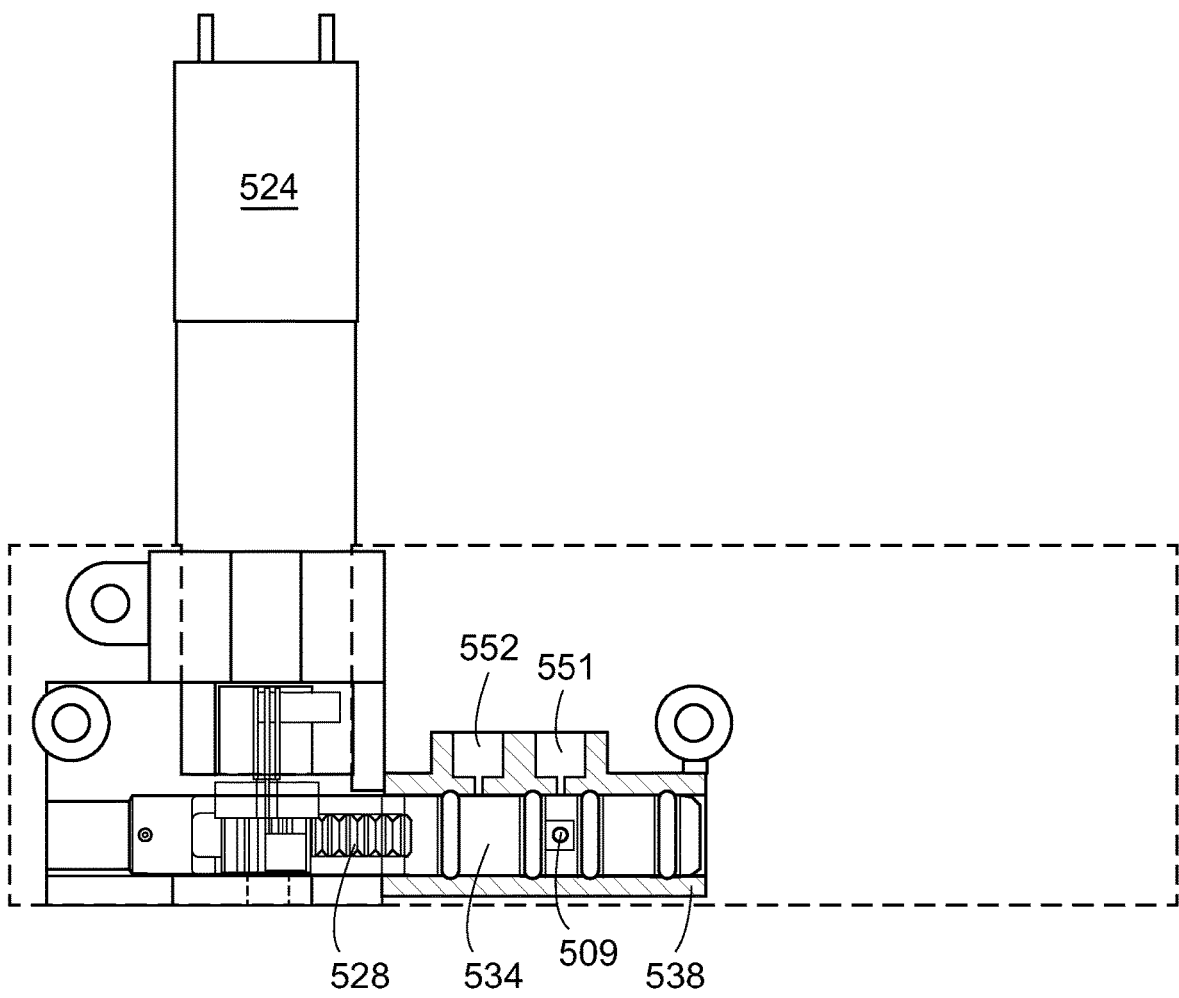
FIG. 33A, FIG. 33B, FIG. 34A, FIG. 34B, FIG. 35A, FIG. 35B, FIG. 36A, FIG. 36B, FIG. 37A, FIG. 37B, FIG. 38A, FIG. 38B, FIG. 39A and FIG. 39B depict stages of the pump cycle of the fluid metering system according to the embodiment of FIG. 3.
Figure 33B:
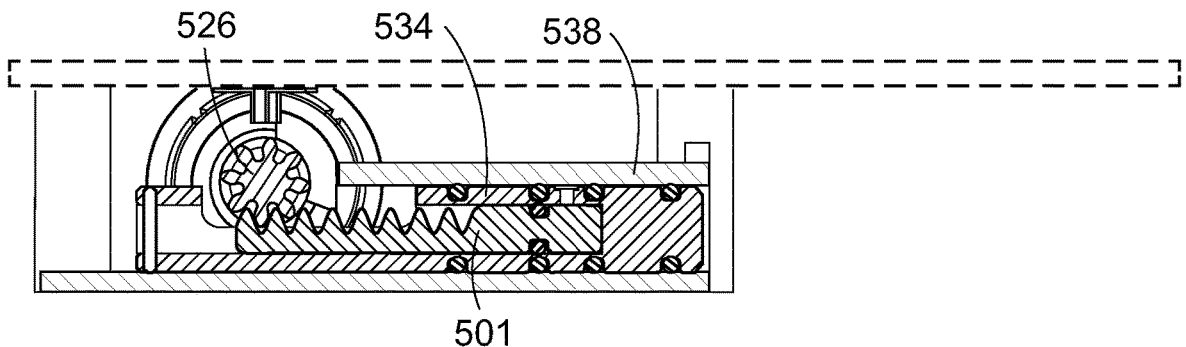
Figure 34A:
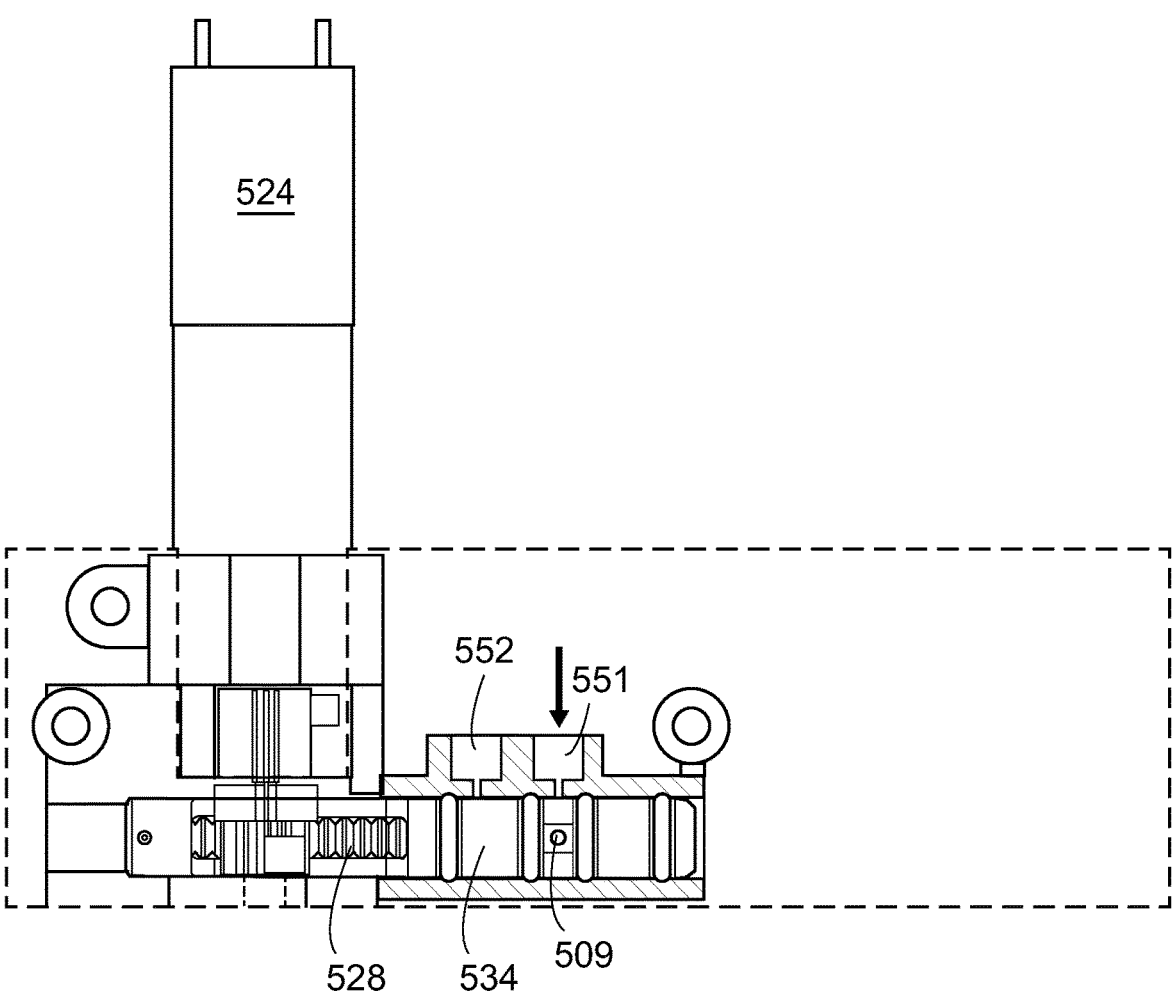
Figure 34B:
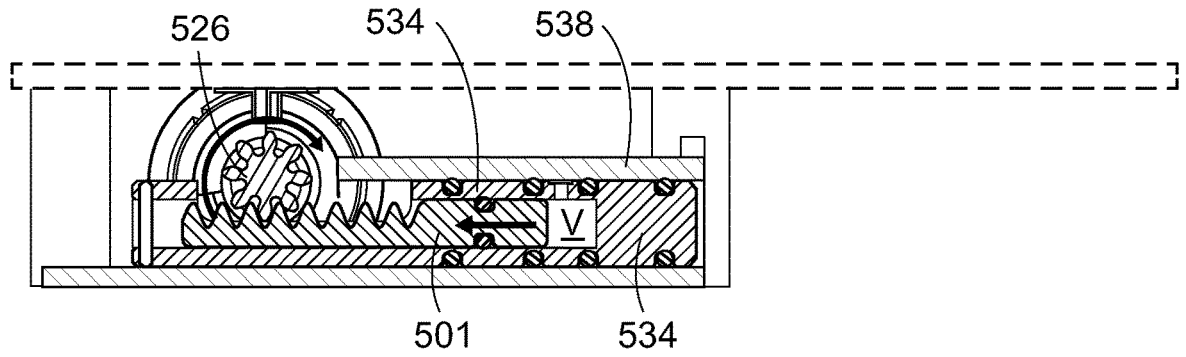

In the assembled view of FIG. 31, pump housing 538 is shown formed with a housing 525 to receive the motor 524 and a support 502 for the pinion gear 526, so that the gear can access the drive rack portion of driven piston 501 through opening 504 in the floating piston 534.

Figure 35A:
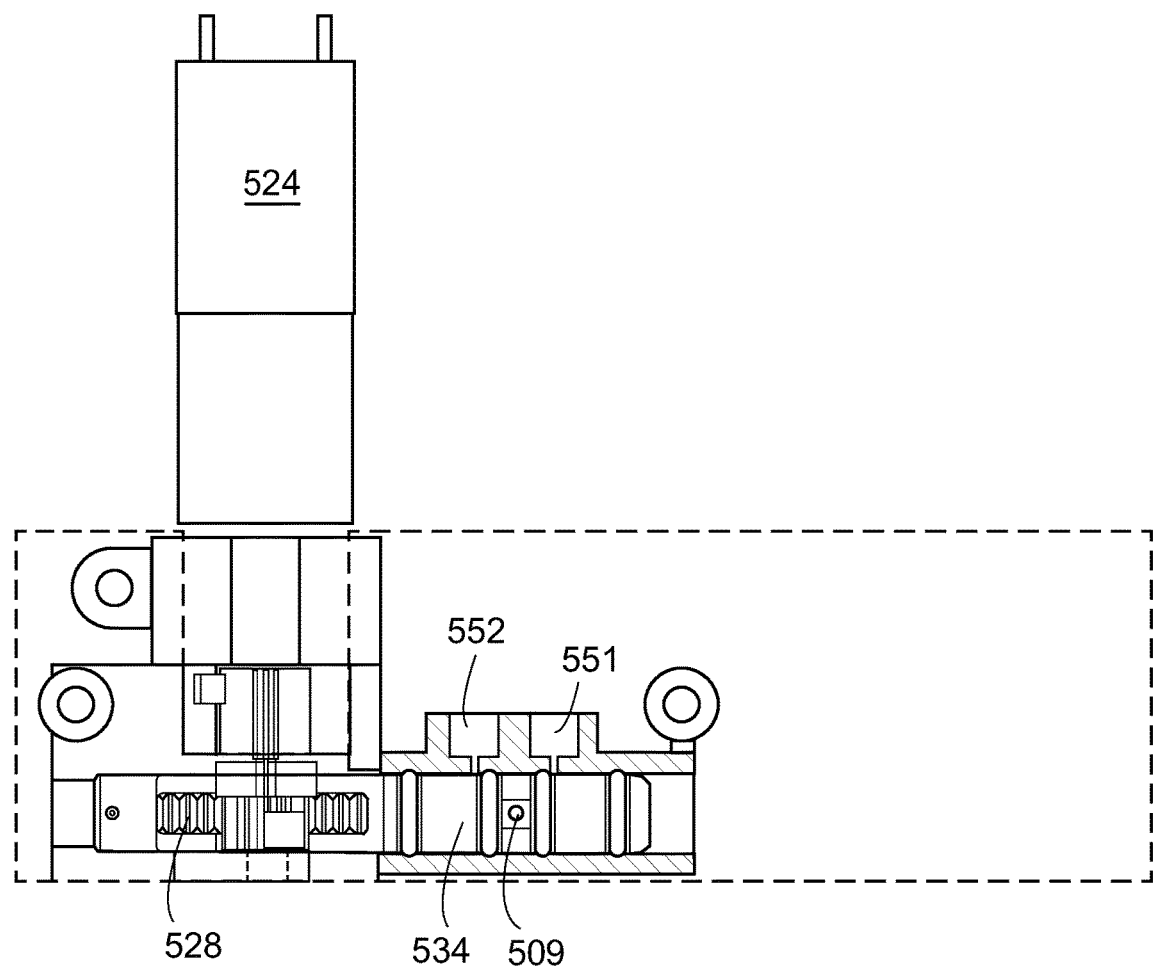
Figure 35B:
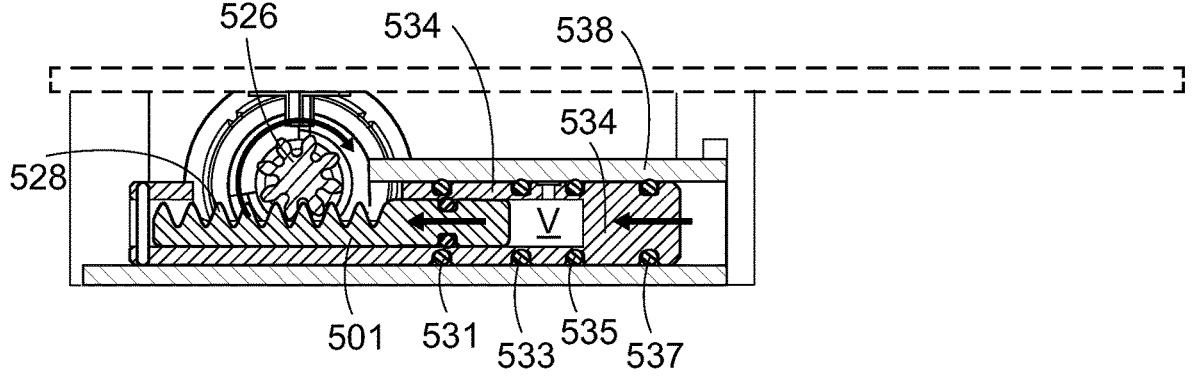
Figure 36A:
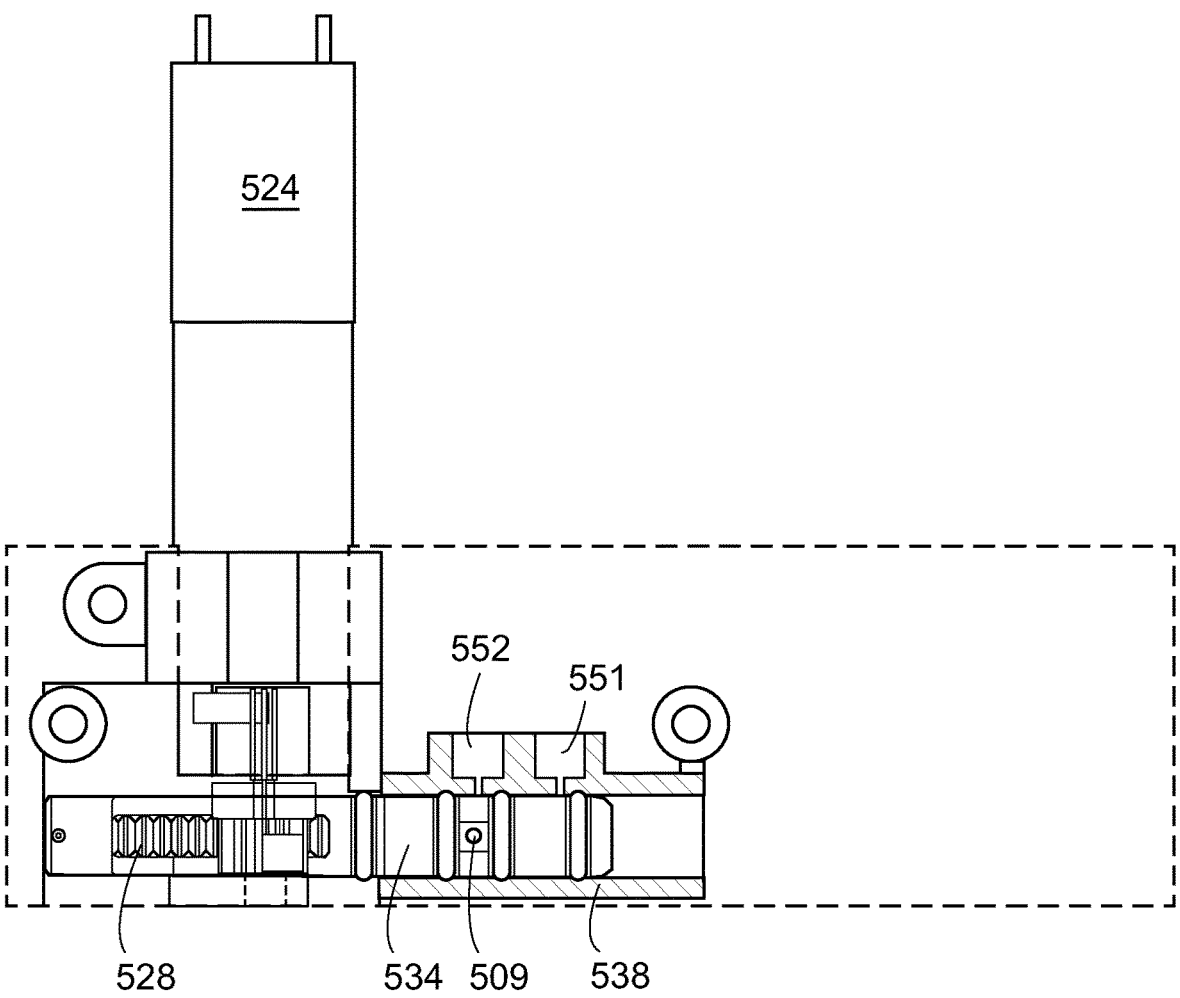
Figure 36B:
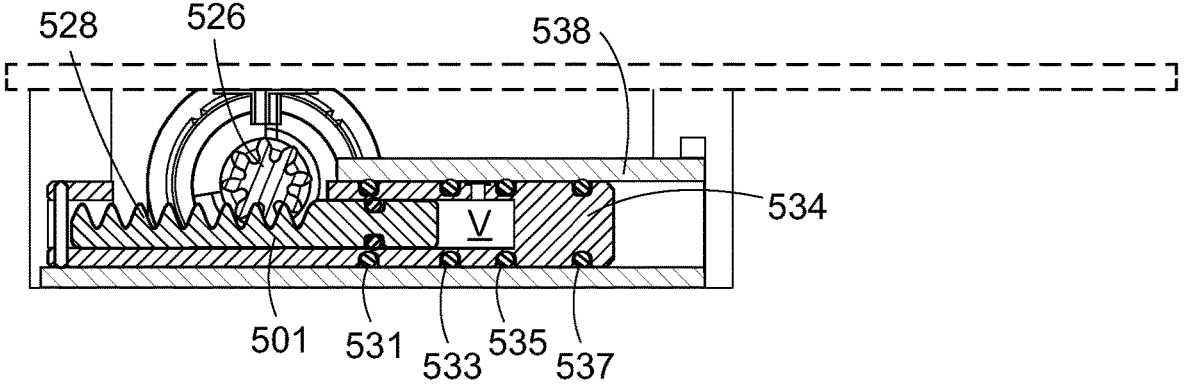
Figure 37A:
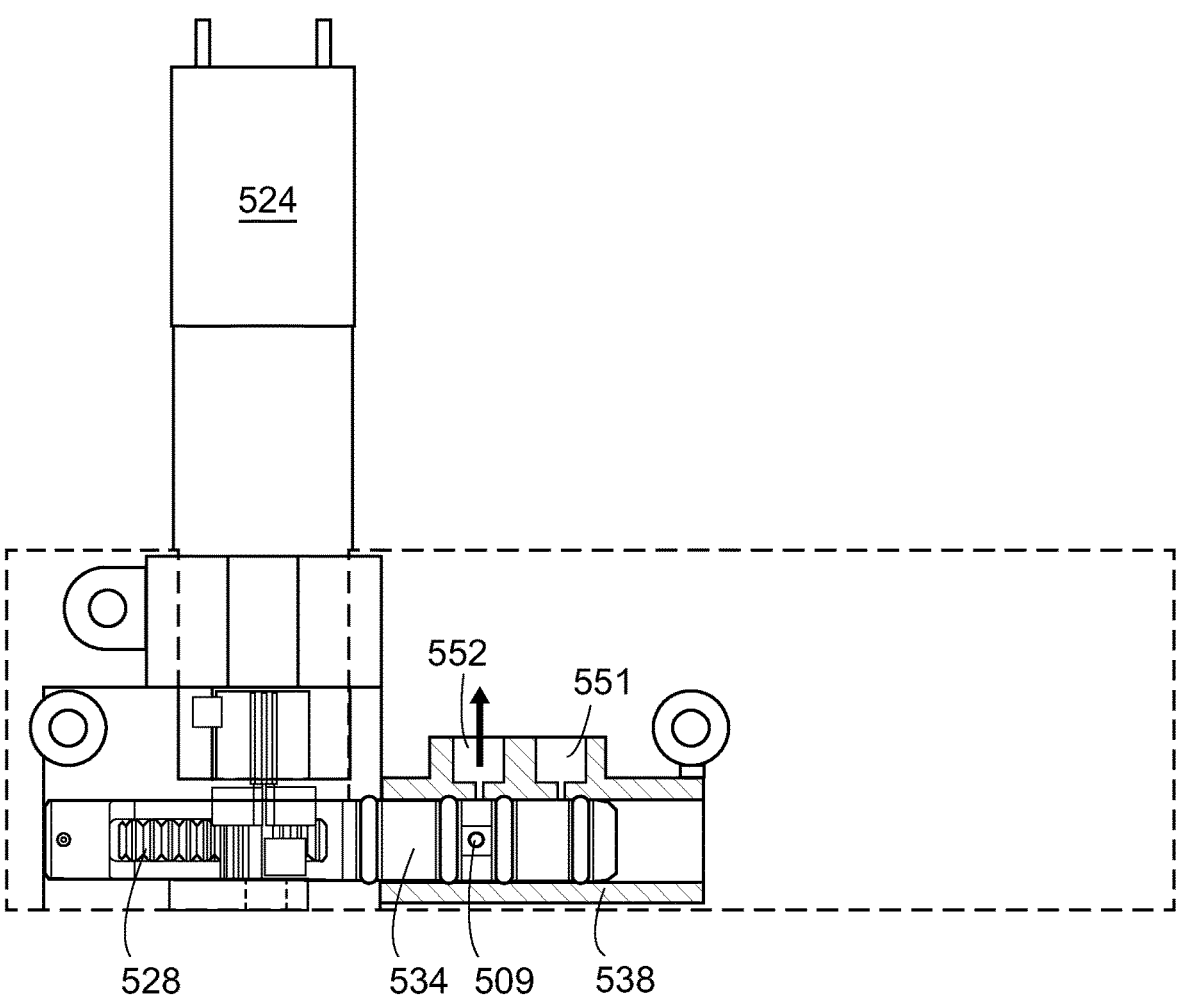
Figure 37B:
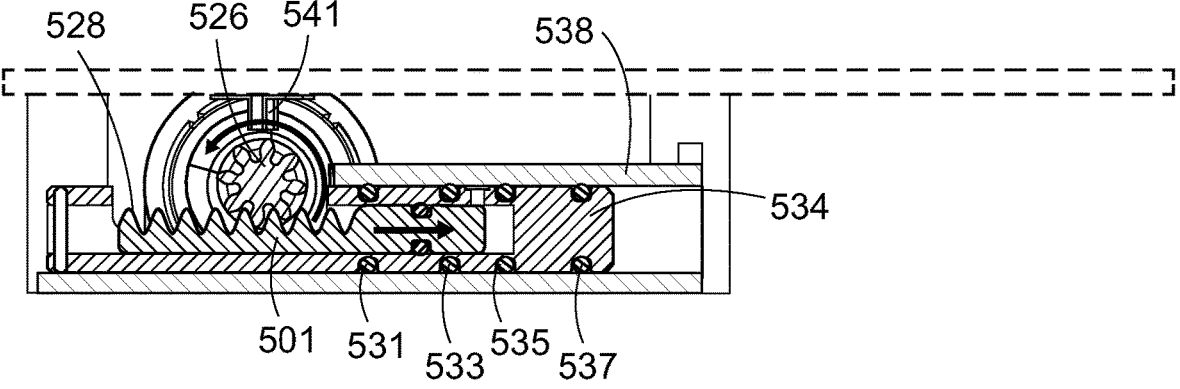
Figure 38A:
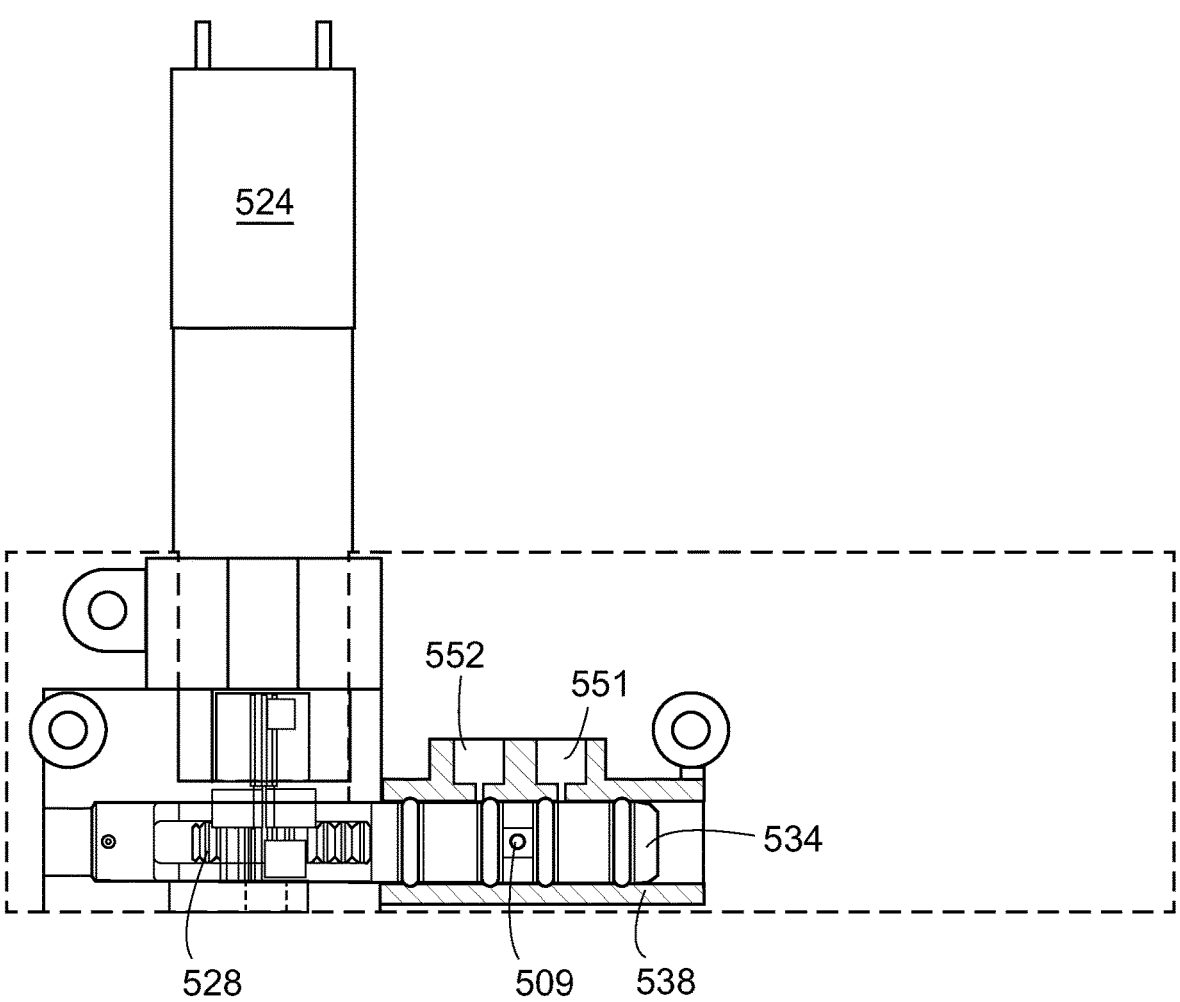
Figure 38B:
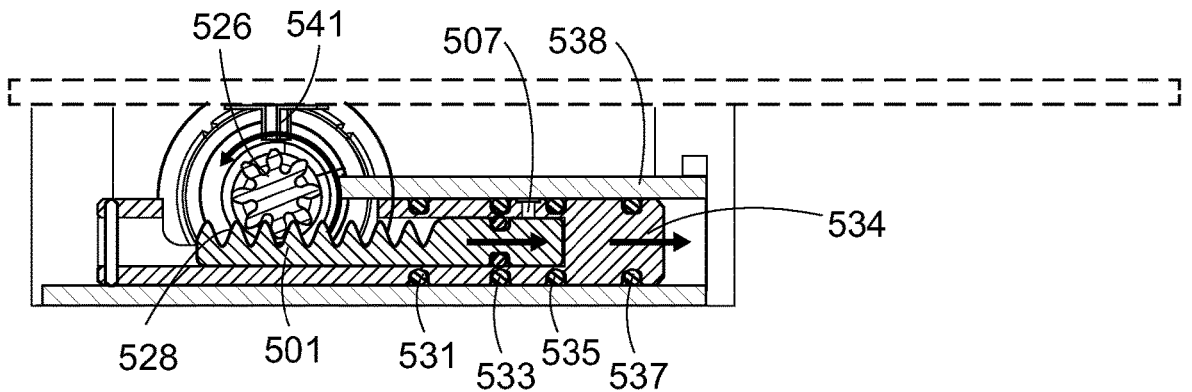
Figure 39A:
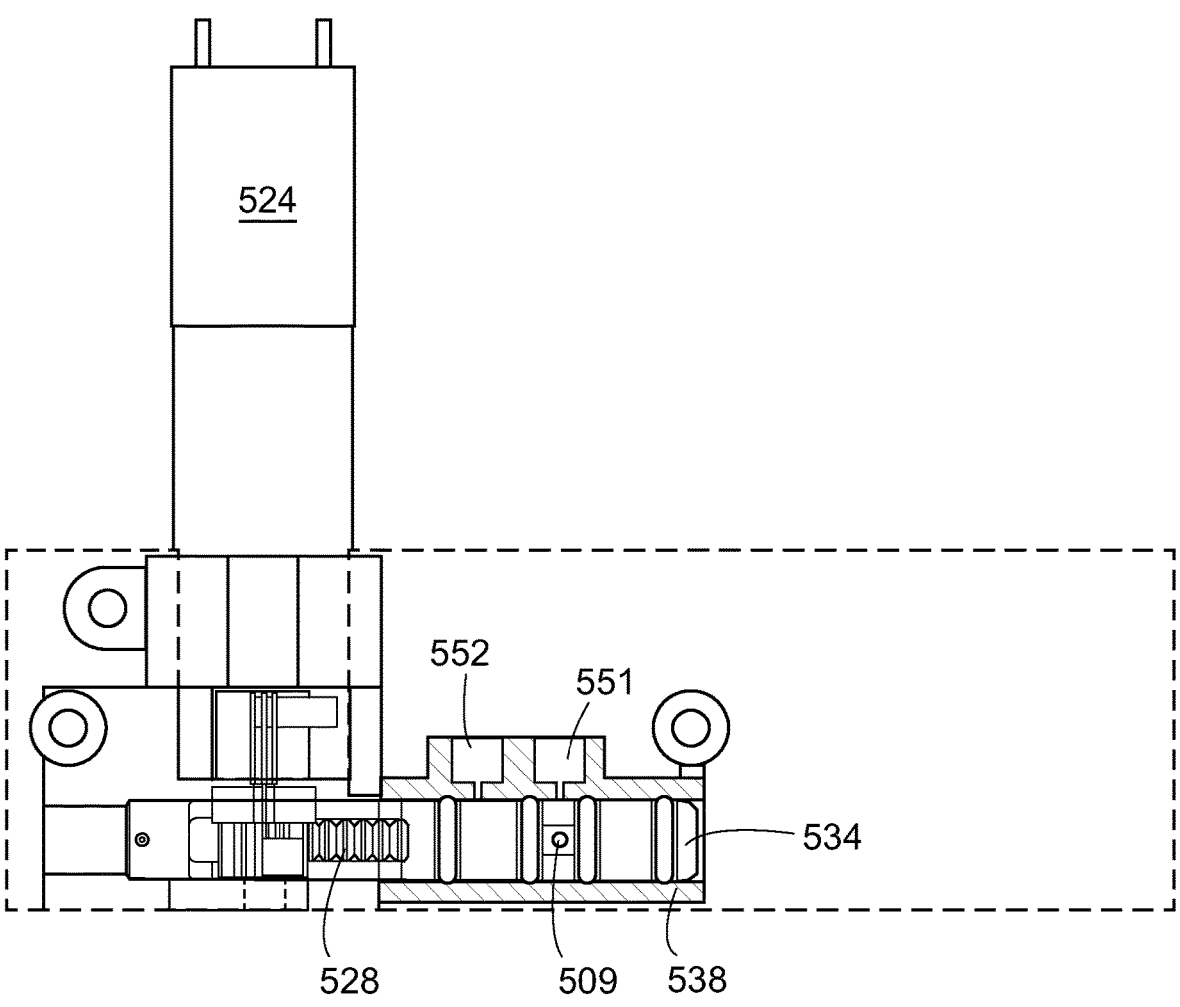
Figure 39B:
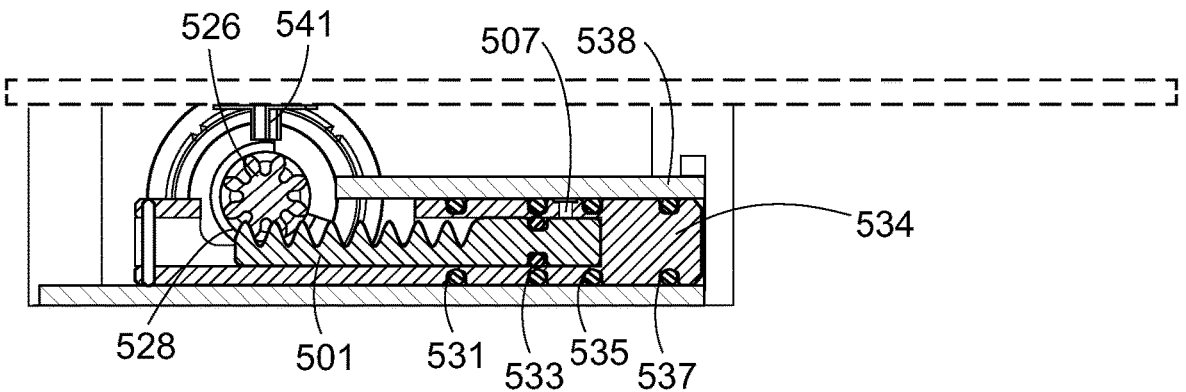
Figure 40:
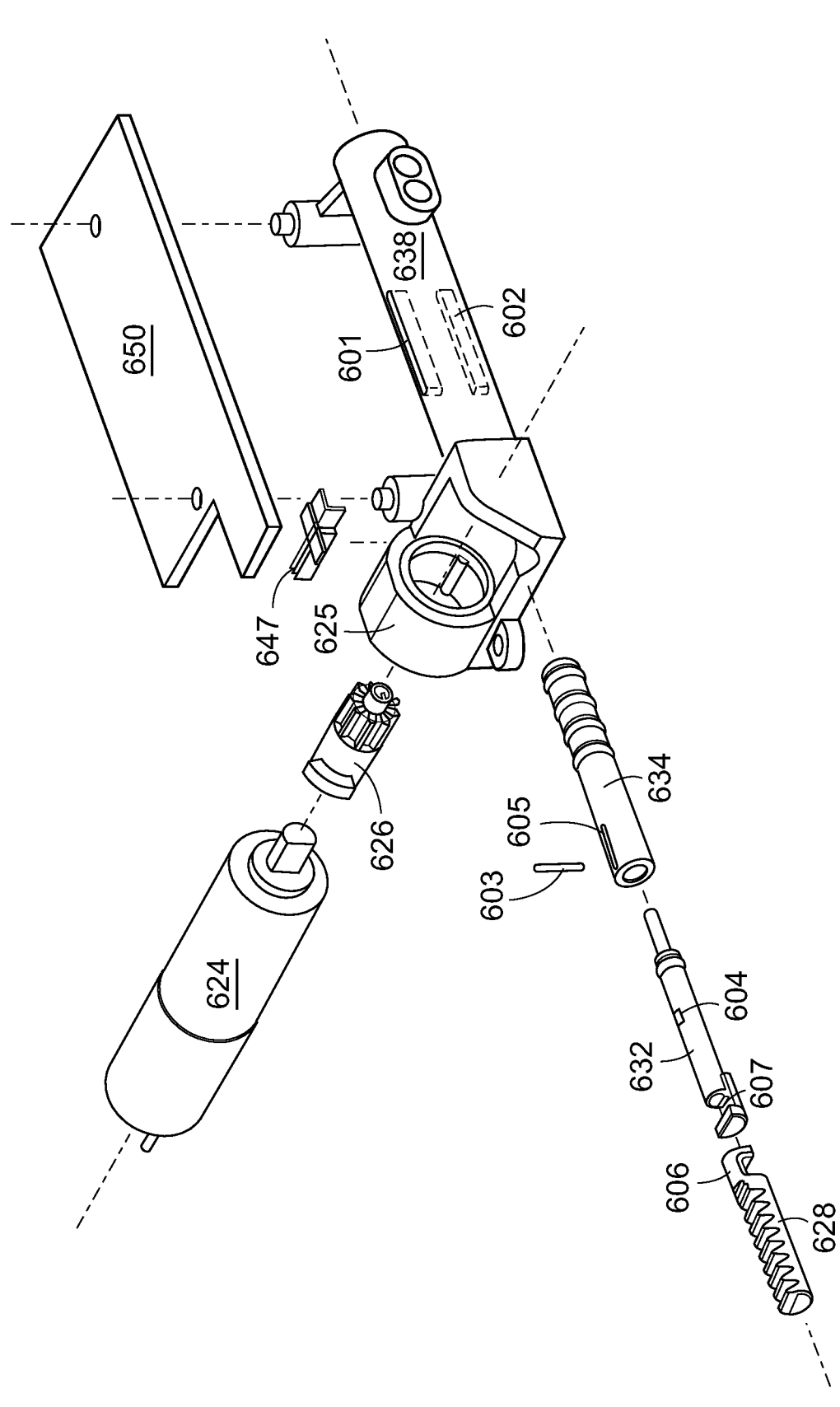
FIG. 40 is an exploded view of a fluid metering subsystem according to a fifth exemplary embodiment of the invention.

The pump cycle for the fourth embodiment is similar to the pump cycle for the previous embodiment. In the extended position of FIG. 33A, the combined drive rack/piston 501 is fully extended into the bore of the floating piston 534, and the floating piston is at the far end of pump housing 538 in the direction away from gear 526. Cannula port 552 and the reservoir port 551 are positioned on the side of the pump housing facing the motor, although this positioning is arbitrary. During the intake stroke, depicted in FIGS. 34A and 34B, the combined drive rack/piston 501 is driven by gear 526 rotating in the clockwise direction to expand the pump volume space V in the bore of floating piston 534, or spool as it is also called in this embodiment. Fluid is drawn into the pump volume space V through port 551. FIG. 35A and FIG. 35B depict the position of the floating piston 534 after the intake stroke during the valve state change. Once the pump volume is fully expanded, motor 524 overcomes the frictional engagement of spool with the internal surface of tubular pump housing 538 and the spool is pulled by the action of the motor. Reservoir port 551 is initially blocked as seal passes over the aperture. At the completion of this stage of the pump cycle, as shown in FIG. 36A and FIG. 36B, expanded pump volume V in the bore of the spool 534 is aligned to cannula port 552. As in the previous embodiments, the end of the intake stroke triggers a travel limit sensor 541 and motor 524 changes direction. In FIGS. 37A and 37B, the combined drive rack/piston component 501 compresses the pump volume V in the bore of the spool 534 expelling fluid from cannula port 552 to the infusion site. As shown in FIG. 38A and FIG. 38B, continued rotation of the gear 526 pushes the combined drive rack/piston and the spool 534 back to the starting position, as shown in FIG. 39A and FIG. 39B.

Figure 41:
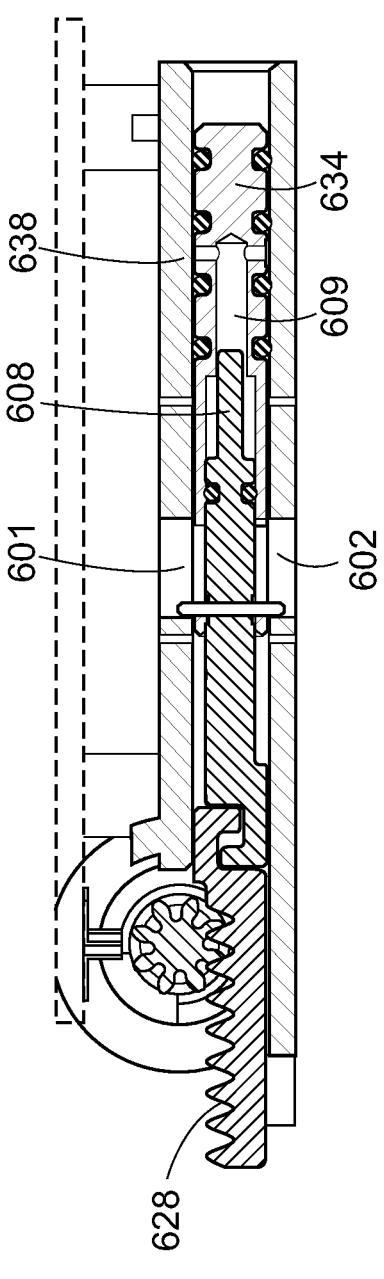
FIG. 41 is a cross sectional view of the assembled fluid metering system according to the embodiment of FIG. 40.

The fifth alternative embodiment of the invention is a variation of the piston-and-spool configuration described in connection with the fourth embodiment. In the fifth embodiment depicted in the exploded view of FIG. 40 and in cross-section in FIG. 41, the floating piston (or "spool" as it also called in this embodiment) 634 is coupled to the drive piston 632 with a pin 603 received through an axially elongated slot 605 in the floating piston and through a hole 604 in the drive piston 632. The pin travels in slots 601 and 602 in the tubular housing 638. However, the slots 601, 602 do not limit axial travel of the pistons and axial clearance is provided in slots 601 and 602 for the pin. These slots are provided for ease of assembly. The motion of pin 603 in slot 605 determines the stroke of the pump. The stroke of the drive piston depends upon the length of slot 605 and the diameter of pin 603. The pump volume space in this embodiment is defined by an axial extension 608 received in the bore 609 of the spool.

During the intake stroke depicted in FIG. 42A and FIG. 42B, opening 610 in spool 634 is aligned with reservoir port 651 and the spool blocks cannula port 652. The motor operating on drive rack 628 via gear 626 causes drive piston 632 to be axially displaced within the bore in spool 634, thereby expanding the pump volume space so that fluid is drawn into the space as a result of negative pressure. Pressure is maintained in the pump volume space by frictional engagement of seal 616 on drive piston 632 on an internal surface of spool 634. Initially, spool 634 does not move inside tubular housing 638, as a result of frictional engagement of radially compressed seals 631, 633, 635, and 637 with tubular housing 638.

Figures 43A, 43B:
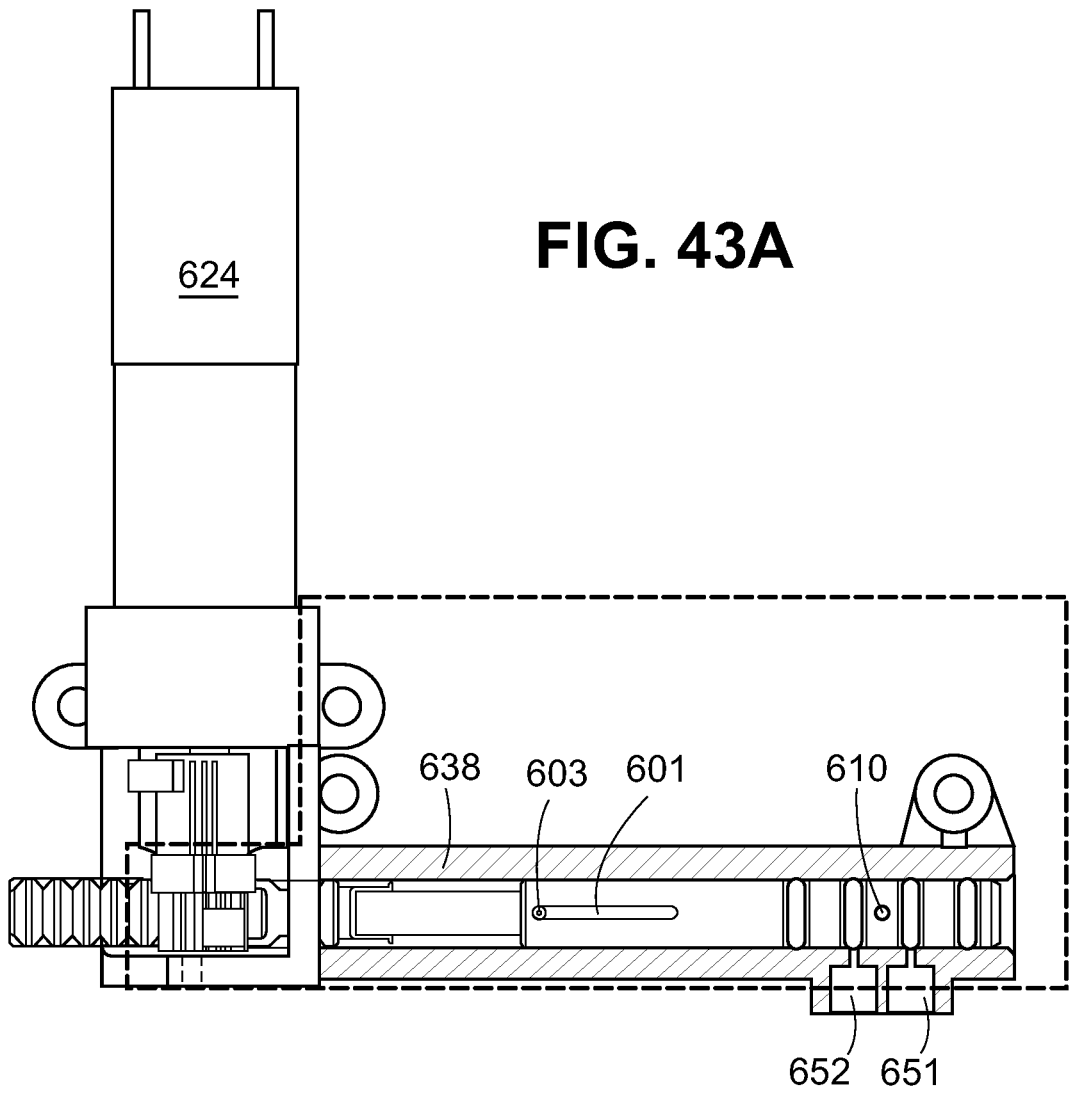
Figures 44A, 44B:
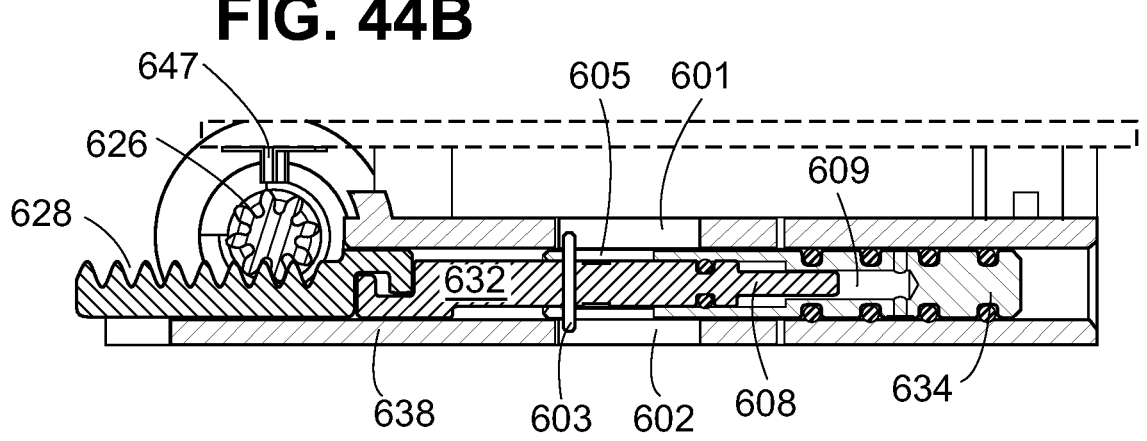
Figure 45A:
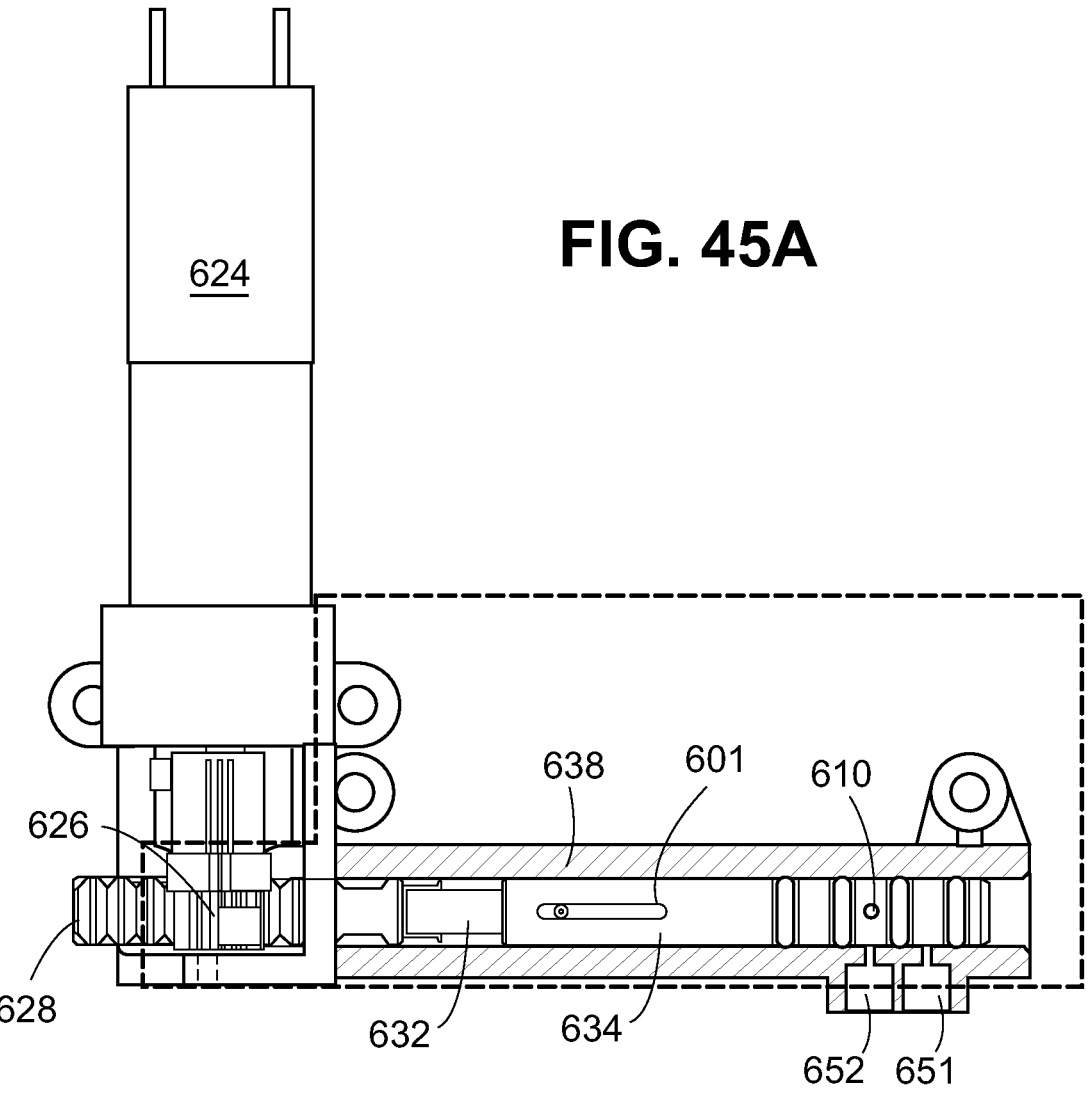
Figure 45B:
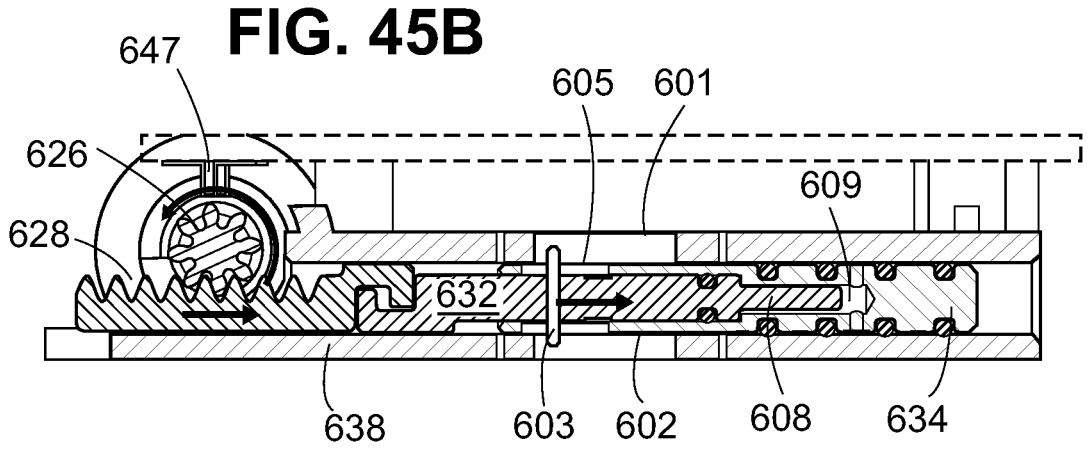
Figure 46A:
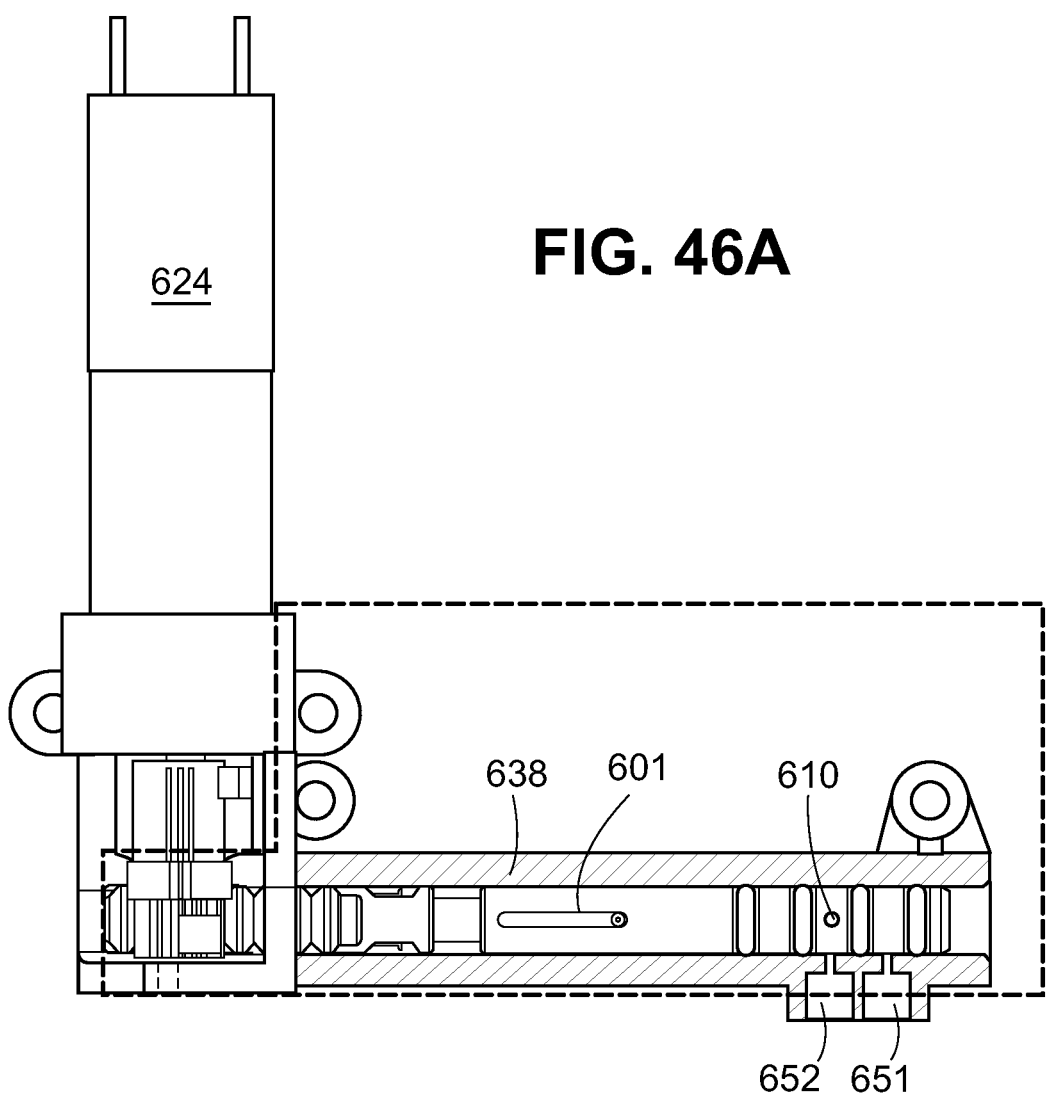
Figure 46B:
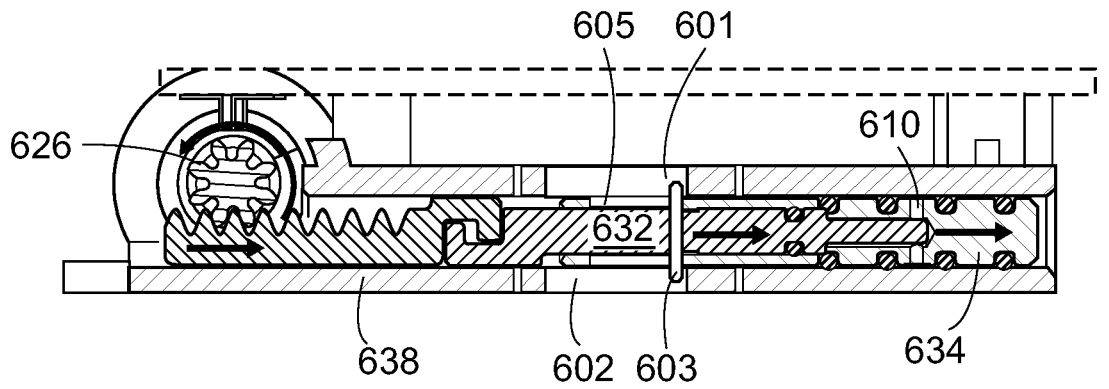
Figure 47A:
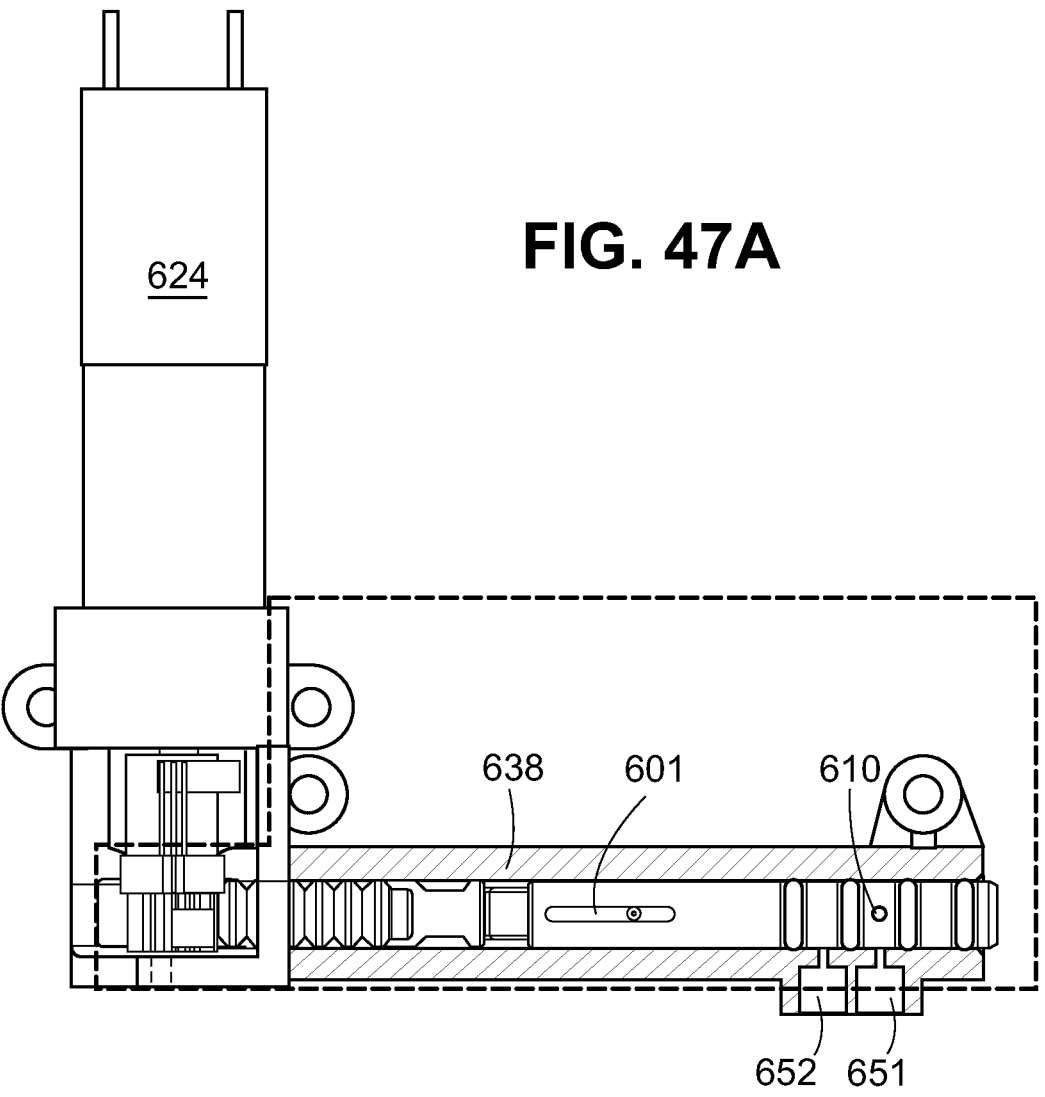
Figure 47B:
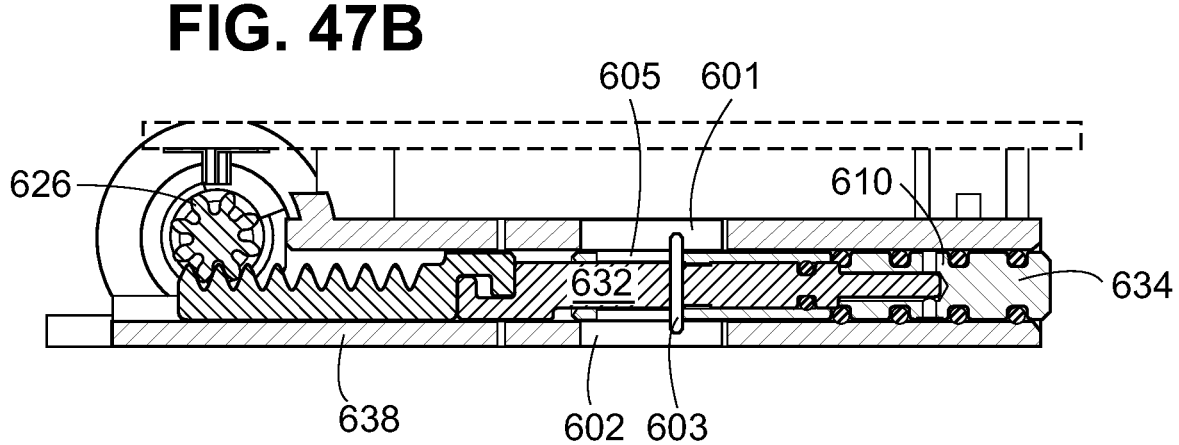

As shown in FIG. 43A and FIG. 43B, once the intake stroke is complete, drive piston 632 begins to pull spool 634 toward drive gear 626 via pin 603 bearing on the end of slot 605. Movement of spool 634 changes the state of the valve in a manner similar to that described in connection with previous embodiments. Opening 610 in spool 634 passes from reservoir port 651 to cannula port 652 as shown in FIG. 43A and FIG. 43B. In the fully retracted state of FIGS. 44A and 44B, travel limit sensor 647 is triggered and the discharge stroke of FIGS. 45A and 45B is initiated, pushing fluid out of cannula port 652. After completion of the discharge stroke, drive piston 632 begins to push spool 634 away from drive gear 626 via pin 603 bearing on the end of slot 605. Movement of spool 634 shown in FIGS. 46A and 46B changes the state of the valve. At the completion of the valve state change, the metering system has returned to the starting position of the pump cycle as shown in FIG. 47A and FIG. 47B.

The foregoing description of the preferred embodiments is not to be deemed limiting of the invention, which is defined by the appended claims. The person of ordinary skill in the art, relying on the foregoing disclosure, may practice variants of the embodiments described without departing from the scope of the invention claimed. For example, although described in connection with continuous delivery of insulin for treatment of diabetes, it will be apparent to those of skill in the art that the infusion pump could be adapted to deliver other medications. A feature or dependent claim limitation described in connection with one embodiment or independent claim may be adapted for use with another embodiment or independent claim, without departing from the scope of the invention.

What is claimed is:

1. A micropump for delivery of medication by infusion, comprising:
   a reservoir; a cannula; a motor; and a gear;
   a floating pump housing having a first aperture in fluid communication with the reservoir and a second aperture in fluid communication with the cannula, the floating pump housing having a drive rack engaged with the gear to move the pump housing axially;
   a fixed piston and a floating piston axially oriented within the pump housing;
   the fixed piston and floating piston being positioned to close the first and second aperture at first and second axial positions, respectively, of the fixed piston and floating piston within the floating pump housing; wherein
   the motor is engaged to the gear and the gear is engaged to the drive rack to translate the floating pump housing axially with respect to the fixed piston and the floating piston, wherein translating the drive floating piston with respect to the fixed piston defines a pump volume space within the floating pump housing;
   wherein the fixed piston is in a fixed position, the floating piston is not coupled to the floating piston, and the floating pump housing is translated by the motor and gear to obtain said first and second axial positions; and
   further comprising a cradle having a first keying rib receiving the fixed piston and maintaining the drive fixed piston in said fixed position, and a second keying rib receiving the floating piston, the floating piston having a groove contacting the second keying rib, wherein axial ends of the groove define the limits of axial movement of the floating piston against the second keying rib.

2. The micropump of claim 1, wherein axial movement of the floating pump housing first translated the floating piston, then translates the pump volume from a position oriented with the first aperture to a position oriented with the second aperture.

3. A micropump for delivery of medication by infusion, comprising:
   a reservoir; a cannula; a motor; a gear;
   a pump housing having a first aperture in fluid communication with the reservoir and a second aperture in fluid communication with the cannula;
   a drive piston comprising a rack, and a floating piston axially oriented within the pump housing;
   the drive piston and the floating piston being positioned to close the first and second aperture at first and second axial positions, respectively, of the drive piston and floating piston within the pump housing; wherein
   the motor is engaged to the gear and the gear is engaged to the rack to translate the drive piston axially with respect to the floating piston,
   wherein the floating piston comprises a bore receiving a portion of the drive piston to define a pump volume space in the bore, and a through-hole on the floating piston fluidly connecting the bore and an outer surface of the floating piston, said through hole positioned to provide access to the reservoir via the first aperture in a first position and access to the cannula via the second aperture in a second position.

4. The micropump according to claim 3, comprising a radially positioned O-ring sealon the drive piston radially compressed against an interior surface of the bore in the floating piston.

5. A micropump for delivery of medication by infusion, comprising:
   a reservoir; a cannula; a motor; a gear;
   a tubular pump housing having a first aperture in fluid communication with the reservoir and a second aperture in fluid communication with the cannula;
   a drive rack operatively connected to the gear; a drive piston in the pump housing;
   a floating piston axially aligned with the drive piston and coupled to the drive piston; at least one radial seal on the floating piston in frictional engagement with an interior surface of the pump housing, and at least one radial seal on the drive piston in frictional engagement with an interior surface of the pump housing; wherein the motor is engaged to the gear, the gear is engaged to the drive rack and the drive rack is engaged to the drive piston to translate the drive piston and the floating piston axially within the pump housing; wherein translating the drive piston with respect to the floating piston defines a pump volume space within the pump housing; and wherein the floating piston closes the first aperture and the drive piston closes the second aperture at different axial positions of the drive piston and floating piston within the pump housing;

further comprising a first hook on the floating piston;

a second hook on one end of the drive piston coupled to the first hook on the floating piston;

a third hook on a second end of the drive piston axially opposite said first end of the drive piston; and a fourth hook on the drive rack coupled to the third hook on the drive piston;

a gap between the first hook and the second hook permitting defined axial movement of the floating piston with respect to the drive piston; and a gap between the third hook and the fourth hook permitting defined axial movement of the drive rack with respect to the drive piston.

6. The micropump according to claim 5, comprising a travel limit sensor operatively communicating with the gear when the drive rack is fully extended toward the pump housing and fully retracted from the pump housing.

7. A micropump for delivery of medication by infusion, comprising:

a reservoir; a cannula; a motor; a gear; a drive piston comprising a rack;

a pump housing having a first aperture in fluid communication with the reservoir and a second aperture in fluid communication with the cannula;

the drive piston received in a floating piston axially arranged in the pump housing, the drive piston having a portion received in a bore in the floating piston, defining a pump volume space between the bore and the drive piston;

a through-hole on the floating piston fluidly connecting the bore and an outer surface of the floating piston, said through hole positioned to provide access from the reservoir to the pump volume space via the first aperture in a first position and access from the pump volume space to the cannula via the second aperture in a second position.

8. The micropump according to claim 7, further comprising a coupling pin received through a slot in the floating piston and received into the drive piston, wherein the slot in the floating piston is elongated in the axial direction and has opposite axial ends defining the extent of axial movement of the drive piston in the bore of the floating piston.

9. The micropump according to claim 7, further comprising a radial seal on the drive piston in frictional engagement with an interior surface of the bore of the floating piston;

two pairs of radially positioned seals on the floating piston in frictional engagement with an interior surface of the tubular pump housing.

10. The micropump according to claim 7, wherein the drive piston comprises a single unitary element.

11. The micropump according to claim 7, wherein the floating piston is provided with an elongated opening permitting access by the gear to the drive rack through the opening.

12. The micropump according to claim 7, wherein the drive piston comprises a rack portion and a piston portion, and the rack portion is coupled to the piston portion by a first hook on the rack portion engaging a second hook on the piston portion, wherein a gap between the first hook and the second hook permits axial movement of the rack portion with respect to the piston portion before the rack portion engages the piston portion.

13. The micropump according to claim 7, wherein the drive piston is completely received within the bore of the floating piston throughout the pump cycle.

* * * * *